US007967872B2

(12) United States Patent
Daubresse et al.

(10) Patent No.: US 7,967,872 B2
(45) Date of Patent: Jun. 28, 2011

(54) AZO QUINOLINIUM COMPOUNDS COMPRISING A DISULPHIDE/THIOL UNIT, COMPOSITIONS CONTAINING SAME, PROCESS FOR DYEING KERATIN FIBRES AND DEVICE

(75) Inventors: Nicolas Daubresse, La Celles St Cloud (FR); Andrew Greaves, Montevrain (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 12/677,450

(22) PCT Filed: Sep. 8, 2008

(86) PCT No.: PCT/EP2008/061885
§ 371 (c)(1),
(2), (4) Date: Jun. 28, 2010

(87) PCT Pub. No.: WO2009/034059
PCT Pub. Date: Mar. 19, 2009

(65) Prior Publication Data
US 2010/0263139 A1    Oct. 21, 2010

Related U.S. Application Data

(60) Provisional application No. 60/960,190, filed on Sep. 19, 2007.

(30) Foreign Application Priority Data

Sep. 11, 2007 (FR) ...................................... 07 57480

(51) Int. Cl.
*A61Q 5/10* (2006.01)
*C07D 215/36* (2006.01)
(52) U.S. Cl. ............. 8/405; 8/407; 8/409; 8/437; 8/568; 8/587; 8/662; 546/171
(58) Field of Classification Search .............. 8/405, 407, 8/409, 437, 568, 587, 662; 546/171
See application file for complete search history.

(56) References Cited

U.S. PATENT DOCUMENTS

| 2,864,813 | A | 12/1958 | Bossard et al. |
| 2,904,385 | A | 9/1959 | Charle et al. |
| 5,034,014 | A | 7/1991 | Wenke |
| 7,247,713 | B2 | 7/2007 | David et al. |
| 7,488,354 | B2 | 2/2009 | Daubress et al. |
| 2006/0080791 | A1* | 4/2006 | Daubresse et al. ............... 8/405 |
| 2007/0130702 | A1 | 6/2007 | Andrean et al. |

FOREIGN PATENT DOCUMENTS

| DE | 1 544 506 | 4/1970 |
| DE | 198 42 071 | 3/2000 |
| DE | 101 48 844 | 10/2003 |
| EP | 1 133 975 | 9/2001 |
| EP | 1 407 756 | 4/2004 |
| EP | 1 647 580 A1 | 4/2006 |
| EP | 1 672 033 A2 | 6/2006 |
| FR | 2 787 708 | 6/2000 |
| GB | 1 094 309 | 12/1967 |
| GB | 2 183 237 | 6/1987 |
| JP | 54-008626 | 1/1979 |
| WO | WO 2005/097051 A2 | 10/2005 |
| WO | WO 2006/131163 | 12/2006 |
| WO | WO 2006/134043 | 12/2006 |

OTHER PUBLICATIONS

STIC Search Report dated Nov. 9, 2010.*
International Search Report for PCT/EP2008/061885, dated Oct. 22, 2009.
Copending U.S. Appl. No. 12/679,246, filed Mar. 19, 2010.
Copending U.S. Appl. No. 12/679,665, filed Mar. 23, 2010.
International Search Report for PCT/EP2008/062478, dated Dec. 3, 2009.
International Search Report for PCT/EP2008/062710, dated Dec. 12, 2008.
English language Abstract of DE 198 42 071, dated Mar. 16, 2000.
English language Abstract of DE 101 48 844, dated Apr. 10, 2003.
English language Abstract for JP 54-008626, dated Dec. 23, 1979.
Imahori, H. et al., "Photoinduced Electron Transfer at a Gold Electrode Modified with a Self-Assembled Monolayer of Fullerene," Chem. Commun. vol. 6, pp. 557-558 (1999).
Klepp, J. et al., "Nature of Coenzyme Binding by Glyceraldehyde-3-phophate Dehydrogenase: C NMR Studies with Oxidized [4-13C]Nicotinamide Adenine Dinucleotide," J. Am. Chem. Soc., vol. 111, No. 12, pp. 4440-4447 (1989).
Kniess, T. et al., "Nicotinamide-Substituted Complexes as Redox Markers," J. Labelled. CPD. Radiopharm., vol. XLI, pp. 605-614 (1998).

* cited by examiner

*Primary Examiner* — Eisa B Elhilo
(74) *Attorney, Agent, or Firm* — Finnegan, Henderson, Farabow, Garrett & Dunner

(57) ABSTRACT

The present invention relates to thiol/disulphide azo quinolinium compounds for dyeing keratin fibres. The invention relates to a dye composition comprising a particular thiol/disulphide azo quinolinium chromophore-containing thiol or disulphide dye, and to a process for dyeing keratin fibres such as the hair, using said composition. It similarly relates to novel particular thiol/disulphide azo quinolinium chromophore-containing dyes and to the uses thereof in dyeing keratin fibres. The dyeing process according to the invention makes it possible to dye keratin fibres without damaging them, in a manner which is particularly persistent with respect to shampooing operations and common attacks. Moreover, the novel dyes according to the invention extend the colour range to violets and blues. This process also makes it possible to dye bleached keratin fibres in a strong and chromatic manner.

15 Claims, No Drawings

AZO QUINOLINIUM COMPOUNDS COMPRISING A DISULPHIDE/THIOL UNIT, COMPOSITIONS CONTAINING SAME, PROCESS FOR DYEING KERATIN FIBRES AND DEVICE

CROSS REFERENCE TO RELATED APPLICATIONS

This application is a national phase application based on PCT/EP2008/061885, filed Sep. 8, 2008, which claims the priority of French Patent Application No. 0757480, filed Sep. 11, 2007, and claims the benefit of U.S. Provisional Application Ser. No. 60/960,190, filed Sep. 19, 2007, the content of all of which is incorporated herein by reference.

The present invention relates to thiol/disulphide azo quinolinium compounds for dyeing keratin fibres.

It is known practice to dye keratin fibres, and in particular human keratin fibres such as the hair, with dye compositions containing direct dyes. These compounds are coloured or colouring molecules which have an affinity for the fibres. It is known practice, for example, to use direct dyes of the nitrobenzene type, anthraquinone dyes, nitropyridine dyes, or dyes of the azo, xanthene, acridine, azine or triarylmethane type.

These dyes are normally applied to the fibres, optionally in the presence of an oxidizing agent, if it is desired to obtain a simultaneous lightening effect on the fibres. Once the leave-on time has elapsed, the fibres are rinsed, optionally washed and dried.

The colourings which result from the use of direct dyes are temporary or semi-permanent colourings since the nature of the interactions which bind the direct dyes to the keratin fibre, and their desorption from the surface and/or from the core of the fibre, are responsible for their weak dyeing power and their relatively poor resistance to washing and perspiration.

In order to increase the fastness of direct colourings, it is known practice to use disulphide dyes. For example, document WO 2006/136617 describes a mixture of several disulphide dyes with chestnut/brown shades on keratin fibres. However, some disulphide dyes have performance levels that are insufficient in particular in terms of selectivity, uptake, stability or resistance to outside attacks such as bad weather, shampooing operations, light or sweat, which brings about a change in colour over time. Colour change is a particularly embarrassing problem when it occurs after shampooing and/or exposure to light.

The aim of the present invention is therefore to provide disulphide or thiol dyes which do not have the drawbacks of existing direct dyes. In particular, one of the aims of the present invention is to provide dyes which make it possible to obtain natural shades which are resistant to outside attacks and which do not change colour over time.

This aim is achieved with the present invention, a subject of which is a process for dyeing keratin materials, in particular human keratin materials such as the hair, which comprises applying, to the keratin materials, a dye composition comprising, in a suitable cosmetic medium, at least one disulphide or thiol azo quinolinium dye of formula (I) or (II) below:

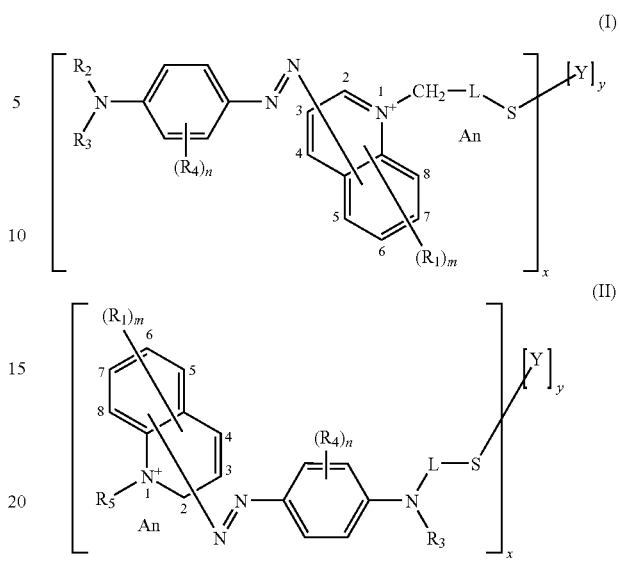

and also the addition salts thereof with an organic or mineral acid, and the solvates, hydrates, tautomers and optical and geometrical isomers thereof;

in which formulae (I) and (II):

L represents an optionally substituted $C_1$-$C_{20}$, particularly $C_1$-$C_{10}$, divalent hydrocarbon-based chain optionally interrupted with one or more divalent groups or combinations thereof, it being understood that two divalent groups or combinations thereof are separated by a $C_1$-$C_6$ divalent hydrocarbon-based chain, in particular alkylene, said divalent groups being chosen from:

i) —N(R)—; —N$^+$(R)(R$^\circ$)—, An$^-$; —O—, —S—, —C(O)—, with R representing a group chosen from $C_1$-$C_4$ alkyl, $C_2$-$C_6$ (poly)hydroxyalkyl, alkoxy-($C_1$-$C_6$) alkyl, aryl such as phenyl, aryl($C_1$-$C_6$)alkyl such as benzyl, ($C_1$-$C_4$)alkylcarbonylamino($C_1$-$C_6$)alkyl, amino ($C_1$-$C_4$)alkyl, the amine of which is substituted with one or more $C_1$-$C_4$ alkyl radicals, which may be identical or different, ($C_1$-$C_6$)alkylcarbonyl and ($C_1$-$C_4$)alkylcarbonylamino; and R$^\circ$ representing a hydrogen atom or R;

ii) a cationic heterocycle or cationic heteroaryl Het$^+$, An$^-$, with An$^-$ as previously defined and Het$^+$ representing a saturated or unsaturated, cationic heterocycle comprising from 5 to 10 members, or a cationic heteroaryl comprising from 5 to 10 members, such as imidazolium, piperazinium, benzimidazolium or pyrazolium;

iii) a noncationic heterocycle comprising from 5 to 10 members, such as piperazinyl, and iv) an optionally substituted (hetero)aryl such as optionally substituted 1,3,5-triazine;

with L comprising no diazo, hydrazino, aminooxy, nitro, nitroso or peroxide group;

$R_1$ and $R_4$, independently of one another, represent:
a $C_1$-$C_4$ alkyl group;
a hydroxyl group;
a $C_1$-$C_4$ alkoxy group;
a $C_2$-$C_4$ (poly)hydroxyalkoxy group;
an alkoxycarbonyl group ($R_a$O—C(O)—) in which $R_a$ represents a $C_1$-$C_4$ alkyl radical;
an alkylcarbonyloxy group ($R_a$C(O)—O—) in which $R_a$ represents a $C_1$-$C_4$ alkyl radical;
an amino group optionally substituted with one or more $C_1$-$C_4$ alkyl radicals, which may be identical or different, optionally bearing at least one hydroxyl group, it being possible for the two alkyl radicals to optionally form, with the nitrogen atom to which they are attached, a substituted or unsubstituted 5- or 6-membered heterocycle optionally bearing another heteroatom identical to or different from nitrogen, for example oxygen;

an alkylcarbonylamino group ($R_aC(O)-NR'_a-$) in which $R_a$ represents a $C_1$-$C_4$ alkyl radical and $R'_a$ represents a hydrogen atom or a $C_1$-$C_4$ alkyl radical;

a (di)(alkyl)aminocarbonyl group (($R_a$)$_2$N—C(O)) in which the $R_a$ radicals independently of one another, and which may be identical or different, represent a hydrogen atom or a $C_1$-$C_4$ alkyl radical;

a ureido group (($R_a$)$_2$N—CO—NR$_b$—) in which the $R_a$ and $R_b$ radicals, independently of one another, represent a hydrogen atom or a $C_1$-$C_4$ alkyl radical;

a guanidinium group (($R_a$)$_2$N—C(=NH$_2^+$)—NR$_b$—) in which the $R_a$ and $R_b$ radicals, independently of one another, represent a hydrogen atom or a $C_1$-$C_4$ alkyl radical;

a halogen atom, preferably chlorine, fluorine or bromine;

or else two adjacent $R_4$ radicals can form, with the carbon atoms to which they are attached, a condensed, aromatic 6-membered ring optionally substituted with one or more groups, which may be identical or different, chosen from hydroxyl, $C_1$-$C_4$ alkyl, hydroxycarbonyl (HO(O)C—), alkoxycarbonyl ($R_a$O(O)C—) in which $R_a$ represents a $C_1$-$C_4$ alkyl group, (alkyl)sulphonylamino ($R_aS(O)_2NR_b$) in which $R_a$ represents a $C_1$-$C_4$ alkyl and $R_b$ represents a hydrogen atom or a $C_1$-$C_4$ alkyl group; $C_1$-$C_4$ alkoxy; amino optionally substituted with one or two $C_1$-$C_4$ alkyl groups, which may be identical or different, and optionally bearing at least one hydroxyl or methylcarbonylamino group, it being possible for the two alkyl groups to optionally form, with the nitrogen atom to which they are attached, a 5- or 6-membered heterocycle optionally bearing another heteroatom identical to or different from nitrogen, for example oxygen;

$R_2$ and $R_3$, independently of one another, represent:
a hydrogen atom;
an optionally substituted $C_1$-$C_6$ alkyl group such as methyl;
an optionally substituted aryl group such as phenyl;
an optionally substituted heteroaryl group such as pyridyl;
an optionally substituted aryl($C_1$-$C_6$)alkyl group such as benzyl;
an optionally substituted heteroaryl($C_1$-$C_6$)alkyl group such as pyridinylmethyl;
a cycloalkyl($C_1$-$C_6$)alkyl group such as cyclohexylmethyl;
a heterocycloalkyl($C_1$-$C_6$)alkyl group such as piperidinylmethyl;
or else $R_3$, with the nitrogen atom which bears it, and $R_4$, with the carbon atom which bears it, can optionally together form a 5-, 6- or 7-membered heterocycle; this heterocycle and the aromatic ring attached to the azo group are then condensed; the heterocycle may be saturated or unsaturated, and optionally interrupted with a heteroatom, such as pyrrolidine, piperidine, homopiperidine, piperazine, homopiperazine or morpholine;

or else two contiguous $R_2$ groups, when n is 2, form, together with the carbon atom which bears them, a benzo group;

or else $R_2$ and $R_3$ of formula (I) form, together with the nitrogen atom which bears them, a 5-, 6- or 7-membered heterocycle, such as pyrrolidine, piperidine, homopiperidine, piperazine, homopiperazine or morpholine;

$R_5$ is directly attached to the quaternized nitrogen atom by means of a carbon atom and represents:
an optionally substituted $C_1$-$C_6$ alkyl group such as methyl;
an optionally substituted aryl group such as phenyl;
an optionally substituted heteroaryl group such as pyridyl;
an optionally substituted aryl($C_1$-$C_6$)alkyl group such as benzyl;
an optionally substituted heteroaryl($C_1$-$C_6$)alkyl group such as pyridinylmethyl;
a cycloalkyl($C_1$-$C_6$)alkyl group such as cyclohexylmethyl;
a heterocycloalkyl($C_1$-$C_6$)alkyl group such as piperidinylmethyl;

Y represents: i) a hydrogen atom; ii) an alkali metal; iii) an alkaline earth metal; iv) an ammonium group: $N^+R^\alpha R^\beta R^\gamma R^\delta$ or a phosphonium group: $P^+R^\alpha R^\beta R^\gamma R^\delta$, with $R^\alpha$, $R^\beta$, $R^\gamma$ and $R^\delta$, which may be identical or different, representing a hydrogen atom or a ($C_1$-$C_4$)alkyl group; or v) a thiol-function-protecting group;

An represents an anionic counterion;
m represents an integer between 0 and 6 inclusive;
n represents an integer between 0 and 4 inclusive;
x represents 1 or 2;
y represents 0 or 1;

it being understood that:
if x is 1, then y is 1 and that if x is 2, then y is zero;
the electroneutrality of the compounds of formulae (I) and (II) being ensured by one or more cosmetically acceptable anionic counterions An, which may or may not be identical.

Another subject of the invention is a dye composition for dyeing keratin fibres such as hair, comprising, in a cosmetic medium, at least one disulphide or thiol azo quinolinium dye of formula (I) or (II) as defined above, and optionally a reducing agent.

A subject of the invention is also a multicompartment device for dyeing keratin fibres, such as the hair, comprising, in one compartment, the composition according to the invention as defined above, in a second compartment, a reducing agent, and optionally, in a third compartment, an oxidizing agent.

Another subject of the invention concerns the disulphide or thiol azo quinolinium compounds of formulae (I) and (II) as defined above.

The dyeing process according to the invention makes it possible to dye keratin fibres without damaging them, in a manner which is persistent with respect to shampooing operations, common attacks such as sunlight or perspiration, and hair treatments.

This process also makes it possible to dye keratin fibres in a strong, nonselective, homogeneous and chromatic manner. Using a mixture with other dyes of different colours, this process also makes it possible to dye keratin fibres in natural shades such as browns and blacks without any notable colour change being observed over time.

Moreover, the novel dyes according to the invention have better chemical stability. These dyes are more soluble and stable than the prior art dyes in conventional cosmetic formulations containing in particular basified water and organic solvents. Mention may, for example, be made of $C_1$-$C_4$ lower alkanols such as ethanol and isopropanol, polyols and polyol ethers such as 2-butoxyethanol, propylene glycol, propylene glycol monomethyl ether, diethylene glycol monoethyl ether and diethylene glycol monomethyl ether, and also aromatic alcohols such as benzyl alcohol or phenoxyethanol, and mixtures thereof.

For the purpose of the present invention, and unless otherwise indicated:
- an "alkyl radical" is a linear or branched, $C_1$-$C_{16}$, preferably $C_1$-$C_6$, hydrocarbon-based radical;
- an "alkyl radical" or the "alkyl" part of a radical is said to be 'substituted' when it comprises at least one substituent chosen from the groups:
  - hydroxyl,
  - $C_1$-$C_4$ alkoxy,
  - $C_2$-$C_4$ (poly)hydroxyalkoxy,
  - amino, amino substituted with one or more $C_1$-$C_4$ alkyl groups, which may be identical or different, optionally bearing at least one hydroxyl group, it being possible for said alkyl radicals to form, with the nitrogen atom to which they are attached, a 5- or 6-membered heterocycle optionally comprising at least one other heteroatom which may or may not be different from nitrogen;
- an "aryl" or "heteroaryl radical", the "aryl" or "heteroaryl" part of a radical or the "arylene" or "heteroarylene" part is said to be 'substituted' when it comprises at least one substituent borne by a carbon atom, chosen from:
  - a $C_1$-$C_{16}$, preferably $C_1$-$C_8$, alkyl radical optionally substituted with one or more radicals chosen from the radicals hydroxyl, $C_1$-$C_2$ alkoxy, $C_2$-$C_4$ (poly)hydroxyalkoxy, acylamino, amino substituted with two $C_1$-$C_4$ alkyl radicals, which may be identical or different, optionally bearing at least one hydroxyl group, or it being possible for the two radicals to form, with the nitrogen atom to which they are attached, a 5- or 7-membered, preferably 5- or 6-membered, heterocycle optionally comprising another heteroatom identical to or different from nitrogen;
  - a halogen atom such as chlorine, fluorine or bromine;
  - a hydroxyl group;
  - a $C_1$-$C_2$ alkoxy radical;
  - a $C_1$-$C_4$ alkylthio;
  - a $C_2$-$C_4$ (poly)hydroxyalkoxy radical;
  - an amino radical; an amino radical substituted with one or two $C_1$-$C_4$ alkyl radicals, which may be identical or different, optionally bearing at least one hydroxyl group, or an amino radical substituted with two optionally substituted $C_1$-$C_2$ alkyl radicals;
  - an acylamino radical (—NR—C(O)R') in which the R radical is a hydrogen atom or a $C_1$-$C_4$ alkyl radical optionally bearing at least one hydroxyl group, and the R' radical is a $C_1$-$C_2$ alkyl radical; a carbamoyl radical ($R_2$N—C(O)—) in which the R radicals, which may be identical or different, represent a hydrogen atom or a $C_1$-$C_4$ alkyl radical optionally bearing at least one hydroxyl group; an alkylsulphonylamino radical (R'S(O)$_2$—NR—) in which the R radical represents a hydrogen atom or a $C_1$-$C_4$ alkyl radical optionally bearing at least one hydroxyl group, and the R' radical represents a $C_1$-$C_4$ alkyl radical or a phenyl radical; an aminosulphonyl radical ($R_2$N—S(O)$_2$—) in which the R radicals, which may be identical or different, represent a hydrogen atom or a $C_1$-$C_4$ alkyl radical optionally bearing at least one hydroxyl group;
- when an aryl($C_1$-$C_6$)alkyl; heteroaryl($C_1$-$C_6$)alkyl; cycloalkyl($C_1$-$C_6$)alkyl or heterocycloalkyl($C_1$-$C_6$) alkyl radical is said to be substituted, it is the aryl, heteroaryl, cycloalkyl or heterocycloalkyl part which is substituted;
- the cyclic or heterocyclic part of a nonaromatic radical is said to be substituted when it comprises at least one substituent borne by a carbon atom, chosen from the groups:
  - hydroxyl;
  - $C_1$-$C_4$ alkoxy, $C_2$-$C_4$ (poly)hydroxyalkoxy;
  - $C_1$-$C_4$ alkylthio;
  - alkylcarbonylamino (RC(O)—NR'—) in which the R' radical is a hydrogen atom or a $C_1$-$C_4$ alkyl radical optionally bearing at least one hydroxyl group, and the R radical is a $C_1$-$C_2$ alkyl radical or an amino radical substituted with two $C_1$-$C_4$ alkyl groups, which may be identical or different, optionally bearing at least one hydroxyl group, it being possible for said alkyl radicals to form, with the nitrogen atom to which they are attached, a 5- or 6-membered heterocycle optionally comprising at least one other heteroatom which may or may not be different from nitrogen;
- when a ring does not bear the maximum number of substituents, then the unsubstituted position(s) bear(s) a hydrogen atom;
- an "aryl" radical represents a condensed or noncondensed, monocyclic or polycyclic carbon-based group containing from 6 to 22 carbon atoms, and at least one ring of which is aromatic; preferably, the aryl radical is a phenyl, biphenyl, naphthyl, indenyl, anthracenyl or tetrahydronaphthyl;
- a "heteroaryl radical" represents an optionally cationic, condensed or noncondensed, monocyclic or polycyclic group comprising from 5 to 22 members, and from 1 to 6 heteroatoms chosen from nitrogen, oxygen, sulphur and selenium atoms, and at least one ring of which is aromatic; preferably, a heteroaryl radical is chosen from acridinyl, benzimidazolyl, benzobistriazolyl, benzopyrazolyl, benzopyridazinyl, benzoquinolyl, benzothiazolyl, benzotriazolyl, benzoxazolyl, pyridinyl, tetrazolyl, dihydrothiazolyl, imidazopyridinyl, imidazolyl, indolyl, isoquinolyl, naphthoimidazolyl, naphthooxazolyl, naphthopyrazolyl, oxadiazolyl, oxazolyl, oxazolopyridyl, phenazinyl, phenooxazolyl, pyrazinyl, pyrazolyl, pyrilyl, pyrazoyltriazyl, pyridyl, pyridinoimidazolyl, pyrrolyl, quinolyl, tetrazolyl, thiadiazolyl, thiazolyl, thiazolopyridinyl, thiazoylimidazolyl, thiopyrylyl, triazolyl, xanthylyl and its ammonium salt;
- a "cyclic" or "cycloalkyl radical" is a condensed or noncondensed, monocyclic or polycyclic, nonaromatic cycloalkyl radical containing from 5 to 22 carbon atoms, which may comprise one or more unsaturations; in particular, the cyclic radical is a cyclohexyl;
- a "heterocyclic radical or heterocycle" is a condensed or noncondensed, monocyclic or polycyclic, nonaromatic radical containing from 5 to 22 members, comprising from 1 to 6 heteroatoms chosen from nitrogen, oxygen and sulphur atoms;
- an "alkylene radical" is a $C_1$-$C_{20}$ linear or branched, divalent hydrocarbon-based chain optionally substituted with the same substituents as those of an optionally substituted alkyl group or with a carboxyl group; in particular, the alkylene chain is not substituted, such as methylene, ethylene or propylene;

an "alkenylene radical" is a $C_2$-$C_{20}$ linear or branched, divalent hydrocarbon-based chain comprising from one to three unsaturations, which may or may not be conjugated, optionally substituted with the same groups as those of the alkylene radical;

an "arylene" or "heteroarylene radical" is an aryl or heteroaryl group as defined above, which is divalent, i.e. two parts of the aryl or heteroaryl radical form a linker arm in the molecule;

an "organic or mineral acid salt" is more particularly chosen from a salt derived i) from hydrochloric acid HCl, ii) from hydrobromic acid HBr, iii) from sulphuric acid $H_2SO_4$, iv) from alkylsulphonic acids: Alk-S(O)$_2$OH, such as methylsulphonic acid and ethylsulphonic acid; v) from arylsulphonic acids: Ar—S(O)$_2$OH, such as benzenesulphonic acid and toluenesulphonic acid; vi) from citric acid; vii) from succinic acid; viii) from tartaric acid; ix) from lactic acid; x) from alkoxysulphinic acids: Alk-O—S(O)OH, such as methoxysulphinic acid and ethoxysulphinic acid; xi) from aryloxysulphinic acids, such as tolueneoxysulphinic acid and phenoxysulphinic acid; xii) from phosphoric acid $H_3PO_4$; xiii) from acetic acid $CH_3C(O)OH$; xiv) from triflic acid $CF_3SO_3H$ and xv) from tetrafluoroboric acid $HBF_4$;

an "anionic counterion" is an anion or an anionic group associated with the cationic charge of the dye; more particularly, the anionic counterion is chosen from i) halides such as chloride or bromide; ii) nitrates; iii) sulphonates, among which are $C_1$-$C_6$ alkylsulphonates: Alk-S(O)$_2$O$^-$ such as methylsulphonate or mesylate and ethylsulphonate; iv) arylsulphonates: Ar—S(O)$_2$O$^-$ such as benzenesulphonate and toluenesulphonate or tosylate; v) citrate; vi) succinate; vii) tartrate; viii) lactate; ix) alkyl sulphates: Alk-O—S(O)O$^-$ such as methyl sulphate and ethyl sulphate; x) aryl sulphates: Ar—O—S(O)O$^-$ such as benzene sulphate and toluene sulphate; xi) alkoxy sulphates: Alk-O—S(O)$_2$O$^-$ such as methoxy sulphate and ethoxy sulphate; xii) aryloxy sulphates: Ar—O—S(O)$_2$O$^-$, xiii) phosphates; xiv) acetate; xv) triflate; xvi) borates such as tetrafluoroborate; and xvii) oxalates;

the "solvates" represent the hydrates and also the association with linear or branched $C_2$-$C_4$ alcohols such as ethanol, isopropanol or n-propanol.

The compounds of the invention of formulae (I) and (II), when x and y are 1, contain an SY function which may be in the covalent —S—Y form or ionic —S—Y+ form, depending on the nature of Y and on the pH of the medium.

As indicated above, a first subject of the invention comprises compounds corresponding to the above-mentioned formulae (I) and (II).

A specific embodiment concerns the thiol dyes of formulae (I) and (II) with x and y which are 1, and Y representing a hydrogen atom or an alkali metal. Advantageously, Y represents a hydrogen atom.

In accordance with another specific embodiment of the invention, in the abovementioned formulae (I) and (II), Y is a protecting group known to those skilled in the art, for instance those described in the books "*Protective Groups in Organic Synthesis*", T. W. Greene, John Willey & Sons ed., NY, 1981, pp. 193-217; "*Protecting Groups*", P. Kocienski, Thieme, 3rd edition, 2005, chap. 5.

In particular, when Y represents a thiol-function-protecting group, Y is chosen from the following radicals:

($C_1$-$C_4$)alkylcarbonyl;
($C_1$-$C_4$)alkylthiocarbonyl;
($C_1$-$C_4$)alkoxycarbonyl;
($C_1$-$C_4$)alkoxythiocarbonyl;
($C_1$-$C_4$)alkylthiothiocarbonyl;
(di)($C_1$-$C_4$) (alkyl)aminocarbonyl;
(di)($C_1$-$C_4$) (alkyl)aminothiocarbonyl;
arylcarbonyl such as phenylcarbonyl;
aryloxycarbonyl;
aryl($C_1$-$C_4$)alkoxycarbonyl;
(di)($C_1$-$C_4$) (alkyl)aminocarbonyl such as dimethylaminocarbonyl;
($C_1$-$C_4$) (alkyl)arylaminocarbonyl;
carboxyl;
$SO_3^-$; $M^+$ with $M^+$ representing an alkali metal such as sodium or potassium, or else An or An'$^-$ of formula (I) or (II) and $M^+$ are absent;
optionally substituted aryl such as phenyl, dibenzosuberyl or 1,3,5-cycloheptatrienyl;
optionally substituted heteroaryl; including, in particular, the cationic or noncationic heteroaryl radicals comprising from 1 to 4 heteroatoms below:
  i) 5-, 6- or 7-membered monocyclic radicals, such as furanyl or furyl, pyrrolyl or pyrryl, thiophenyl or thienyl, pyrazolyl, oxazolyl, oxazolium, isoxazolyl, isoxazolium, thiazolyl, thiazolium, isothiazolyl, isothiazolium, 1,2,4-triazolyl, 1,2,4-triazolium, 1,2,3-triazolyl, 1,2,3-triazolium, 1,2,4-oxazolyl, 1,2,4-oxazolium, 1,2,4-thiadiazolyl, 1,2,4-thiadiazolium, pyrylium, thiopyridyl, pyridinium, pyrimidinyl, pyrimidinium, pyrazinyl, pyrazinium, pyridazinyl, pyridazinium, triazinyl, triazinium, tetrazinyl, tetrazinium, azepine, azepinium, oxazepinyl, oxazepinium, thiepinyl, thiepinium, imidazolyl or imidazolium;
  ii) 8- to 11-membered bicyclic radicals, such as indolyl, indolinium, benzoimidazolyl, benzoimidazolium, benzoxazolyl, benzoxazolium, dihydrobenzoxazolinyl, benzothiazolyl, benzothiazolium, pyridoimidazolyl, pyridoimidazolium or thienocycloheptadienyl, these monocyclic or bicyclic groups being optionally substituted with one or more groups such as ($C_1$-$C_4$) alkyl, for instance methyl, or polyhalo($C_1$-$C_4$)alkyl, for instance trifluoromethyl;
optionally cationic, optionally substituted heterocycloalkyl, the heterocycloalkyl group representing in particular a saturated or partially saturated, 5-, 6- or 7-membered monocyclic group comprising from 1 to 4 heteroatoms chosen from oxygen, sulphur and nitrogen, such as di/tetrahydrofuranyl, di/tetrahydrothiophenyl, di/tetrahydropyrrolyl, di/tetrahydropyranyl, di/tetra-/hexahydrothiopyranyl, dihydropyridyl, piperazinyl, piperidinyl, tetramethylpiperidinyl, morpholinyl, di/tetra/hexahydroazepinyl, di/tetrahydropyrimidinyl, these groups being optionally substituted with one or more groups such as ($C_1$-$C_4$)alkyl, oxo or thioxo; or the heterocycle represents the following group:

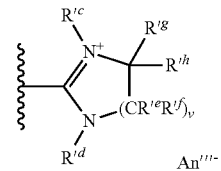

in which $R'^c$, $R'^d$, $R'^e$, $R'^f$, $R'^g$ and $R'^h$, which may be identical or different, represent a hydrogen atom or a ($C_1$-$C_4$)alkyl group, or else two groups $R'^g$ with $R'^h$, and/or $R'^e$ with $R'^f$ form an oxo or thioxo group, or else $R'^g$ with $R'^e$ together form a cycloalkyl; and v represents an integer between 1 and 3 inclusive; preferably, $R'^c$ to $R'^h$ represent a hydrogen atom; and $An'''^-$ represents a counterion;

—$C(NR'^cR'^d)$=$C^+R'^eR'^f$; $An''''^-$ with $R'^c$, $R'^d$, $R'^e$ and $R'^f$, which may be identical or different, representing a hydrogen atom or a ($C_1$-$C_4$)alkyl group; preferably, $R'^c$ to $R'^f$ represent a hydrogen atom; and $An''''^-$ represents a counterion;

—$C(NR'^cR'^d)$=$NR'^e$; with $R'^c$, $R'^d$ and $R'^e$ as defined above;

optionally substituted (di)aryl($C_1$-$C_4$)alkyl, such as 9-anthracenylmethyl, phenylmethyl or diphenylmethyl optionally substituted with one or more groups in particular chosen from ($C_1$-$C_4$)alkyl, ($C_1$-$C_4$)alkoxy, for instance methoxy, hydroxyl, alkylcarbonyl, and (di)($C_1$-$C_4$)(alkyl)amino, for instance dimethylamino;

optionally substituted (di)heteroaryl-($C_1$-$C_4$)alkyl; the heteroaryl group is in particular cationic or noncationic, and monocyclic, comprising 5 or 6 members and from 1 to 4 heteroatoms chosen from nitrogen, oxygen and sulphur, such as the groups pyrrolyl, furanyl, thiophenyl, pyridyl, pyridyl N-oxide such as 4-pyridyl N-oxide or 2-pyridyl N-oxide, pyrylium, pyridinium or triazinyl, optionally substituted with one or more groups such as alkyl, particularly methyl; advantageously, the (di)heteroaryl($C_1$-$C_4$)alkyl is (di)heteroarylmethyl or (di)heteroarylethyl;

$CR^1R^2R^3$ with $R^1$, $R^2$ and $R^3$, which may be identical or different, representing a halogen atom or a group chosen from:

($C_1$-$C_4$)alkyl;
($C_1$-$C_4$)alkoxy;
optionally substituted aryl, such as phenyl optionally substituted with one or more groups such as ($C_1$-$C_4$)alkyl, ($C_1$-$C_4$)alkoxy or hydroxyl;
optionally substituted heteroaryl, such as thiophenyl, furanyl, pyrrolyl, pyranyl or pyridyl, optionally substituted with a ($C_1$-$C_4$)alkyl group;
$P(Z^1)R'^1R'^2R'^3$ with $R'^1$ and $R'^2$, which may be identical or different, representing a hydroxyl, ($C_1$-$C_4$)alkoxy or alkyl group, $R'^3$ representing a hydroxyl or ($C_1$-$C_4$) alkoxy group, and $Z^1$ representing an oxygen or sulphur atom;

a sterically hindered cyclic group; and optionally substituted alkoxyalkyl, such as methoxymethyl (MOM), ethoxyethyl (EOM) and isobutoxymethyl.

According to a preferred variant of the invention, Y represents:

a hydrogen atom;
a $C_1$-$C_4$ alkylcarbonyl radical, preferably acetyl;
an imidazolium radical optionally substituted with one or more $C_1$-$C_4$ alkyl radicals;
a —$C(NR'^cR'^d)$=$NR'^e$ radical where $R'^c$, $R'^d$ and $R'^e$ are as defined above, preferably the group —C(=NH)NH$_4$;
a $C_1$-$C_4$ alkoxycarbonyl radical, preferably the group —CO$_2$Et;
an alkylpyridinium radical, preferably the methylpyridinium group, in particular 2-methylpyridinium.

The $R_1$ and $R_4$ radicals, independently of one another, more particularly represent:

a $C_1$-$C_4$ alkyl group;
a halogen atom such as chlorine, fluorine or bromine;
a hydroxyl group;

a $C_1$-$C_2$ alkoxy radical;
a $C_2$-$C_4$ (poly)hydroxyalkoxy radical;
an amino radical;
an amino radical substituted with one or two $C_1$-$C_4$ alkyl radicals, which may be identical or different, optionally bearing at least one hydroxyl or $C_1$-$C_4$ dialkylamino group, it being possible for the two alkyl radicals to optionally form, with the nitrogen atom to which they are attached, an optionally substituted, saturated or unsaturated, 5- or 6-membered heterocycle optionally bearing another heteroatom chosen from the nitrogen, oxygen or sulphur atom;
an alkylcarbonylamino radical (RC(O)—NR'—) in which the R radical represents a $C_1$-$C_4$ alkyl radical and the R' radical represents a hydrogen or a $C_1$-$C_4$ alkyl radical;
a carbamoyl radical ($R_2$N—C(O)—) in which the R radicals, which may be identical or different, represent a hydrogen atom or a $C_1$-$C_4$ alkyl radical optionally bearing at least one hydroxyl group;
an alkylsulphonylamino radical (R'S(O)$_2$—NR—) in which the R radical represents a hydrogen atom or a $C_1$-$C_4$ alkyl radical optionally bearing at least one hydroxyl group, and the R' radical represents a $C_1$-$C_4$ alkyl radical;
an aminosulphonyl radical ($R_2$N—S(O)$_2$—) in which the R radicals, which may be identical or different, represent a hydrogen atom or a $C_1$-$C_4$ alkyl radical optionally bearing at least one hydroxyl group;
a ureido radical ($R_2$N—C(O)—NR'—) in which the R and R' radicals, which may be identical or different, and independently of one another, represent a hydrogen atom or a $C_1$-$C_4$ alkyl radical.

More particularly, the $R_1$ and $R_4$ radicals, independently of one another, represent:

a $C_1$-$C_2$ alkyl radical;
an amino radical;
an amino radical substituted with one or two $C_1$-$C_3$ alkyl radicals, which may be identical or different, optionally bearing at least one hydroxyl group, it being possible for the two alkyl radicals to optionally form, with the nitrogen atom to which they are attached, an optionally substituted, saturated or unsaturated, 5- or 6-membered heterocycle optionally bearing another heteroatom identical to or different from nitrogen;
an alkylcarbonylamino radical (RC(O)—NR') in which the R radical represents a $C_1$-$C_2$ alkyl radical and the R' radical represents a hydrogen or a $C_1$-$C_4$ alkyl radical;
a carbamoyl radical ($R_2$N—C(O)—) in which the R radicals, which may be identical or different, represent a hydrogen atom or a $C_1$-$C_4$ alkyl radical optionally bearing at least one hydroxyl group;
a sulphonylamino radical;
a hydroxyl radical;
a $C_1$-$C_2$ alkoxy radical;
a chlorine atom.

Even more particularly, the $R_1$ and $R_4$ radicals, independently of one another, represent:

a $C_1$-$C_2$ alkyl radical;
a $C_1$-$C_2$ alkoxy radical;
a hydroxyl radical;
an amino radical substituted with one or two $C_1$-$C_2$ alkyl radicals, which may be identical or different, optionally bearing at least one hydroxyl group;
an alkylcarbonylamino radical (RC(O)—NR') in which the R radical represents a $C_1$-$C_2$ alkyl radical and the R' radical represents a hydrogen.

According to a preferred variant of the invention, the $R_1$ and $R_4$ radicals, independently of one another, represent:
- a methyl or ethyl radical;
- an amino, dimethylamino or bis(2-hydroxyethyl)-amino radical;
- a hydroxyl radical;
- an acetylamino radical.

As regards the position of the $R_1$ radical, when m is 1 and the azo group is in the 4-position, the $R_1$ group is preferably in the 2-position. When m is greater than or equal to 2, then the azo group is preferably in the 4-position, and the $R_1$ groups are in the 2-, 5-, 6- and 7-position. When m is 1 and the azo group is in the 2-position, then the $R_1$ group is preferably in the 4-position. When m is greater than or equal to 2, then the azo group is in the 2-position, and the $R_1$ groups are preferably in the 3-, 4-, 5-, 6- and 8-position.

As regards the position of $R_4$, when m is 1, the $R_4$ group is preferably in the ortho-position with respect to the azo group, except when the $R_4$ group forms a ring with the $R_3$ group, in which case the $R_4$ radical is in the meta-position with respect to the azo group.

When n is 2, then the $R_4$ radicals are both preferably in the ortho-position with respect to the azo group or one of the two groups is in the ortho-position with respect to the azo group and the other is in the meta-position with respect to the azo group. This $R_4$ radical in the meta-position may be preferentially in the ortho-position or in the para-position with respect to the other $R_4$ group.

In particular, m is zero or else m is 1 and $R_1$ represents a ($C_1$-$C_4$)alkyl group.

In particular, n is zero or else m is 2 and $R_1$ represents a methyl or methoxy group.

According to a second preferred variant of the invention, two $R_4$ radicals borne by adjacent carbon atoms can form, together with the carbon atom to which each is attached, an optionally aromatic condensed ring such as benzo, optionally substituted preferably with a methyl radical; a hydroxyl radical; a methoxy radical; an amino radical; a methylamino radical; a dimethylamino radical; a pyrrolidine radical; or a sulphonylamino radical.

The $R_2$ and $R_3$ radicals, independently of one another, represent particularly:
- a hydrogen atom;
- an optionally substituted $C_1$-$C_6$ alkyl group;
- $R_2$ and $R_3$ of formula (I) form, together with the nitrogen atom which bears them, a 5-, 6- or 7-membered heterocycle such as pyrrolidine, piperidine, homopiperidine, piperazine, homopiperazine or morpholine.

More particularly, the $R_2$ and $R_3$ radicals, independently of one another, represent:
- a hydrogen atom;
- a $C_1$-$C_4$ alkyl radical optionally substituted with one or more radicals chosen from the radicals:
  i) hydroxyl;
  ii) amino substituted with two $C_1$-$C_2$ alkyl radicals, which may be identical or different, optionally bearing at least one group:
    hydroxyl;
    a $C_1$-$C_2$ alkoxy radical;
    an amino radical;
    an amino radical substituted with one or two $C_1$-$C_3$ alkyl radicals, which may be identical or different, optionally bearing at least one hydroxyl group.

According to a preferred variant of the invention, the $R_2$ and $R_3$ radicals, independently of one another, represent:
- a hydrogen atom; or a methyl, ethyl, 2-hydroxyethyl or 2-hydroxypropyl radical.

According to a second preferred variant of the invention, for the compounds of formula (I) the $R_2$ and $R_3$ radicals can form, together with the nitrogen atom to which they are attached, a saturated ring comprising from 5 to 7 members, such as pyrrolidine, piperidine, piperazine or morpholine rings.

Preferably, $R_2$ and $R_3$ form, together with the nitrogen atom to which they are attached, a pyrrolidine ring.

As regards the $R_5$ radical, it represents in particular a $C_1$-$C_6$ alkyl radical; a $C_2$-$C_6$ monohydroxyalkyl radical; a $C_2$-$C_6$ polyhydroxyalkyl radical; a ($C_1$-$C_6$)alkoxy-($C_2$-$C_6$)alkyl radical; an optionally substituted arylalkyl radical, such as benzyl; a $C_2$-$C_6$ amidoalkyl radical; a $C_2$-$C_6$ aminoalkyl radical of which the amine is substituted with two optionally substituted $C_1$-$C_4$ alkyl radicals which may be identical or different. Furthermore, the $R_1$ radical is such that the atom directly linked to the nitrogen atom is a carbon atom.

Preferably, $R_5$ represents a $C_1$-$C_4$ alkyl radical; a $C_2$-$C_4$ monohydroxyalkyl radical; a $C_2$-$C_4$ polyhydroxyalkyl radical; a ($C_1$-$C_4$)alkoxy($C_2$-$C_4$)alkyl radical; a benzyl radical; a $C_1$-$C_4$ aminoalkyl radical; or a $C_1$-$C_4$ aminoalkyl radical of which the amine is substituted with 4 two $C_1$-$C_2$ identical alkyl radicals 4.

Preferably, $R_5$ represents a methyl or ethyl radical or a 2-hydroxyethyl radical.

According to a specific embodiment of the invention, the linker arm L is a chain which links the chromophore with the disulphide or the thiol.

Another specific aspect of the invention concerns the dyes of formula (I) or (I') which have a noncationic linker arm L. According to this variant, the noncationic divalent linker arm L represents:
- an optionally substituted $C_1$-$C_{20}$, preferably $C_1$-$C_{10}$, alkyl radical optionally interrupted with an aromatic or non-aromatic, saturated or unsaturated (hetero)cycle comprising from 3 to 7 members, which is optionally substituted and optionally condensed; said alkyl radical being optionally interrupted with one or more heteroatoms or groups comprising at least one heteroatom, preferably oxygen or nitrogen, such as —C(O)—, or combinations thereof.

L more particularly represents:
- an alkylene group —$C_nH_{2n}$— in which n is an integer from 1 to 20, preferably from 1 to 10, and even more preferably from 1 to 6;
- a —$C_pH_{2p}$—C(O)—NR—$C_sH_{2s}$— radical in which p and s, which may be identical or different, represent an integer between 1 and 6 inclusive, and R represents a hydrogen atom or a $C_1$-$C_4$ alkyl group, preferably p=1 to 4, s=1 to 4 and R=H;
- a -(hetero)arylene-J-($C_1$-$C_6$)alkylene- radical, with J representing a divalent group chosen from —O—, —S—, —N(R)—, —C(O)—N(R)— and —N(R)—C(O)—, R representing a hydrogen atom or a ($C_1$-$C_4$)alkyl group, preferably the alkylene is $C_1$-$C_4$.

The (hetero)arylene radicals are optionally substituted. The alkylene part is optionally interrupted with one or more heteroatoms chosen from oxygen and nitrogen, preferably a nitrogen atom.

The (hetero)arylene radicals are, for example, phenylene or naphthylene, phenanthrylene, triazinylene, pyrimidinylene, pyridinylene, pyridazinylene or quinoxalinylene.

According to this variant, L represents a -triazinylene($C_1$-$C_{10}$)alkylene group of which the triazinylene radical is optionally substituted. Even more preferably, L represents a group:

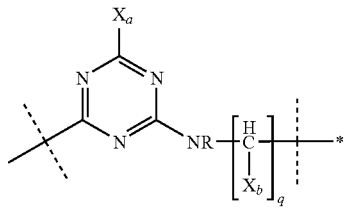

in which:
$X_a$ represents a halogen atom or a radical chosen from a hydroxyl, amino and a (di)($C_1$-$C_4$)alkylamino radical, the alkyl group(s) of which is (are) optionally substituted with one or more hydroxyl radicals;
$X_b$ represents a hydrogen atom or a ($C_1$-$C_4$)alkyl radical optionally substituted with one or more hydroxyl radicals;
R represents a hydrogen atom or a ($C_1$-$C_4$)alkyl radical, particularly a hydrogen atom;
q is equal to 1 or 2.

Another particular aspect of the invention concerns the dyes of formula (I) or (I') which have a cationic linker arm L. According to this variant, the cationic divalent linker arm L represents:
a $C_2$-$C_{20}$ alkyl radical bearing at least one cationic charge, optionally substituted and/or optionally interrupted with one or more aromatic or nonaromatic, saturated or unsaturated (hetero)cycles, which may be identical or different, comprising from 3 to 7 members and/or optionally interrupted with one or more heteroatoms or groups comprising at least one heteroatom or combinations thereof, for instance oxygen, nitrogen, a —C(O)— group or an —S(O)$_2$— group or combinations thereof; the linker arm L comprising no azo, nitro, nitroso or peroxo bond; it being understood that the linker arm L bears at least one cationic charge. According to this variant, the cationic linker arm L advantageously represents a $C_2$-$C_{20}$ alkyl radical:
1- interrupted with at least one group corresponding to formulae (a) and (b) below:

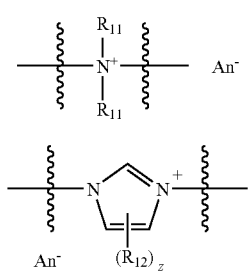

in which:
$R_{11}$, independently of one another, represent:
a linear or branched $C_1$-$C_8$ alkyl radical;
a $C_2$-$C_6$ (poly)hydroxyalkyl radical;
a ($C_1$-$C_6$)alkoxy($C_2$-$C_6$)alkyl radical;
an aryl radical such as phenyl which is optionally substituted;
an arylalkyl radical such as benzyl which is optionally substituted;
a $C_2$-$C_6$ aminocarbonylalkyl radical;
a $C_2$-$C_6$ aminoalkyl radical of which the amine is optionally substituted with one or two $C_1$-$C_4$ alkyl radicals which may be identical or different;
two $R_{11}$ radicals may form, together with the nitrogen atom to which they are attached, a saturated or unsaturated, optionally substituted, 5-, 6- or 7-membered ring;
$R_{12}$, which may be identical or different, represent:
a halogen atom chosen from bromine, chlorine or fluorine;
a $C_1$-$C_6$ alkyl radical;
a $C_2$-$C_6$ (poly)hydroxyalkyl radical;
a $C_1$-$C_6$ alkoxy radical;
a $C_1$-$C_4$ (di)alkylamino radical;
a hydroxycarbonyl radical;
a $C_1$-$C_6$ alkylcarbonyl radical;
an optionally substituted benzyl radical;
a phenyl radical optionally substituted with one or more radicals chosen from methyl, hydroxyl, amino and methoxy radicals;
An- represents an anionic counterion or a mixture of anionic counterions;
z is an integer between 1 and 3; if z<3, then the unsubstituted carbon atoms bear a hydrogen atom;
2- optionally interrupted with one or more heteroatoms or groups comprising at least one heteroatom or combinations thereof, chosen from oxygen, nitrogen and the —C(O)— group;
3- and optionally substituted with one or more radicals chosen from the radicals hydroxyl, $C_1$-$C_2$ alkoxy, $C_2$-$C_4$ (poly)hydroxyalkoxy, amino substituted with one or more linear or branched $C_1$-$C_2$ alkyl groups optionally bearing at least one hydroxyl group.

According to a specific embodiment of formula (a), $R_{11}$, separately, are preferably chosen from a $C_1$-$C_6$ alkyl radical, a $C_2$-$C_4$ (poly)hydroxyalkyl radical, a ($C_1$-$C_6$)alkoxy($C_2$-$C_4$) alkyl radical and a dimethylamino($C_2$-$C_6$)alkyl radical. Even more particularly, the $R_{11}$ radicals separately represent a methyl, ethyl, or 2-hydroxyethyl radical.

According to a specific embodiment of formula (b), $R_{12}$ represents a halogen atom chosen from chlorine and fluorine, a $C_1$-$C_6$ alkyl radical, a $C_1$-$C_4$ monohydroxyalkyl radical, a $C_1$-$C_4$ alkoxy radical, a hydroxycarbonyl radical, a ($C_1$-$C_6$) alkylthio radical or an amino radical disubstituted with a ($C_1$-$C_4$)alkyl radical.

According to an even more specific embodiment of formula (b), $R_{12}$ represents a chlorine atom, a methyl, an ethyl, a 2-hydroxyethyl, a methoxy, a hydroxycarbonyl or a dimethylamino.

According to another even more specific embodiment of formula (b), z is equal to 0.

When the linker arm L is cationic, L advantageously represents a $C_2$-$C_{10}$ alkyl radical interrupted with at least one group of formula (a) or (b) in which the $R_{11}$ and/or $R_{12}$ radicals, independently of one another, represent a linear or branched $C_1$-$C_4$ alkyl radical and An⁻ is an anionic counterion or a mixture. Even more preferably, L is a $C_2$-$C_{10}$ alkylene radical interrupted with a group of formula (a) in which the two $R_{11}$ radicals are identical and represent a $C_1$-$C_4$ alkyl radical, such as methyl.

By way of linker arm L, mention may also be made of the triazines described in WO 03/029359, the alkylenes mentioned in U.S. Pat. No. 5,708,151, and the -alkylenearylene-alkylenes- mentioned in U.S. Pat. No. 5,708,151.

A particular embodiment relates to disulphide dyes of formula (I) or (II) in which x=2 and y=0.

According to a preferred embodiment of the invention, the compounds correspond more particularly to the following formulae:

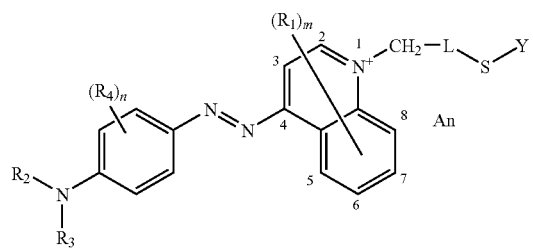
(Ia)

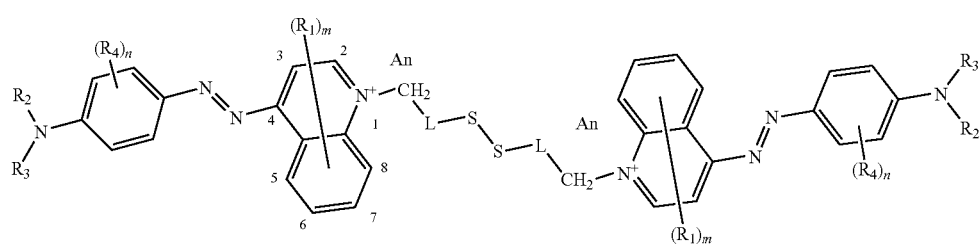
(Ib)

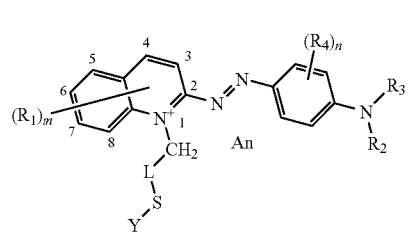
(Ic)

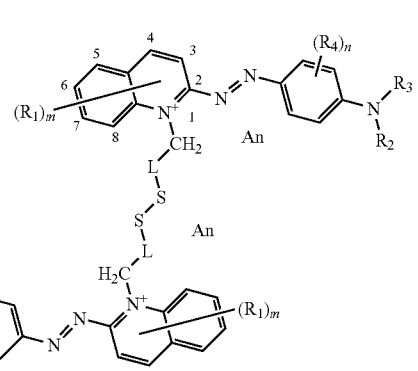
(Id)

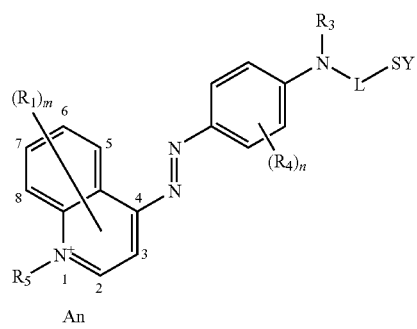
(IIa)

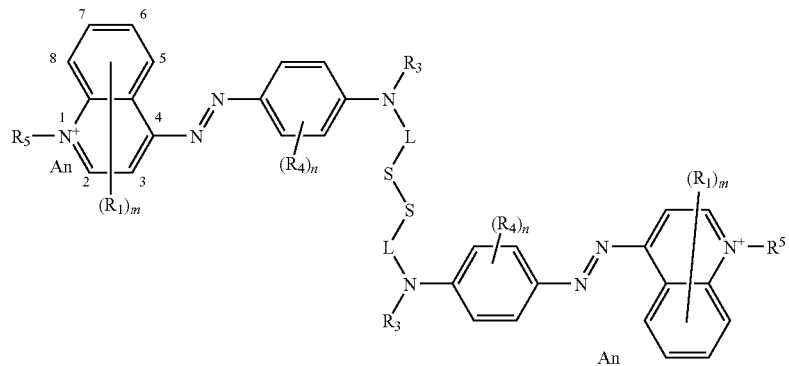
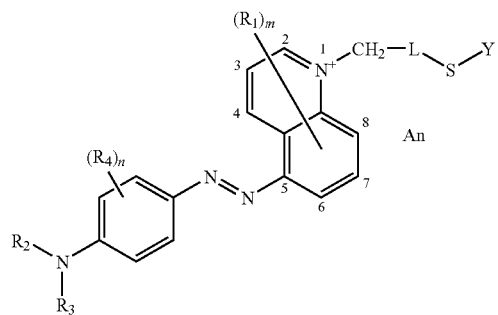
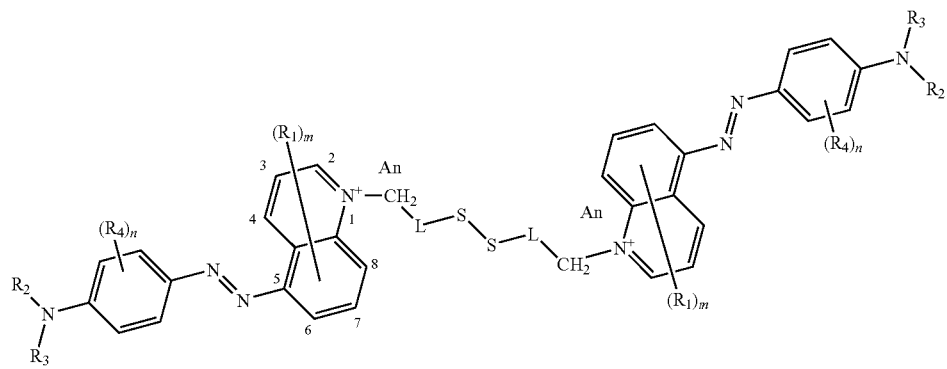
in which formulae, $R_1$, $R_2$, $R_3$, $R_4$, $R_5$, L, An, m and n have been defined above.
By way of example of a dye of formula (I) or (II), or of (Ia) to (If), (IIa) and (IIb), mention may be made of the following dyes:
1
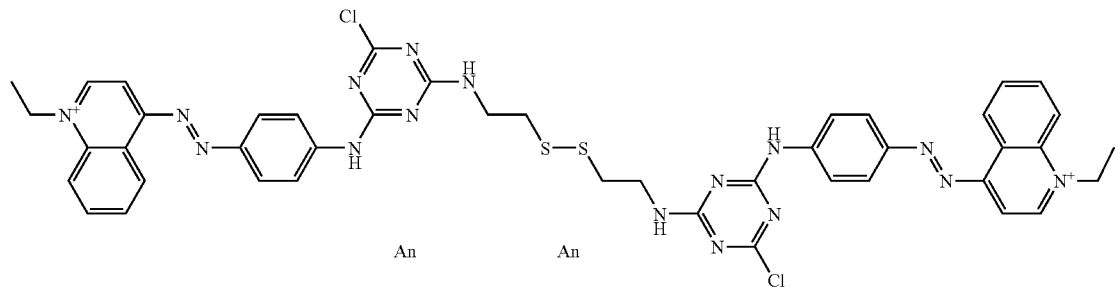

-continued
2
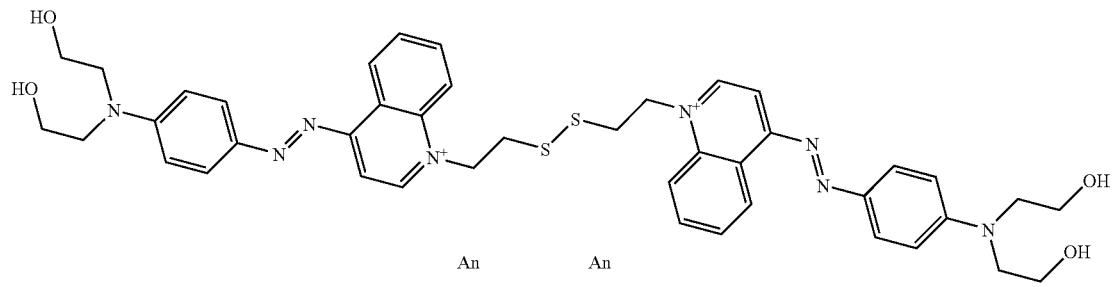
3
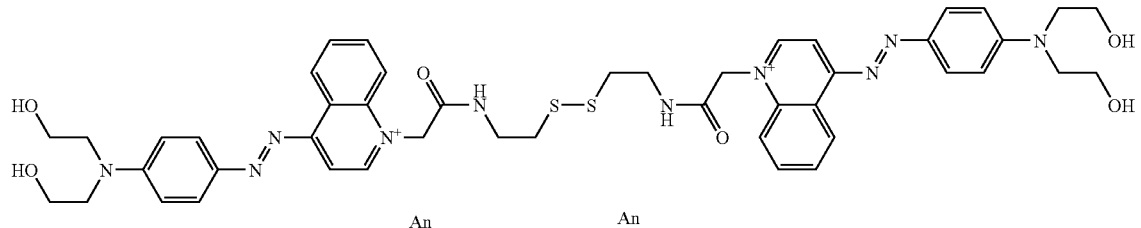
4
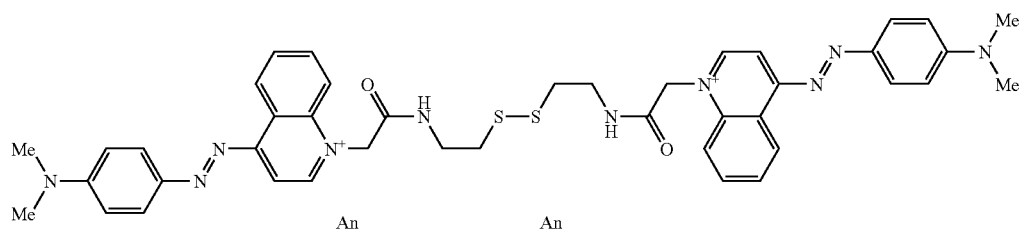
5
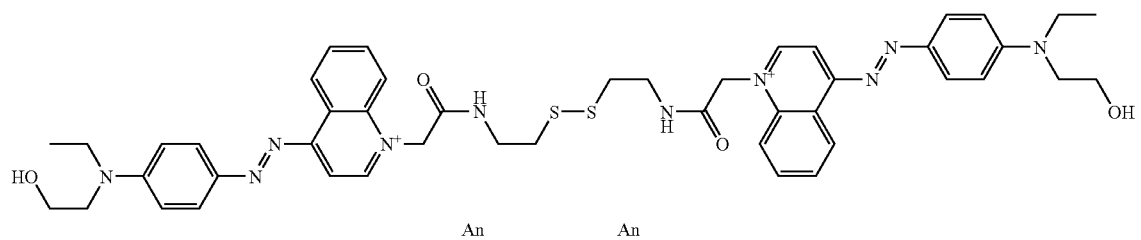
6
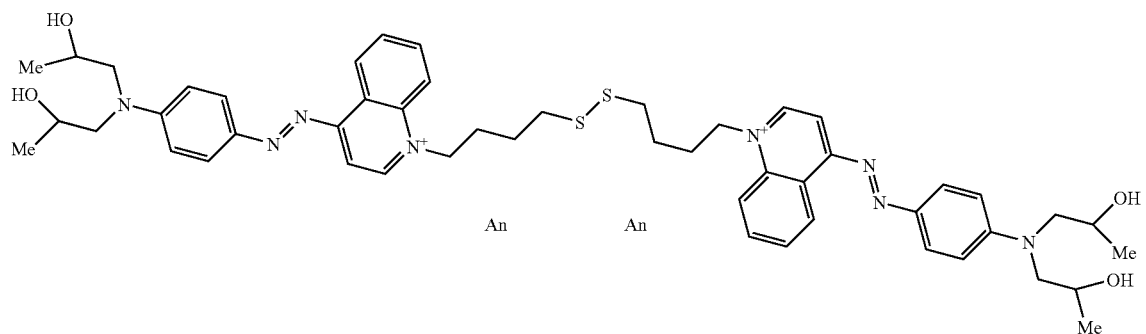

-continued
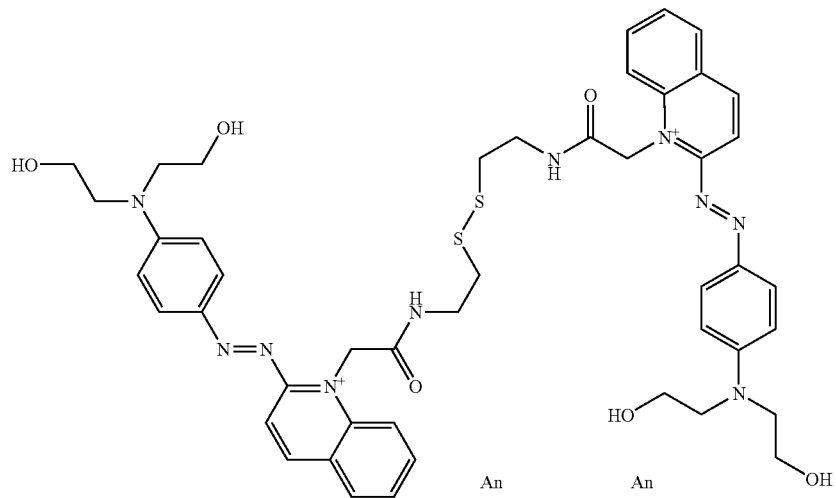
7
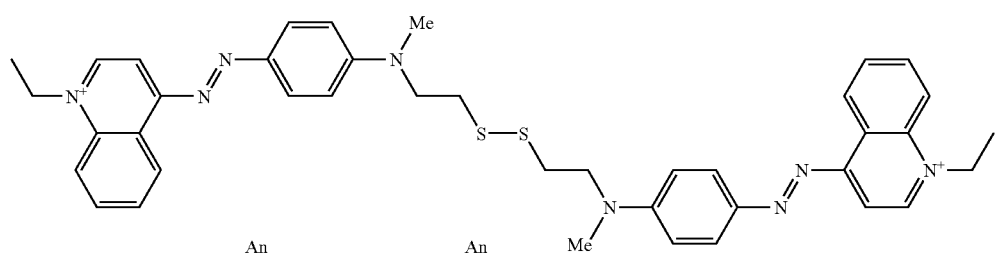
8
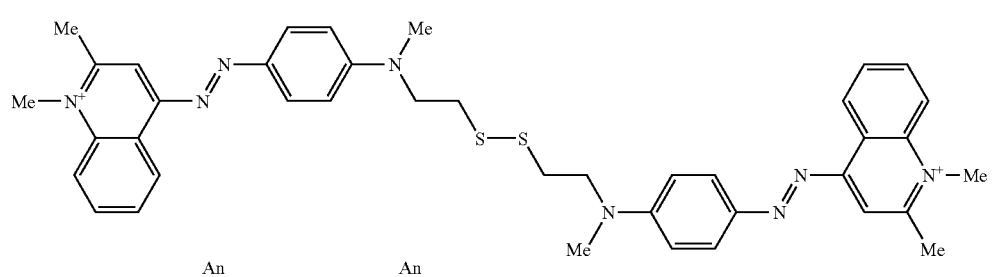
9
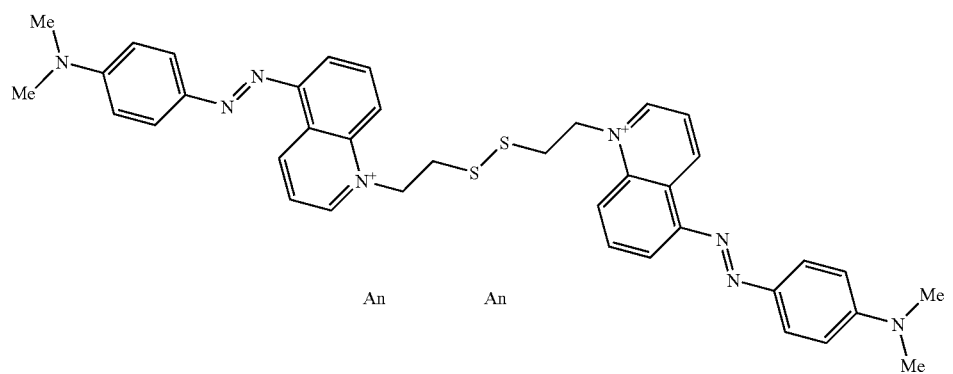
10

11
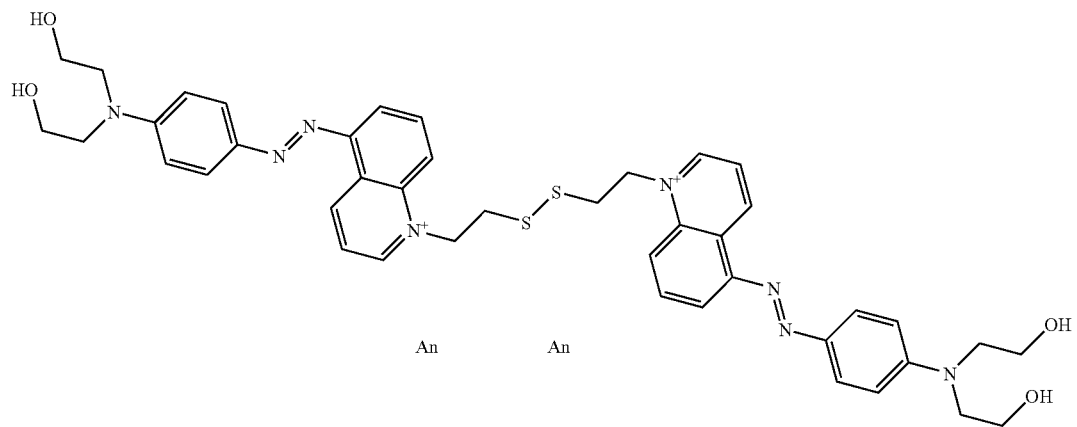
12
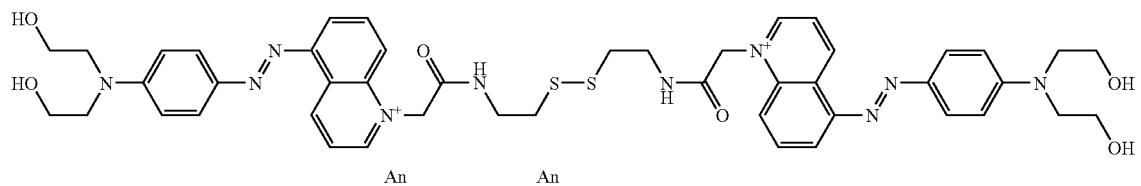
13
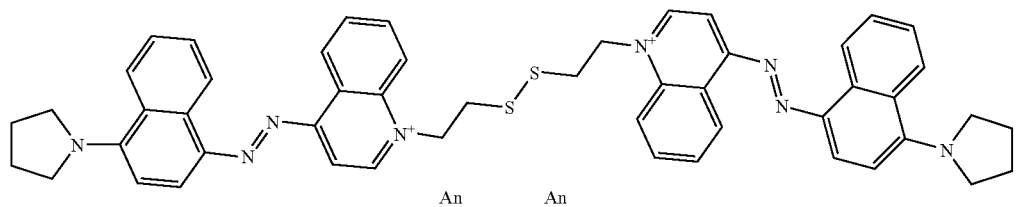
14
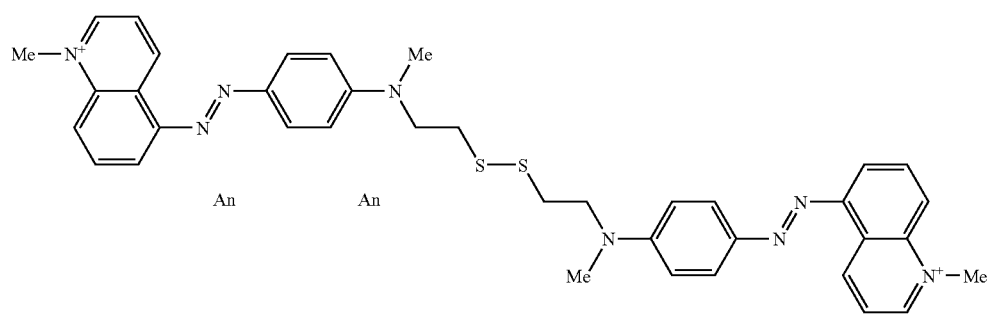
15
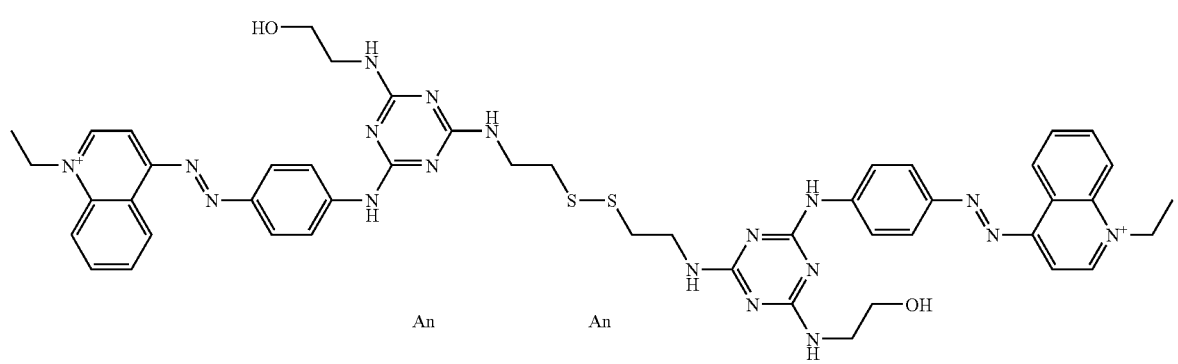

-continued
16
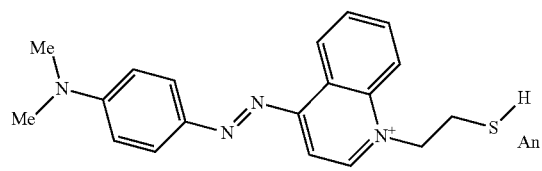
17
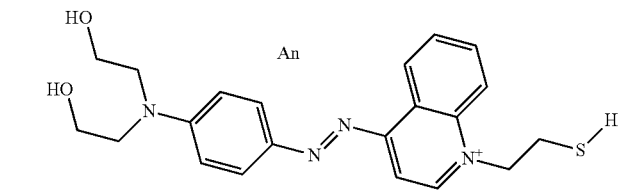
18
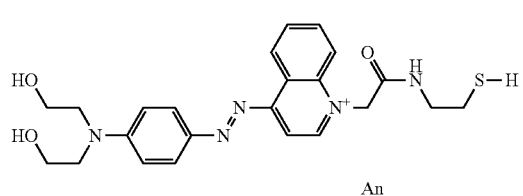
19
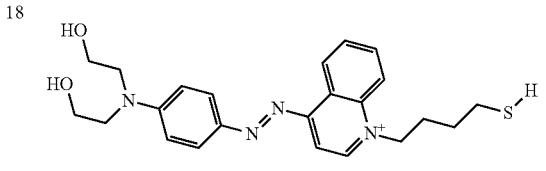
20
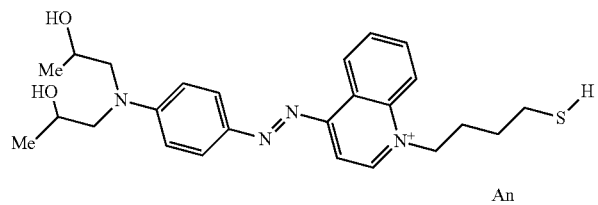
21
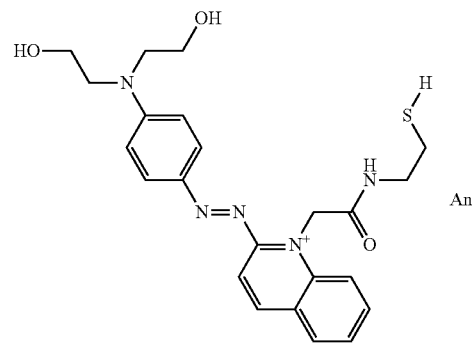
22
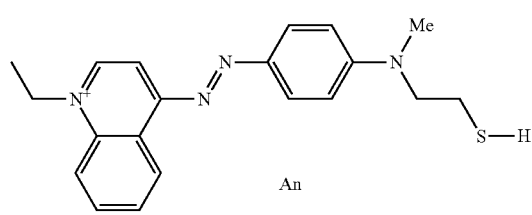
23
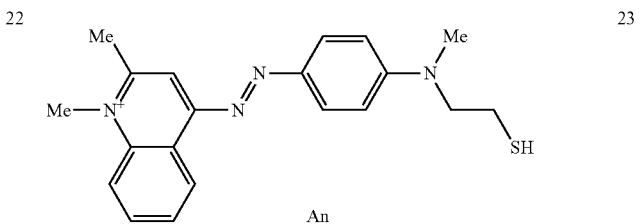
24
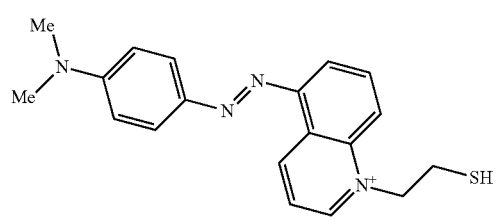
25
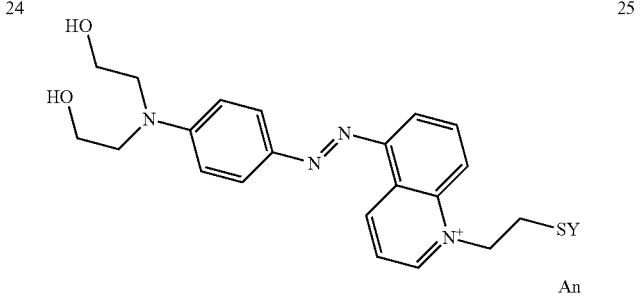
26
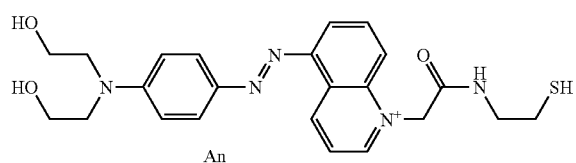
27
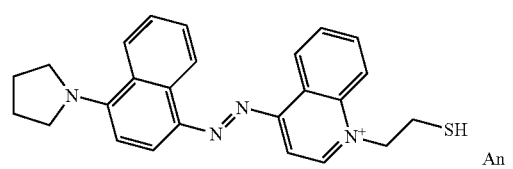

27
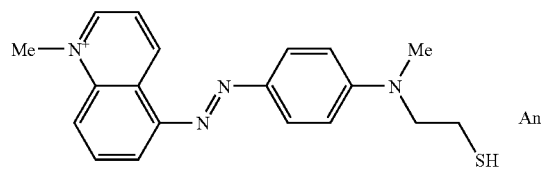
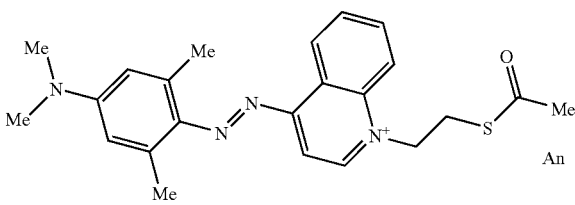
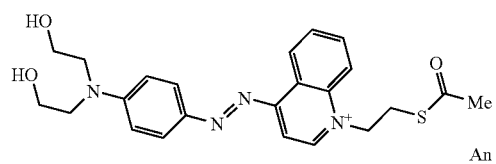
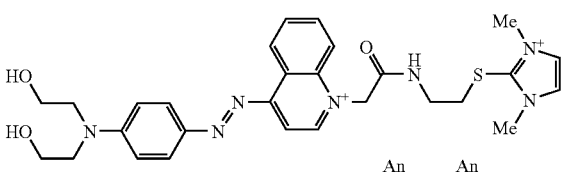
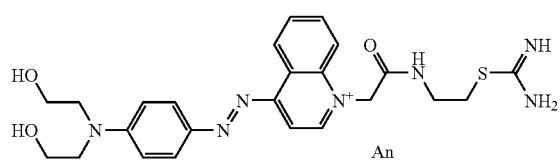
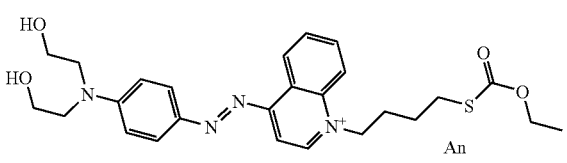
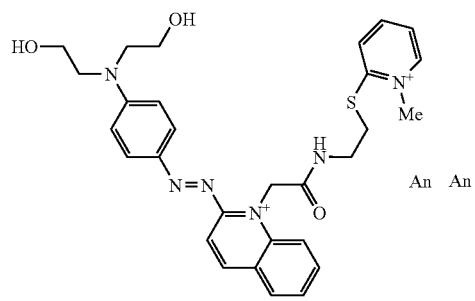
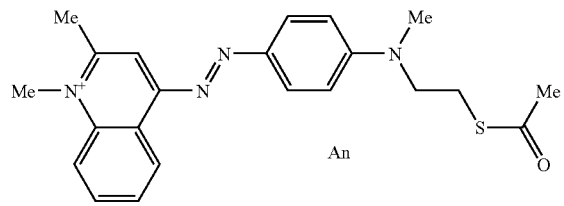
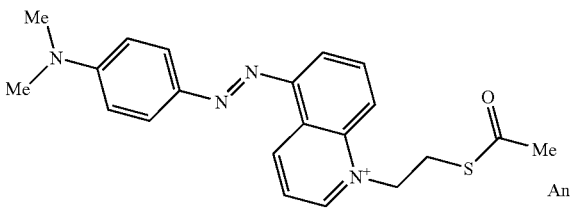
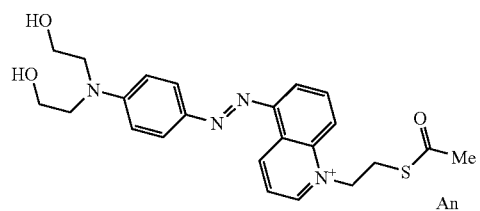
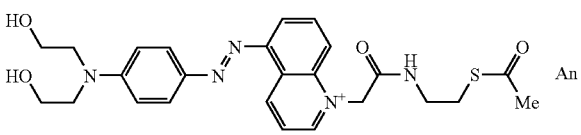
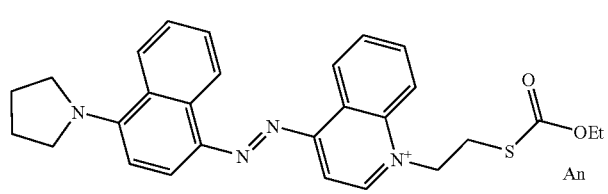

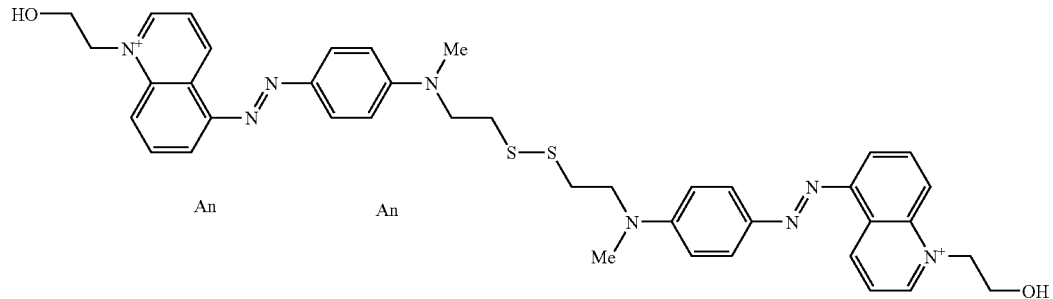
41
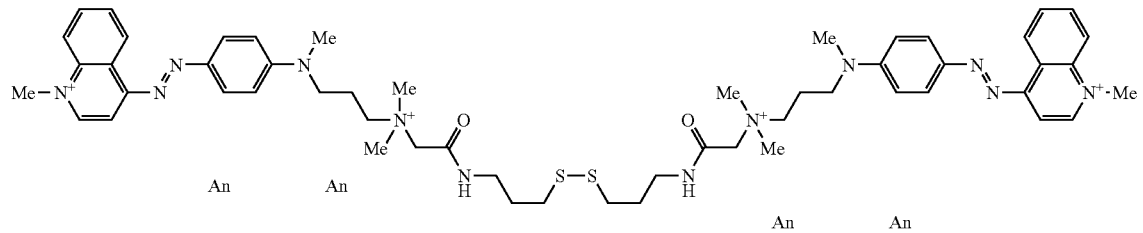
42
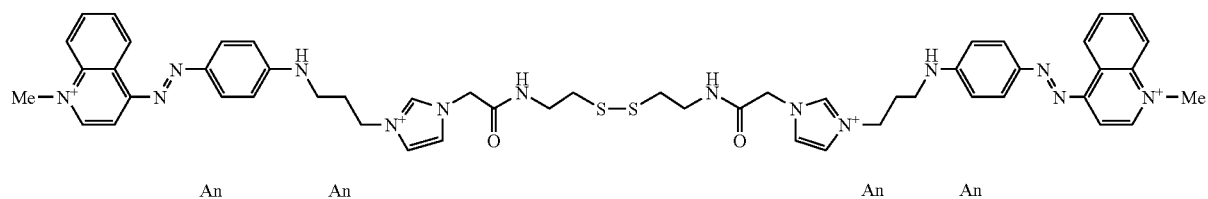
43
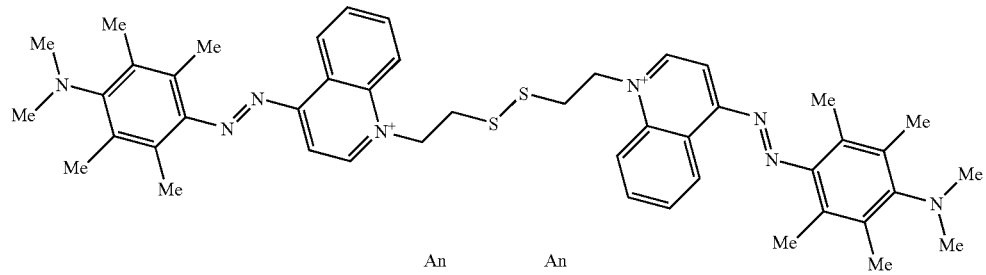
44
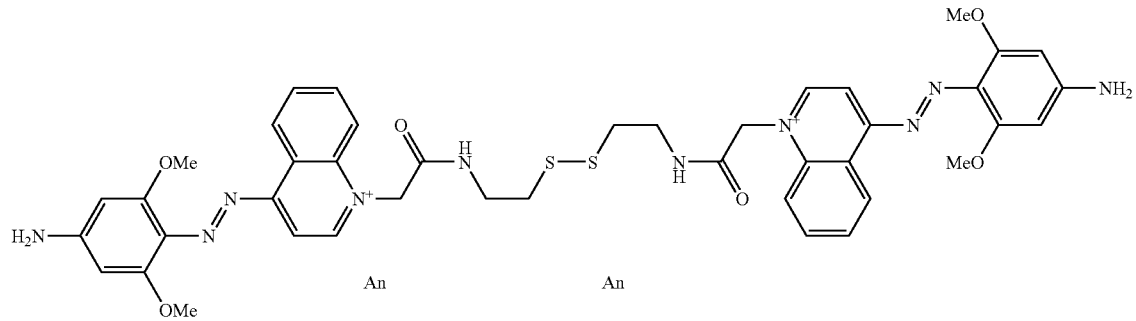
45
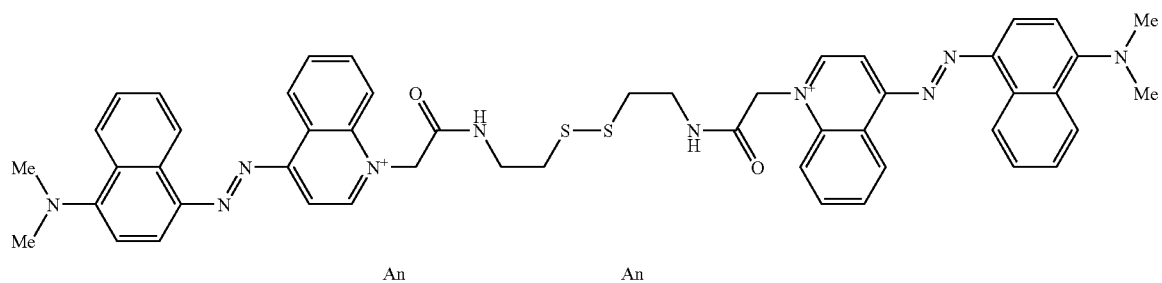
46

-continued
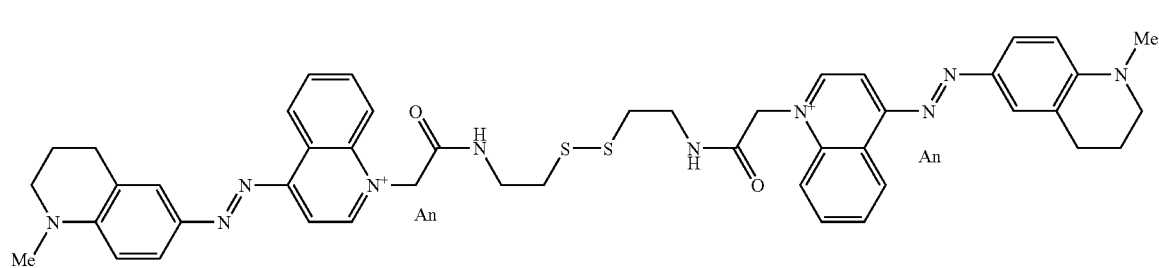
47
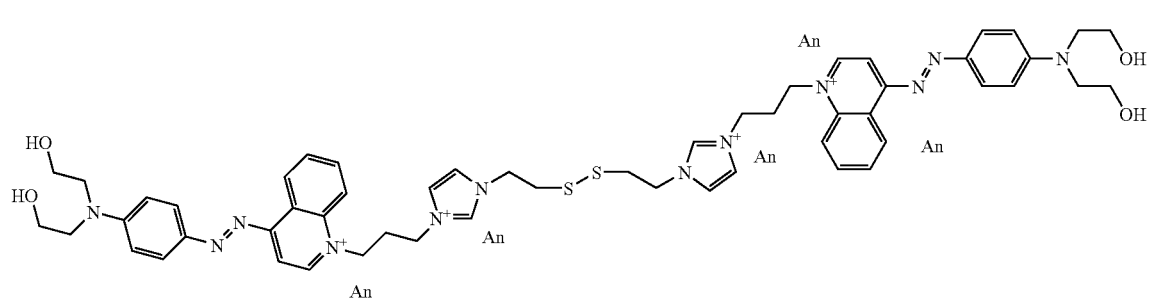
48
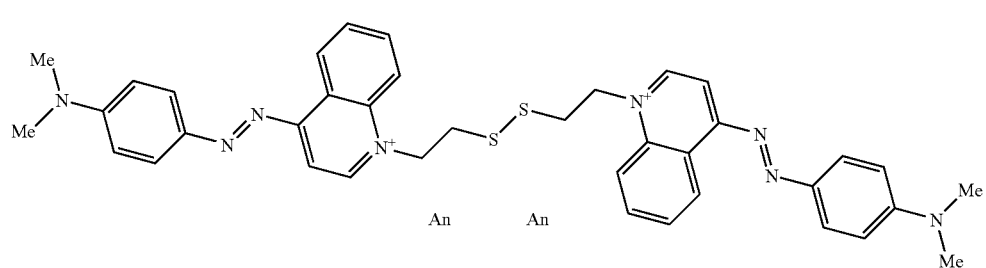
49
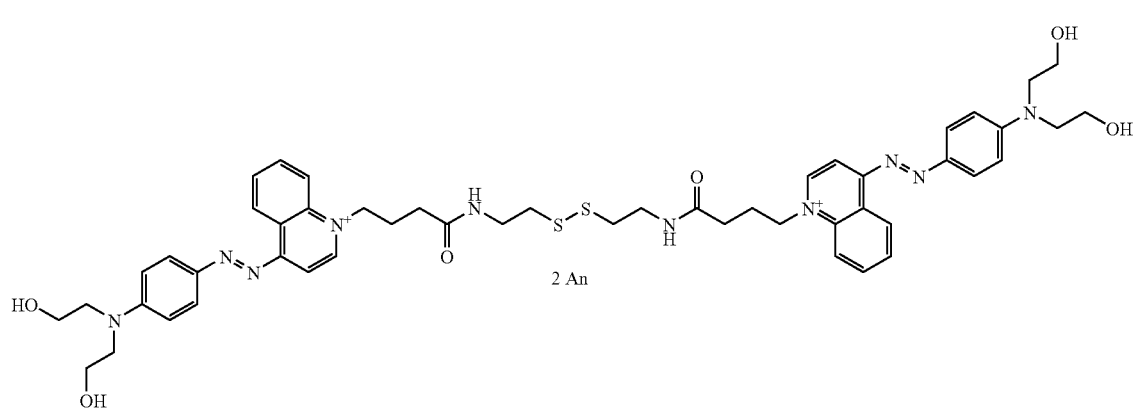
50 with An, which may be identical or different, representing a counterion.

These compounds can be obtained using the similar preparation processes described in the books *Advanced Organic Chemistry*, "Reactions, Mechanisms and Structures", J. March, 4th Ed, John Willey & Sons, 1992, T. W. Greene "*Protective Groups in Organic Synthesis*" or "*Color Chemistry*", H Zollinger, 3rd Ed, Wiley VCH.

According to a first embodiment, the process for synthesizing the compounds of formula (I) used in the invention may comprise implementing the following steps:

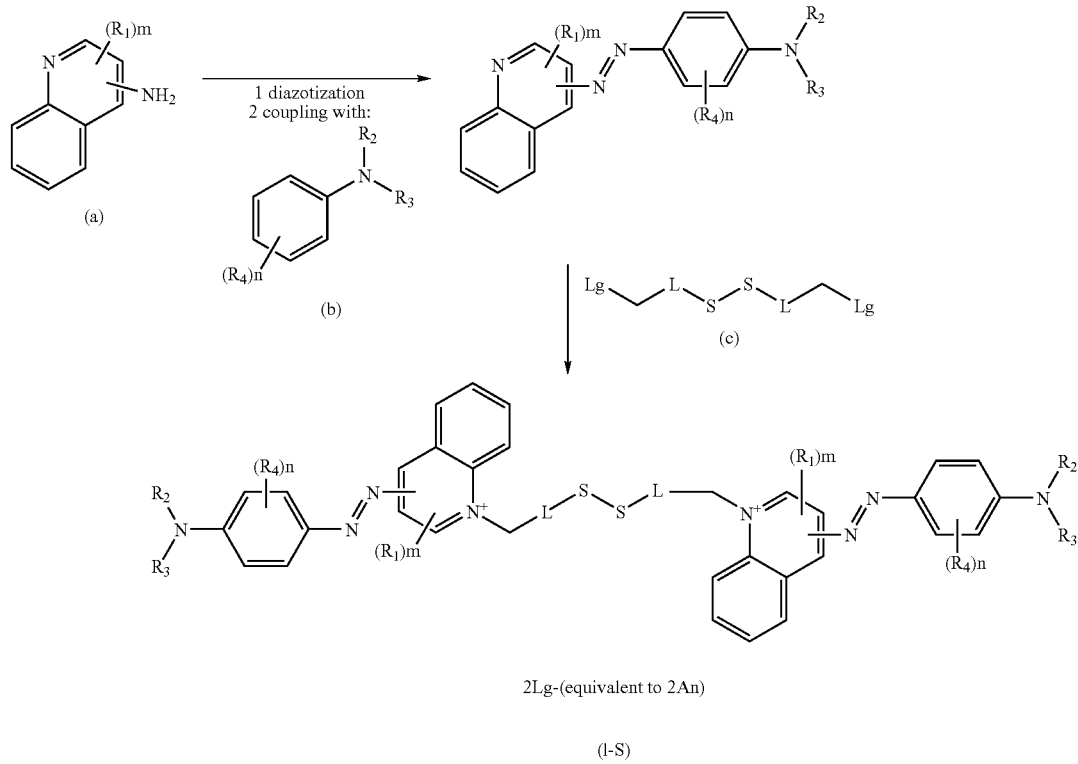

with $R_1$, $R_2$, $R_3$, $R_4$, L, An, m and n as defined above.

According to this process, a first step of diazotization of an amino quinoline (a) is carried out in a manner known to those skilled in the art. They can be obtained from the references described in Color Chemistry, H Zollinger, 3rd Edn, Wiley VCH, pages 166-169.

Thus, said amine is placed in the presence of phosphoric acid and of tert-butylnitrite. This reaction usually takes place at a temperature between −20° C. and 30° C., preferably between −10° C. and 20° C., at a pH of between 0 and 12.

Conventionally, the reaction is carried out in the presence of an appropriate solvent, among which mention may be made of water, alcohols, in particular aliphatic alcohols, containing up to 4 carbon atoms, organic acids, for example carboxylic or sulphonic acid containing up to 10 carbon atoms, and/or mineral acids of the hydrochloric acid or sulphuric acid type.

Once the reaction has been carried out, coupling of the product obtained with a compound of the aniline type (b) is performed.

This reaction is usually carried out in the presence of a solvent, which may be that of the preceding step.

The temperature is conventionally between −15° C. and 30° C., preferably between −10° C. and 20° C., at a pH of preferably between 0 and 8.

The product can be isolated by the techniques known to those skilled in the art (precipitation, evaporation, etc.).

In a final step, the resulting product is then dimerized in the manner known to those skilled in the art. Thus, said resulting product is placed in the presence of a double alkylating agent having a disulphide unit (c) in the presence of an aprotic apolar or polar solvent, such as acetonitrile, dimethylformamide, toluene, 1,3-dimethyl-2-oxohexahydropyrimidine (DMPU) or N-methylpyrrolidone. The temperature is usually between 10° C. and 180° C., preferably between 20° C. and 140° C.

The double alkylating agent having a disulphide unit (c) can be prepared according to the methods described in the literature and which are known to those skilled in the art:

Synthesis of the disulphide diol: see, for example, J. Org. Chem. 1985, 50(26), 5716-5719; J. Am. Chem. Soc. 1970, 92(24), 7224-7225; Tetrahedron 2004, 60(51), 11911-11922; J. Org. Chem. 1990, 55(9), 2580-2586; J. Org. Chem. 1985, 50(26), 5716-5719; J. Chem. Soc., Chem. Comm. 1981, 15, 741-742; Tet. Lett. 2005, 46(36), 6097-6099; J. Org. Chem. 1990, 55(9), 2580-2586; J. Org. Chem. 1985, 50(26), 5716-5719.

Synthesis of the double alkylating agent having a disulphide unit (c): see, by way of example, Bioorganic & Medicinal Chemistry Letters, 2004, 14(21), 5347-5350; WO04039771; Chem. Berichte, 1983, 116(1), 323-347, Tetrahedron 1985, 41(15), 3063-3069; J. Am. Chem. Soc. 1987, 109(25), 7648-7653; J. Org. Chem. 1995, 60(8), 2638-2639; Sulfur Lett. 2000, 24(3), 137-145.

According to a second embodiment, the process for synthesizing the compounds used in the invention may comprise carrying out the following steps:

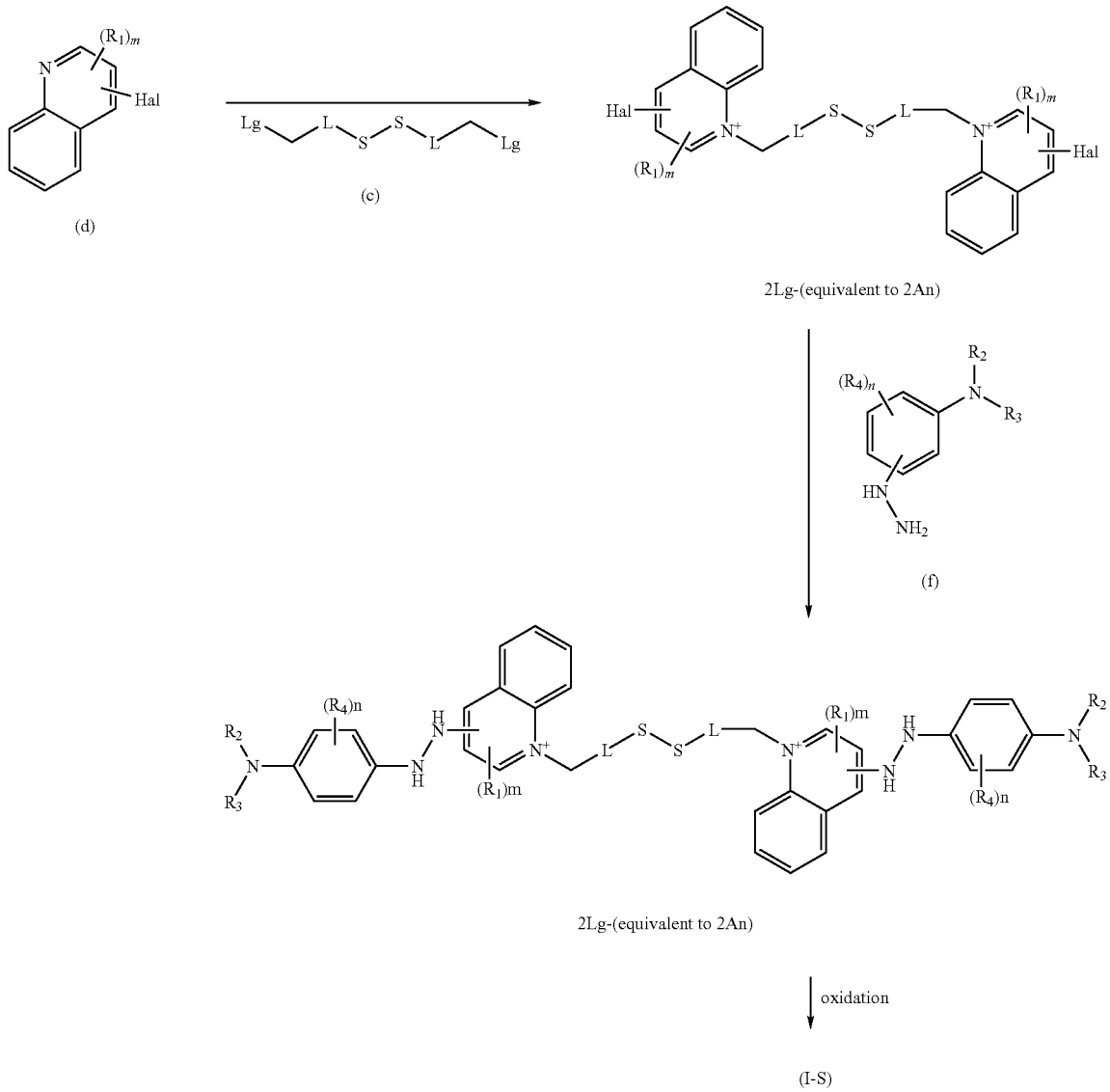

with $R_1$, $R_2$, $R_3$, $R_4$, L, An, m and n as defined above. Lg represents a leaving group such as chloride, bromide, tosylate or mesylate.

According to this process, a first step of alkylation of a quinoline compound (d) is carried out in a manner known to those skilled in the art. The conditions for carrying out such a step have been summarized previously.

Once the reaction has been carried out, a nucleophilic substitution of the product obtained, with a compound of arylhydrazine type (f), is performed. This reaction is usually carried out in the presence of a solvent, which may be that of the preceding step.

The temperature is conventionally between −15° C. and 60° C., preferably between 0° C. and 40° C., at a pH of preferably between 4 and 9.

The product can be isolated by the techniques known to those skilled in the art (precipitation, evaporation, etc.).

Once the reaction has been carried out, the quinolinium hydrazine derivative is oxidized by addition of an oxidant or by the simple addition of air. This reaction is usually carried out in the presence of a solvent, which may be that of the preceding step. The temperature is conventionally between −15° C. and 60° C., preferably between 0° C. and 40° C., at a pH of preferably between 4 and 9. The product can be isolated by the techniques known to those skilled in the art (precipitation, evaporation, etc.).

According to a third embodiment, the process for synthesizing the compounds used in the invention may comprise carrying out the following steps:

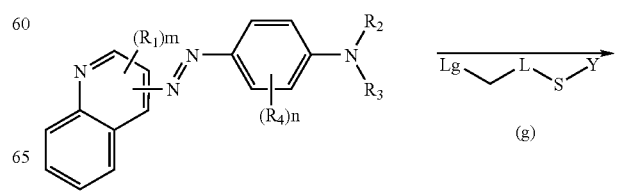

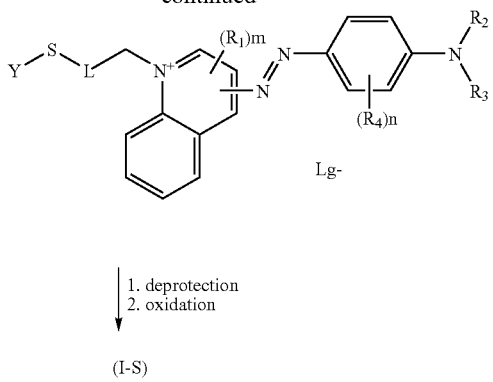

(I-S)

with $R_1$, $R_2$, $R_3$, $R_4$, L, An, m and n as defined above. Lg represents a leaving group such as chloride, bromide, tosylate or mesylate.

According to this process, a first step of quaternization of a noncationic azo quinoline compound is carried out, in the usual manner, with a protected thiol compound (g) in the presence of a polar or apolar, protic or aprotic solvent such as dichloromethane, toluene, ethyl acetate or water at spontaneous or alkaline pH. This quaternization step is known to those skilled in the art. The temperature is usually between 10° C. and 180° C., preferably between 20° C. and 100° C.

Once the reaction has been carried out, deprotection of the thiol group followed by oxidation of the thiol are performed. The conditions for carrying out such a step have been summarized below. The temperature is usually between 10° C. and 180° C., preferably between 20° C. and 100° C.

This process makes it possible to obtain, during the first step, a dye according to the invention comprising a protected thiol unit (for which x=y=1), during the thiol deprotection step, a dye comprising a thiol unit (for which x=y=1 and Y represents a hydrogen atom) or a thiolate unit (for which Y represents a metal, an ammonium or a phosphonium), and finally a disulphide dye (for which x=2 and y=0).

According to a fourth embodiment, the process for synthesizing the compounds used in the invention may comprise carrying out the following steps:

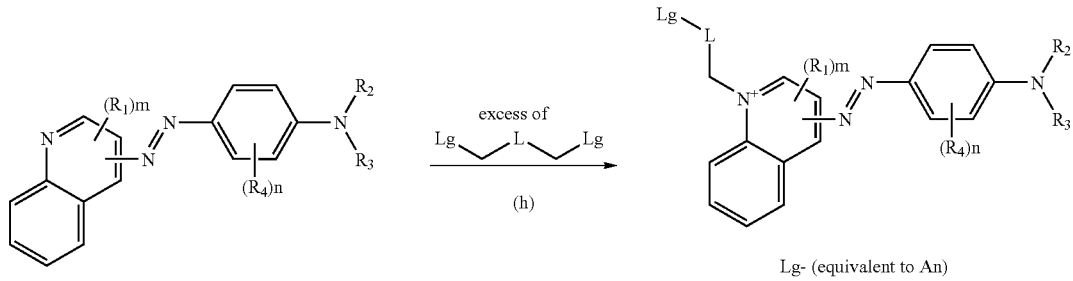

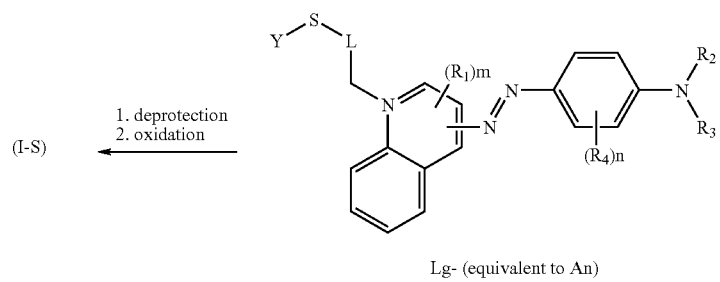

with $R_1$, $R_2$, $R_3$, $R_4$, L, An, m and n as defined above. Lg represents a leaving group such as chloride, bromide, tosylate or mesylate.

According to this process, a first step of quaternization of a noncationic azo quinolinium compound is carried out in the usual way with a compound Lg—CH$_2$—L—CH$_2$—Lg (h) in the presence of a protic or aprotic, polar or apolar solvent such as dichloromethane, toluene, ethyl acetate or water at spontaneous or alkaline pH. Lg represents a leaving group such as chloride, bromide, tosylate or mesylate.

This quaternization step is known to those skilled in the art. The temperature is usually between 10° C. and 180° C., preferably between 20° C. and 100° C. The quaternization is followed by a nucleophilic substitution with a YSH reactant.

Once the reaction has been carried out, a nucleophilic substitution of the product obtained is performed with a compound of Y—SH type (Y is as defined above). This reaction is below. The temperature is usually between 10° C. and 180° C., preferably between 20° C. and 100° C.

This process also makes it possible to obtain, during the first step, a dye according to the invention comprising a protected thiol unit (for which x=y=1), during the thiol deprotection step, a dye comprising a thiol unit (for which x=y=1 and Y represents a hydrogen atom) or a thiolate unit (for which Y represents a metal, an ammonium or a phosphonium), and finally a disulphide dye (for which x=2 and y=0).

According to another embodiment, a disulphide/thiol dye according to the invention can be obtained by nucleophilic substitution of an amine HNR$_2$R$_3$ (i) on an aromatic nucleus such as phenyl of an azo dye comprising a quinolinium unit bearing, in the ortho- or para-position of said phenyl, a nucleofuge group, for example a halogen or an alkoxy:

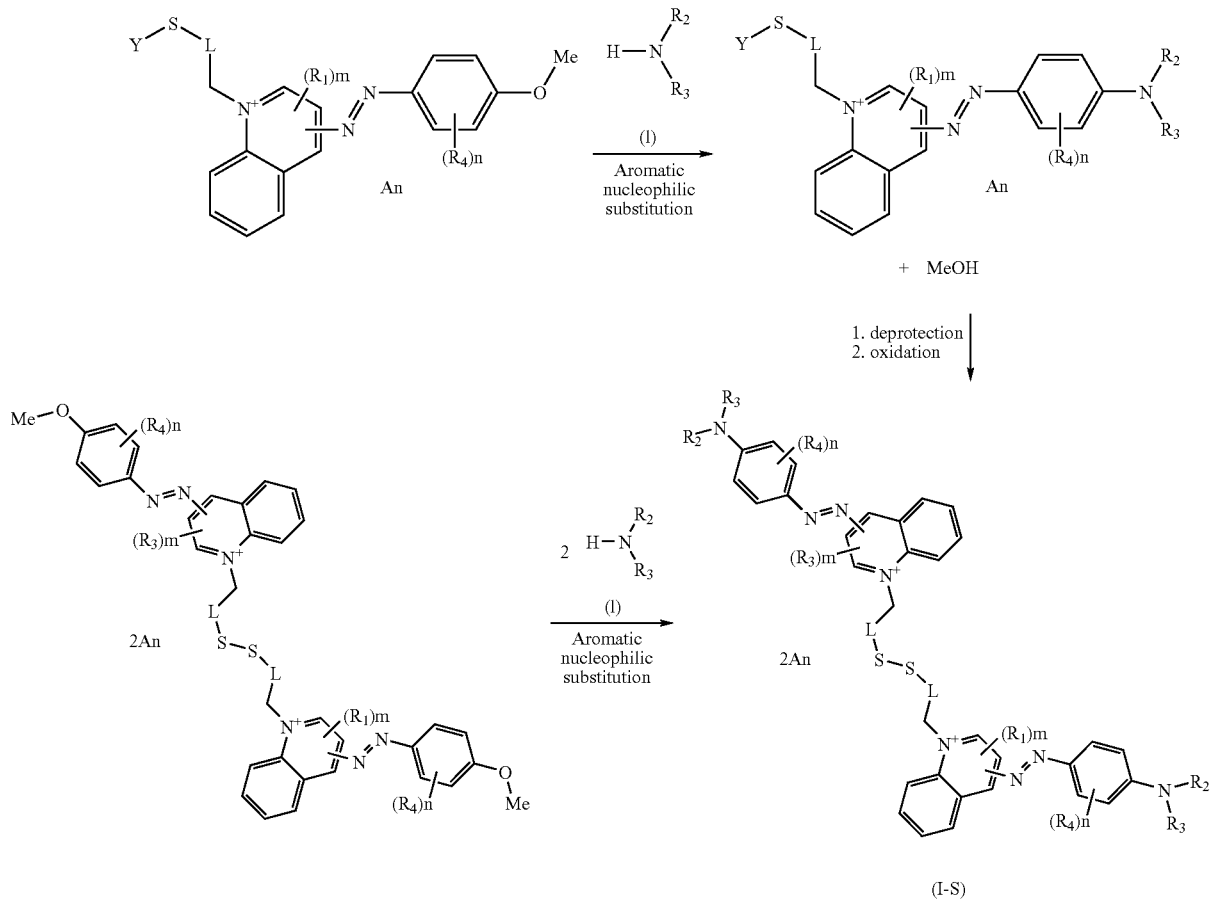

usually carried out in the presence of a protic or aprotic, polar or apolar solvent such as dichloromethane, toluene, ethyl acetate, water or alcohols. Lg represents a leaving group such as chloride, bromide, tosylate or mesylate.

The temperature is conventionally between −15° C. and 60° C., preferably between 0° C. and 50° C., at a pH of preferably between 7 and 9.

The product can be isolated by the techniques known to those skilled in the art (precipitation, evaporation, etc.).

Once the reaction has been carried out, deprotection of the thiol group and then oxidation of the thiol are performed. The conditions for carrying out such a step have been summarized with $R_1$, $R_2$, $R_3$, $R_4$, L, Y, An, m and n as defined above.

This reaction is carried out in a manner known to those skilled in the art, in a polar solvent, preferably a protic polar solvent, such as alcohols. The precursor bearing the nucleofuge group can be readily obtained according to the first steps of the processes described above.

If the process has recourse to diazotization of an aminoquinoline followed by coupling, the coupler chosen may be a phenol, which can be subsequently alkylated according to the conditions known to those skilled in the art.

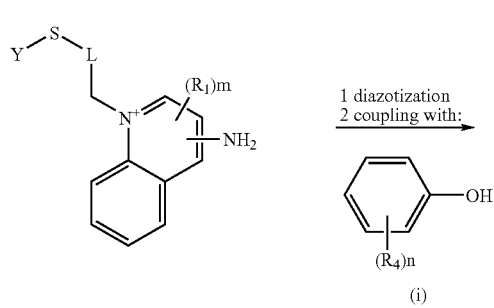
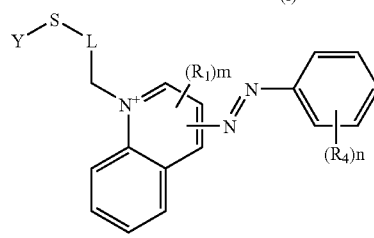
alkylation
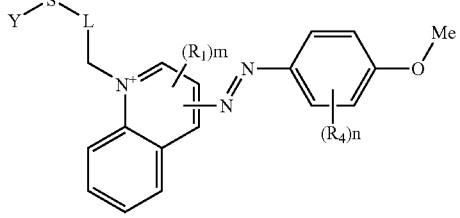
with $R_1$, $R_4$, L, Y, An, m and n as defined above. Lg represents a leaving group such as chloride, bromide, tosylate or mesylate.
According to a first embodiment, the process for synthesizing the compounds of formula (II) used in the invention may comprise carrying out the following steps:
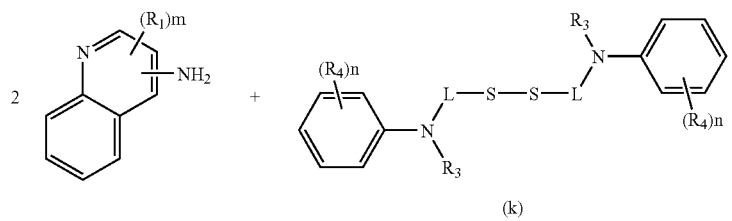
1 diazotization
2 coupling
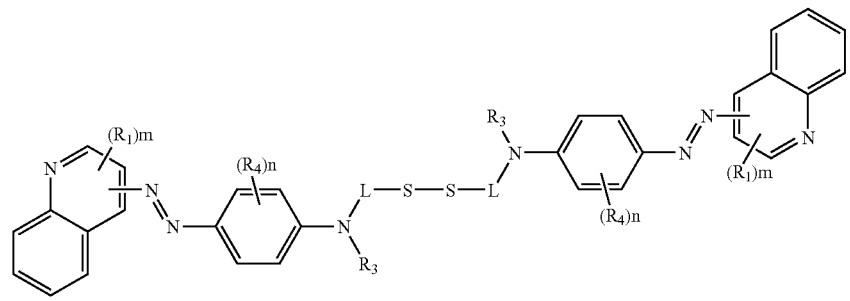
quaternization -continued

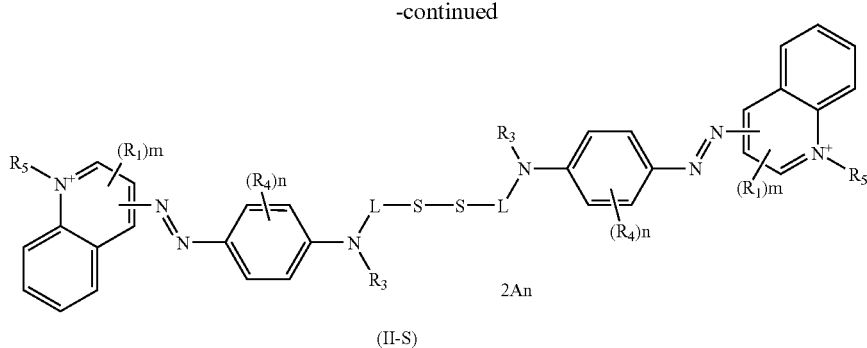

(II-S)

with $R_1$, $R_3$, $R_4$, $R_5$, L, An, m and n as defined above.

According to this process, a first step of diazotization of an aminoquinoline is carried out in a manner known to those skilled in the art. The conditions for carrying out such a step have been previously summarized.

Once the reaction has been carried out, coupling of the product obtained, with a compound of the disulphide type (k), is performed.

This reaction is usually carried out in the presence of a solvent, which may be that of the preceding step.

The temperature is conventionally between −15° C. and 30° C., preferably between −10° C. and 20° C., at a pH of preferably between 0 and 8.

The product can be isolated by the techniques known to those skilled in the art (precipitation, evaporation, etc.).

The resulting product is then quaternized in the usual way (see, for example, Synth. Comm. 2005, 35(23), 3021-3026; EP1386916; Synthesis, 1986, 5, 382-383; Liebigs Annalen der Chemie, 1987, 1, 77-79; Bull. Chem. Soc. Jap. 1977, 50(6), 1510-1512; J. Org. Chem. 1979, 44(4), 638-639). For example, the product obtained can be brought into contact with an alkyl sulphate, such as dimethyl sulphate, diethyl sulphate or dipropyl sulphate, or an alkyl halide or an alkylaryl halide such as iodomethane, iodoethane, 2-bromoethanol or benzyl bromide, in the presence of a protic or aprotic, polar or apolar solvent such as dichloromethane, toluene, ethyl acetate or water at spontaneous or alkaline pH. The product obtained can also be brought into contact with dialkyl carbonate, such as dimethyl carbonate or diethyl carbonate, in the presence of a base. The temperature is usually between 10° C. and 180° C., preferably between 20° C. and 100° C.

According to a second embodiment, the process for synthesizing the compounds used in the invention may comprise carrying out the following steps:

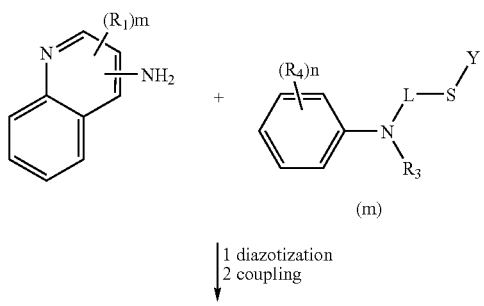

(m)

1 diazotization
2 coupling

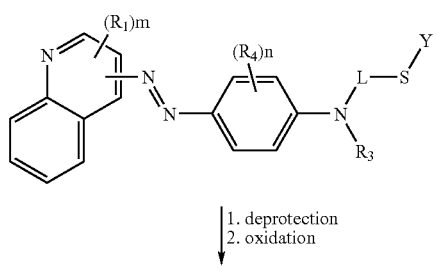

1. deprotection
2. oxidation

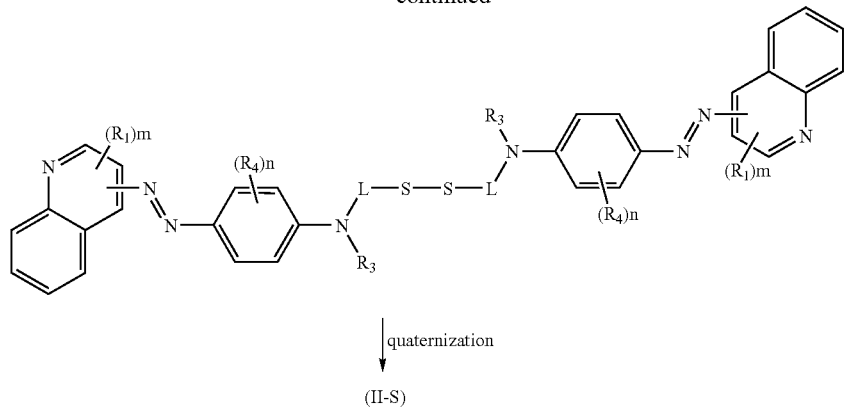

(II-S)

with $R_1$, $R_3$, $R_4$, L, An, m and n as defined above.

According to this process, a first step of diazotization of an aminoquinoline is carried out in a manner known to those skilled in the art.

Once the reaction has been carried out, coupling of the product obtained, with a compound of the protected thiol type (m), is performed.

Once the reaction has been carried out, deprotection of the thiol group and then oxidation of the thiol are performed. The temperature is usually between 10° C. and 180° C., preferably between 20° C. and 100° C.

The resulting product is then quaternized in the usual manner.

The conditions for carrying out all the steps of this process have been summarized previously. At each step of this synthesis, the intermediate and thus the final product can be isolated by the techniques known to those skilled in the art (precipitation, evaporation, etc.).

According to a third embodiment, the process for synthesizing the compounds used in the invention may comprise carrying out the following steps:

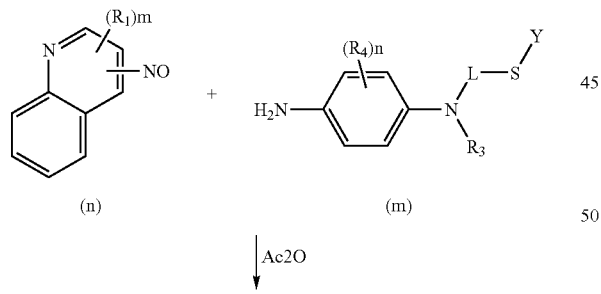

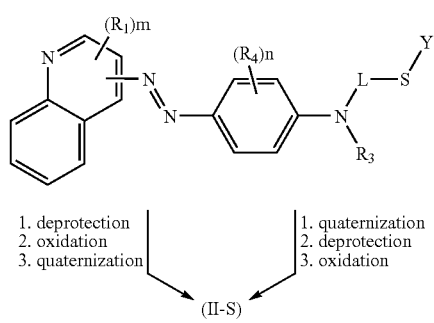

1. deprotection
2. oxidation
3. quaternization 1. quaternization
2. deprotection
3. oxidation (II-S)

with $R_1$, $R_3$, $R_4$, $R_5$, L, Y, An, m and n as defined above.

According to this process, the azo compound is prepared by reacting a nitroso compound (n) and an aromatic amine (m). This process is known to those skilled in the art and is described in J. Hetero. Chem. 21(2), 501-3, 1984. The conditions for carrying out the other steps of the synthesis have been summarized previously.

A variant of this synthesis is the use of a disulphide compound

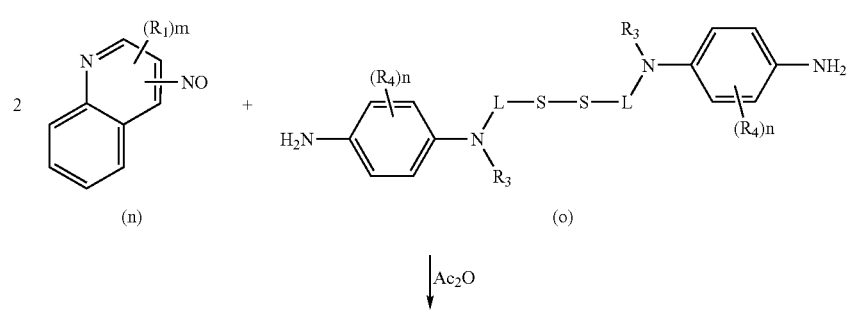

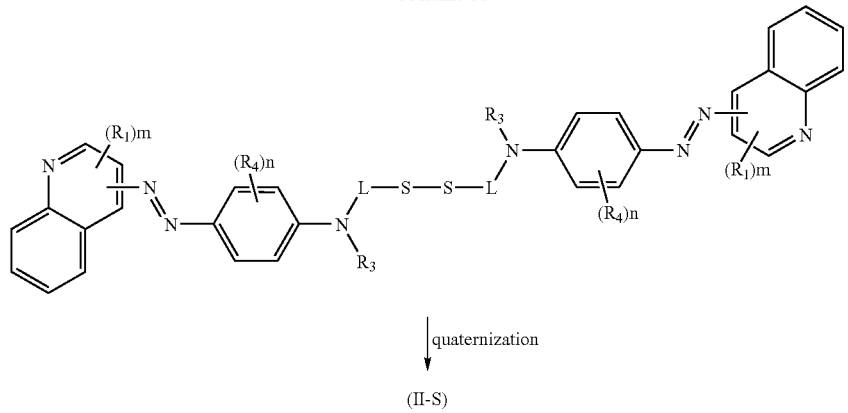

(II-S)

with $R_1$, $R_3$, $R_4$, $R_5$, L, An, m and n as defined above.

A variant of this third synthesis is the use of a hydroxylamine compound. This process is known to those skilled in the art and is also described in *J. Hetero. Chem* 21(2), 501-3, 1984.

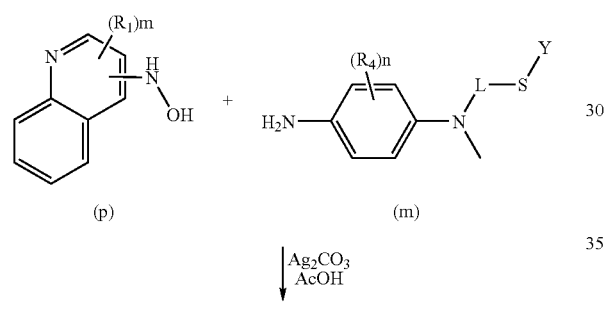

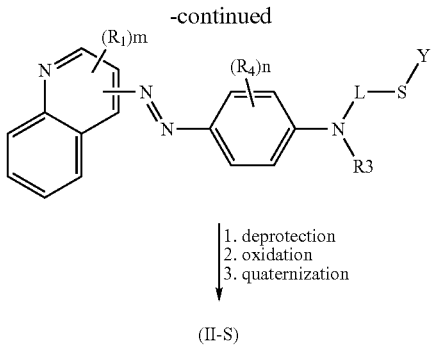

1. deprotection
2. oxidation
3. quaternization (II-S)

with $R_1$, $R_3$, $R_4$, L, Y, An, m and n as defined above.

According to another embodiment, the process for synthesizing the compounds used in the invention may comprise carrying out the following steps:

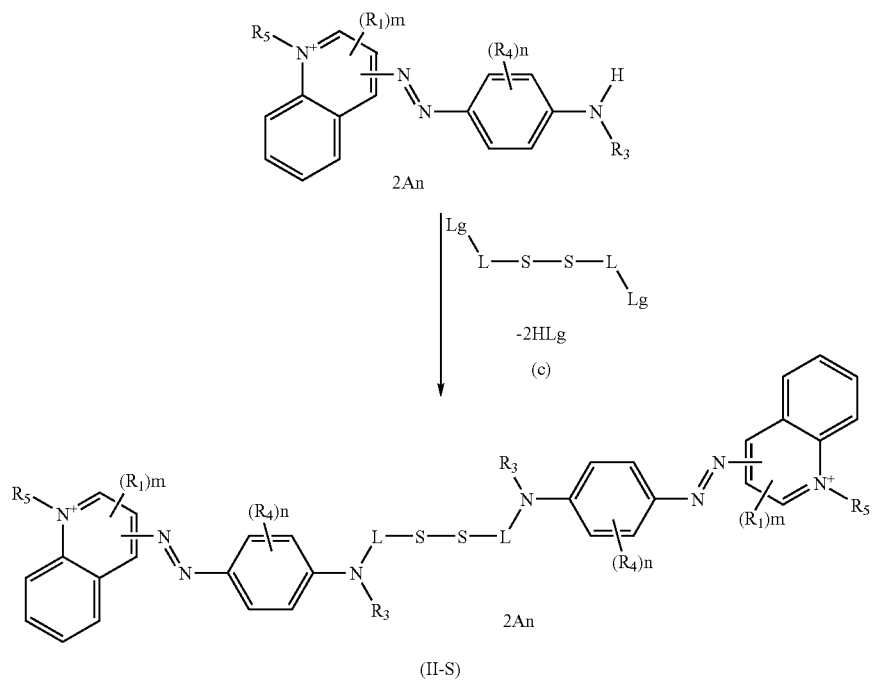

(II-S)

with $R_1$, $R_3$, $R_4$, $R_5$, L, Lg, An, m and n as defined above.

According to another embodiment, the process for synthesizing the compounds used in the invention may comprise carrying out the following steps:

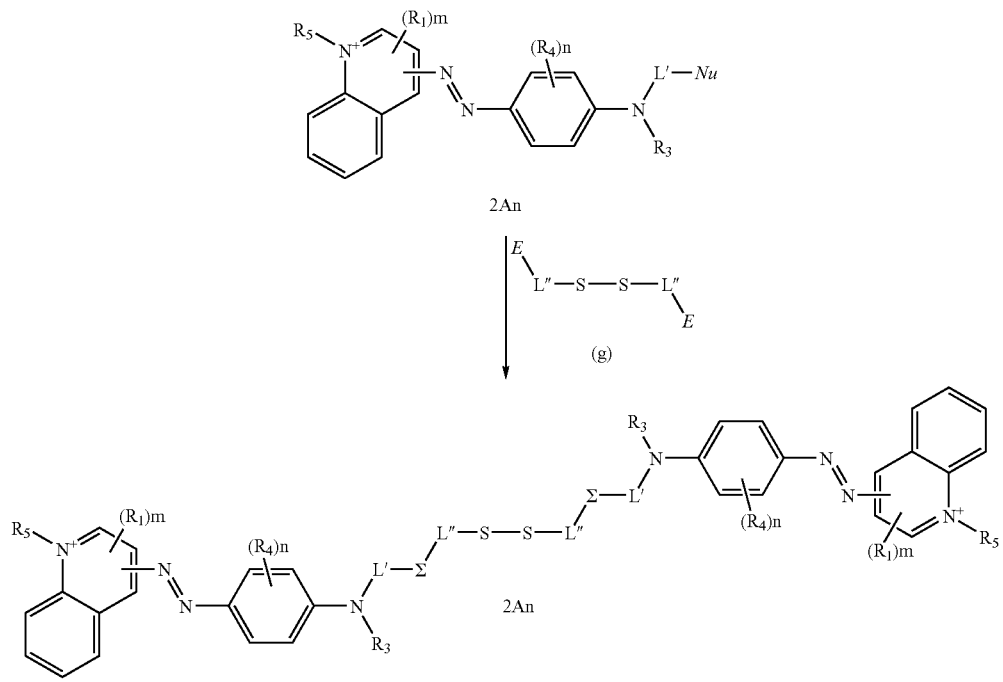

with $R_1$, $R_3$, $R_4$, $R_5$, L, An, m and n as defined above; Nuc representing a nucleophilic group; E representing an electrophilic group; Σ the bond generated after attack of the nucleophile on the electrophile; the combination of the group L'-Σ-L" is contained by the linker L as defined above.

By way of example, the covalent bonds Σ that can be generated are listed in the table below, based on condensation of electrophiles with nucleophiles:

| Electrophiles E | Nucleophiles Nuc | Covalent bonds Σ |
|---|---|---|
| Activated esters* | Amines | Carboxamides |
| Acyl azides** | Amines | Carboxamides |
| Acyl halides | Amines | Carboxamides |
| Acyl halides | Alcohols | Esters |
| Acyl cyanides | Alcohols | Esters |
| Acyl cyanides | Amines | Carboxamides |
| Alkyl halides | Amines | Alkylamines |
| Alkyl halides | Carboxylic acids | Esters |
| Alkyl halides | Thiols | Thioesters |
| Alkyl halides | Alcohols | Ethers |
| Sulphonic acids and salts thereof | Thiols | Thioethers |
| Sulphonic acids and salts thereof | Carboxylic acids | Esters |
| Sulphonic acids and salts thereof | Alcohols | Ethers |
| Anhydrides | Alcohols | Esters |
| Anhydrides | Amines | Carboxamides |
| Aryl halides | Thiols | Thioethers |
| Aryl halides | Amines | Arylamines |
| Aziridines | Thiols | Thioethers |
| Carboxylic acids | Amines | Carboxamides |
| Carboxylic acids | Alcohols | Esters |
| Carbodiimides | Carboxylic acids | N-acylureas |
| Diazoalkanes | Carboxylic acids | Esters |
| Epoxides | Thiols | Thioethers |
| Haloacetamides | Thiols | Thioethers |
| Imide esters | Amines | Amidines |
| Isocyanates | Amines | Ureas |
| Isocyanates | Alcohols | Urethanes |
| Isothiocyanates | Amines | Thioureas |
| Maleimides | Thiols | Thioethers |
| Sulphonic esters | Amines | Alkylamines |
| Sulphonic esters | Thiols | Thioethers |
| Sulphonic esters | Carboxylic acids | Esters |
| Sulphonic esters | Alcohols | Ethers |
| Sulphonyl halides | Amines | Sulphonamides |

*activated esters of general formula —CO—Part, with Part representing a leaving group such as optionally substituted oxysuccinimidyl, oxybenzotriazolyl, or aryloxy;

**the acyl azides can rearrange to give isocyanates.

By way of nonlimiting indication, a dye with a linker containing carboxamido groups is synthesized by reacting an azo compound containing a nucleophilic amino group with a compound containing two acyl halide groups (r).

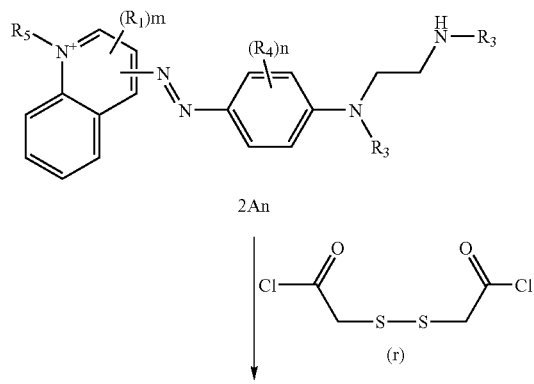

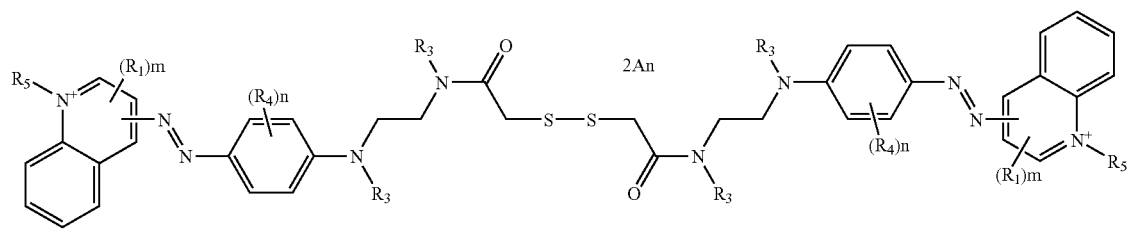

with $R_1$, $R_3$, $R_4$, $R_5$, L, An, m and n as defined above.

This reaction is carried out in a manner known to those skilled in the art, in a polar solvent, preferably alcohols, in the presence of a base such as triethylamine. The final product can be isolated by the techniques known to those skilled in the art (precipitation, evaporation, etc.) and the precursors can be readily obtained according to the first steps of the processes described above.

According to another embodiment, a disulphide/thiol dye according to the invention can be obtained by aromatic nucleophilic substitution on an azo dye comprising a quinolinium unit bearing, in the ortho- or para-position, a nucleofuge group, for example a halogen or an alkyloxy, with a reactant H—$NR_3$-L-S—Y (s) or H—$NR_3$—L—S—S—L—$NR_3$—H (t) (for example, cysteamine or cysteine):

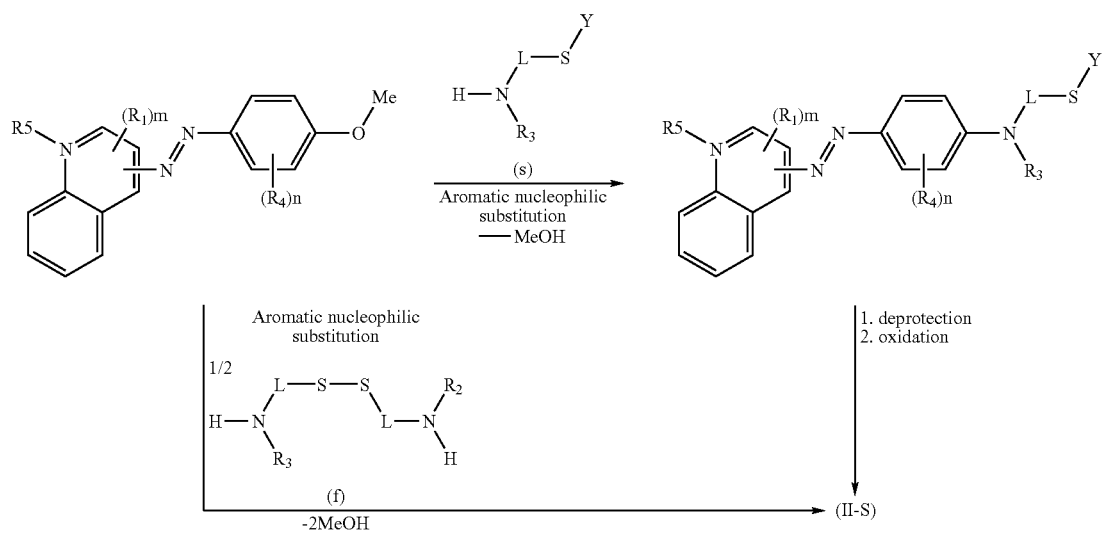

with $R_1$, $R_3$, $R_4$, $R_5$, L, Y, An, m and n as defined above.

This reaction is carried out in a manner known to those skilled in the art, in a polar solvent, preferably alcohols. The precursor bearing the nucleofuge group can be readily obtained according to the first steps of the processes described above. If the process has recourse to diazotization of an aminoquinoline followed by coupling, the coupler chosen may be a phenol, which can subsequently be methylated according to the conditions known to those skilled in the art.

The protected thiol dyes of formula (I-Y), for which m and n are 1, can be synthesized in two stages. The first stage comprises preparing the unprotected thiol dye (I-H) according to the methods known to those skilled in the art, for example "*Thiols and organic Sulfides*", "*Thiocyanates and Isothiocyanates, organic*", Ullmann's Encyclopedia, Wiley-VCH, Weinheim, 2005. In addition, the second stage comprises protecting the thiol function according to the conventional methods known to those skilled in the art, so as to give the protected thiol dyes of formula (I-Y). By way of example, to protect the —SH thiol function of the thiol dye, the methods of the books "*Protective Groups in Organic Synthesis*", T. W. Greene, John Willey & Sons ed., NY, 1981, pp. 193-217; "*Protecting Groups*", P. Kocienski, Thieme, 3rd ed., 2005, chap. 5, can be used. This method can be illustrated by means of the method comprising i) generating thiol dyes of formula (I-H) by reducing a two-chromophore, heterocyclic dye bearing a disulphide function —S—S—, such as (I-S), and ii) protecting said thiol function of (I-H) with the reactant (u) Y'R, according to the conventional methods, so as to obtain the protected thiol dyes of formula (I-Y). The thiol compound (I-H) can also be metallated with an alkali metal or alkaline earth metal Met* so as to give the thiolate dye of formula (I-Met).

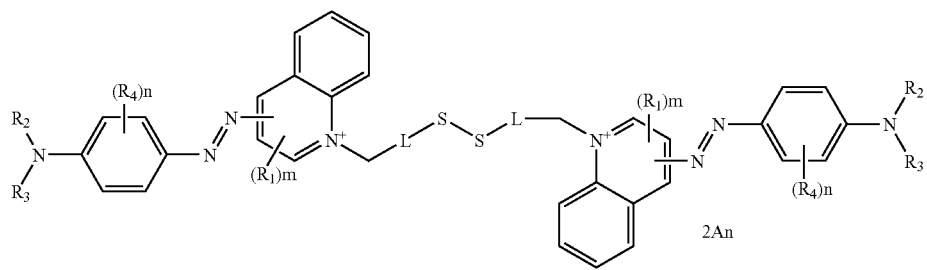

(I-S)

↓ reducing agent

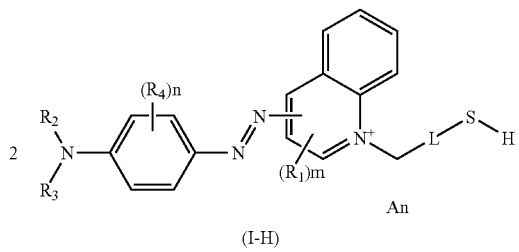

(I-H)

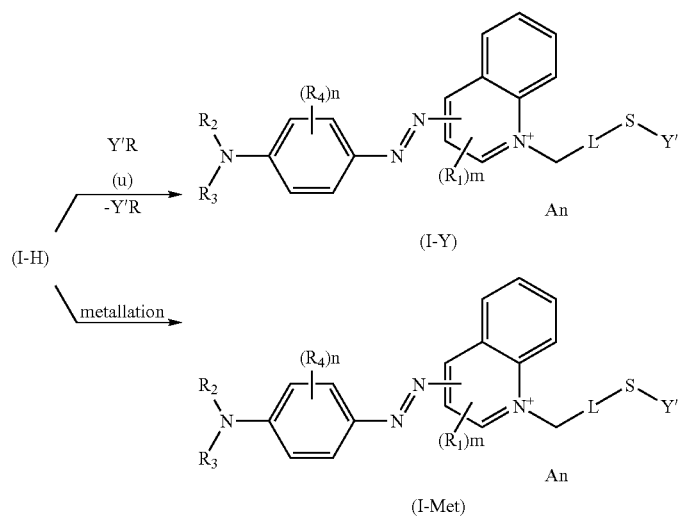

with $R_1$, $R_3$, $R_4$, $R_5$, L, An, m and n as defined above; Y' representing a thiol-function-protecting group; Met* representing an alkali metal or an alkaline earth metal, particularly sodium or potassium, it being understood that, when the metal is an alkaline earth metal, 2 chromophores with a thiolate function —S$^-$ can be associated with 1 metal$^{2+}$; R representing a nucleofuge leaving group, for instance mesylate, tosylate, triflate or halide.

According to another possibility, a protected thiol compound (v) protected with a protecting group Y' as defined above, prepared according to one of the procedures described in the books mentioned above, said protected thiol compound comprising at least one nucleophilic function, can be reacted with a sufficient, preferably equimolar, amount of a chromophore (w), and which comprises an electrophilic function, so as to form a covalent bond $\Sigma$; see below, the preparation of dyes of formula (I'-Y):

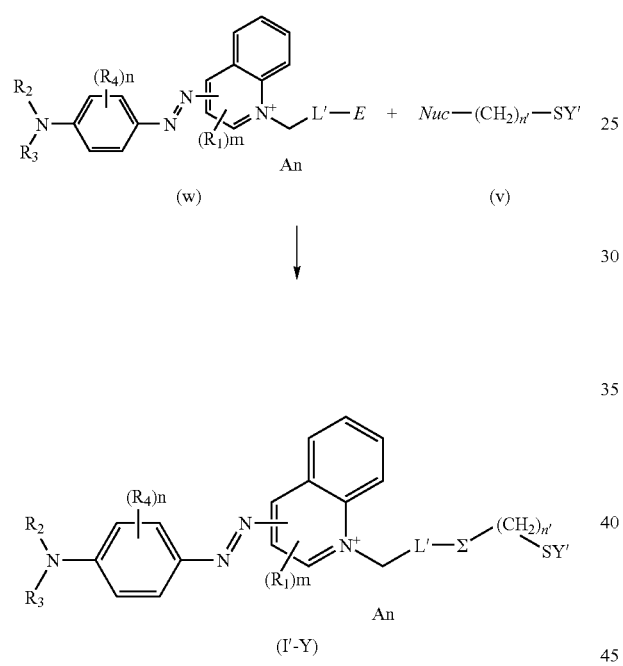

with $R^1$ to $R^4$, m, n, Nuc, E, $\Sigma$ and Y' as defined above; L' representing an optionally substituted and/or optionally interrupted, (hetero) aromatic or non(hetero)aromatic, cyclic or noncyclic, linear or branched, saturated or unsaturated $C_1$-$C_{20}$, preferably $C_2$-$C_{10}$, hydrocarbon-based chain optionally terminated with at least one heteroatom or group comprising at least one heteroatom, preferably oxygen or nitrogen; and n' representing an integer between 1 and 6 inclusive.

A variant to this process is to use a chromophore having an electrophilic acrylate function (—OCO—C=C—) on which is carried out an addition reaction which will generate a $\Sigma$ bond.

Use may also be made of a thiol reactant (x): Y'—SH comprising a Y' group as defined above, the nucleophilic SH function of which can react on the carbon atom of the L radical in the alpha-position with respect to the halogen atom borne by a chromophore, the ketone functions of which are optionally protected beforehand, as seen above, so as to give the protected thiol dye of formula (I-Y):

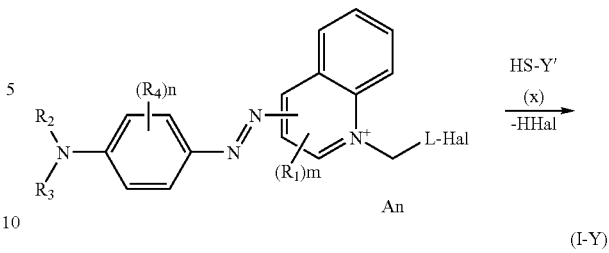

with $R^1$ to $R^4$, L, Y', n, m and (I-Y) as defined above, and Hal representing a nucleofuge halogen atom such as bromine, iodine or chlorine.

More particularly, a nucleofuge leaving group may be substituted with a thiourea group (S=C(NRR)NRR) so as to generate isothiouroniums; for example, if the thiourea group is a thioimidazolinium (y), so as to give the dye which is S-protected with an imidazolium group (I"-Y):

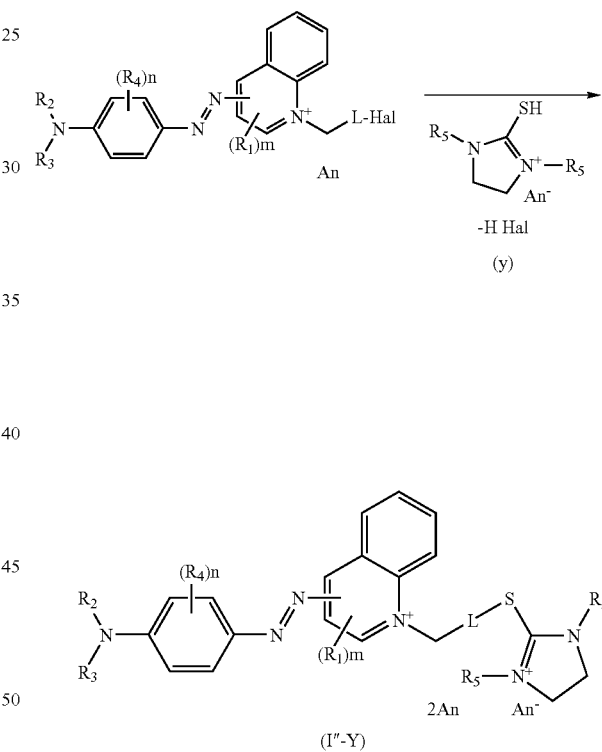

with $R_1$ to $R_5$, L, n, m, Hal and An as defined above.

In accordance with another possibility, certain protected thiol dyes (I'-Y) can be obtained by reacting a protected thiol compound with a compound bearing two carboxylic acid functions which are activated according to the conventional methods (for example, reaction with a carbodiimide or with thionyl chloride). The resulting product (z) is subsequently reacted with a chromophore, the ketone functions of which are optionally protected beforehand, as seen above, and which bears a nucleophilic function, for example of primary or secondary amine type or of aliphatic alcohol type.

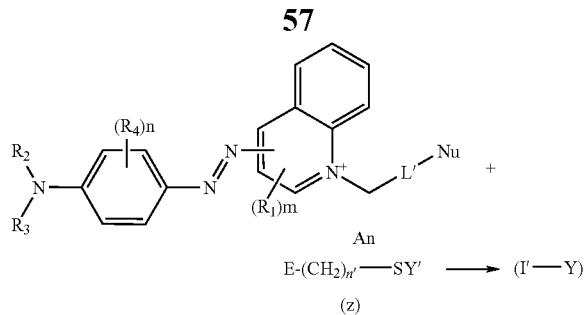

with $R_1$ to $R_5$, L', n, m, n', E, Nu and (I'-Y) as defined above.

A synthesis variant is to combine the preceding pathway with the first pathway, i.e. using two equivalents of the dye providing a nucleophilic group with a disulphide dielectrophilic reactant (a'), it is possible to generate, after condensation, the disulphide dichromophoric product (I'-S), it being possible for the latter to undergo a reduction so as to form the thiol dye (I'-H), which in turn can either be protected so as to form the protected thiol dye (I"-Y), or be metallated with an alkali metal so as to give the metallated dye (I'"$_{Metal}$):

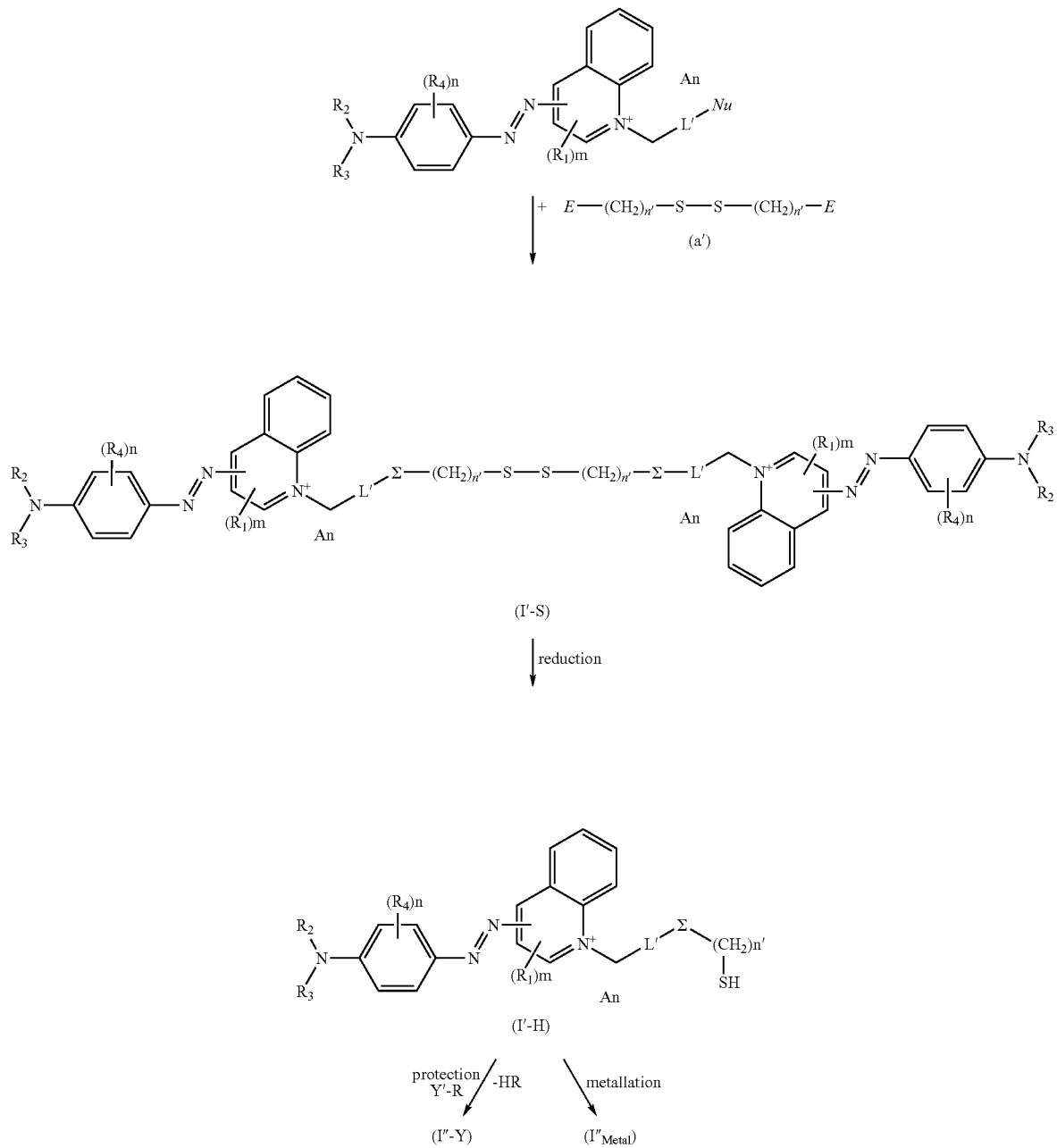

with $R_1$ to $R_5$, L', n, m, n', E, Nu and (I'-Y) as defined above.

In accordance with another possibility, the protected thiol dyes of formula (I'''-Y) can be obtained by reacting a compound (b') comprising a thiol group protected with a Y' group and a nucleofuge leaving group Lg, for instance mesylate, tosylate, triflate or halide, on the chromophore.

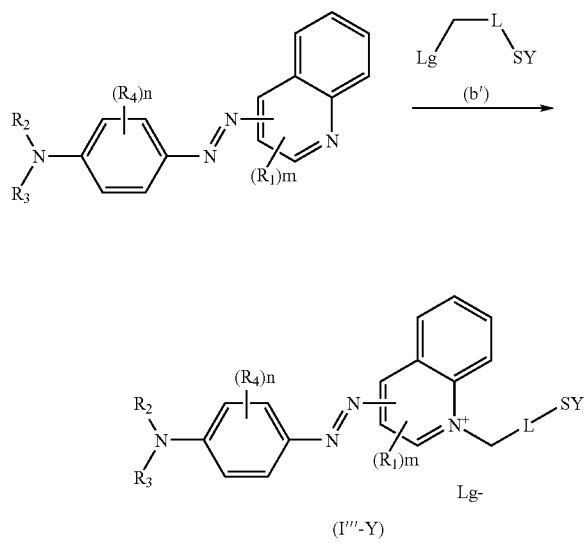

with $R_1$ to $R_4$, L, Y, n, m, and Lg as defined above.

Reference may be made to the book *Advanced Organic Chemistry*, "Reactions, Mechanisms and Structures", J. March, 4th Ed, John Willey & Sons, 1992 or T. W. Greene "*Protective Groups in Organic Synthesis*", for further details on the operating conditions used for the processes mentioned above.

The thiol dyes formed can be converted to —SY' protected thiol dyes by protection of the —SH thiol using conventional protecting groups. The thiol dyes are metallated by also using the conventional methods known to those skilled in the art, such as those described in *Advanced Organic Chemistry*, "Reactions, Mechanisms and Structures", J. March, 4th Ed, John Willey & Sons, NY, 1992.

The protected thiol dyes can be deprotected by conventional pathways such as those described in the books "*Protective Groups in Organic Synthesis*", T. W. Greene, John Willey & Sons ed., NY, 1981; "Protecting Groups", P. Kocienski, Thieme, 3rd ed., 2005.

The starting reactants are commercially available or accessible by conventional methods known to those skilled in the art. By way of example, mention may be made of document U.S. Pat. No. 4,579,949.

Another subject of the invention is a composition which contains at least one disulphide, thiol or protected thiol dye of formula (I) or (II). In addition to the presence of at least one dye of formula (I), the composition of the invention may also contain a reducing agent.

This reducing agent may be chosen from thiols, for example, cysteine, homocysteine, thiolactic acid, the salts of these thiols, phosphines, bisulphite, sulphites, thioglycolic acid, and also its esters, in particular glycerol monothioglycolate, and thioglycerol. This reducing agent may also be chosen from borohydrides and derivatives thereof, for instance the salts of borohydride, of cyanoborohydride, of triacetoxyborohydride or of trimethoxyborohydride: sodium salts, lithium salts, potassium salts, calcium salts, quaternary ammonium (tetramethylammonium, tetraethylammonium, tetra-n-butylammonium, benzyltriethylammonium) salts; catechol borane.

The dye composition that can be used in the invention in general contains an amount of dye of formula (I) or formula (II) of between 0.001% and 50% relative to the total weight of the composition. Preferably, this amount is between 0.005% and 20% by weight, and even more preferably between 0.01% and 5% by weight, relative to the total weight of the composition.

The composition according to the invention may optionally comprise at least one additional disulphide or thiol dye as described in documents WO 2006/136617 and FR2876576.

By way of nonlimiting examples, a dye of formula (I) or (II) according to the invention which exhibits a maximum absorption between 560 and 630 nm is advantageously combined with a dye of general formula (III) (red azo disulphide dyes) and/or a dye of general formula (IV) (yellow hydrazone disulphide dyes) in proportions such that the colour obtained after application of the composition to hair, rinsing and drying, makes it possible to obtain an aesthetic coverage (natural, brown, with, where appropriate, coppery, iridescent, mahogany, matt, red, dark purple tints) which is sufficiently strong and stable.

The red azo disulphide dyes are in particular of general formula (III) below:

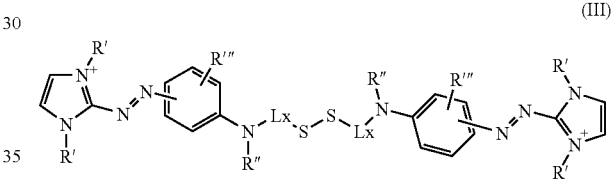

and also the addition salts thereof with an organic or mineral acid, and the solvates, hydrates, tautomers and geometrical isomers thereof;

in which formula (III):

R", independently of one another, represent a hydrogen atom or an NR""C(O)R"" group;

R', R''', R"" and R''''', independently of one another, represent a hydrogen atom or a group chosen from optionally substituted ($C_1$-$C_{14}$)alkyl, optionally substituted ($C_5$-$C_{10}$)cycloalkyl; optionally substituted ($C_2$-$C_{14}$)alkylenyl; optionally substituted ($C_5$-$C_{10}$)-aryl($C_1$-$C_{10}$)alkyl; optionally substituted ($C_1$-$C_{10}$)-alkyl($C_5$-$C_{10}$)aryl; and optionally substituted ($C_5$-$C_{10}$)-aryl;

Lx, independently of one another, represent an optionally substituted $C_1$-$C_{20}$, in particular $C_1$-$C_{10}$, divalent hydrocarbon-based chain optionally interrupted with one or more divalent groups or combinations thereof, it being understood that two divalent groups or combinations thereof are interrupted with a $C_2$-$C_6$ divalent hydrocarbon-based chain, in particular alkylene, said divalent groups being chosen from —N(R)—, —O—, —S— and —C(O)—, with R representing a hydrogen atom or a group chosen from $C_1$-$C_4$ alkyl, $C_2$-$C_6$ (poly)hydroxyalkyl, alkoxy($C_1$-$C_6$)alkyl, aryl such as phenyl, aryl($C_1$-$C_6$)alkyl such as benzyl, ($C_1$-$C_4$)alkyl-carbonylamino($C_1$-$C_6$)alkyl, amino($C_1$-$C_4$)alkyl, the amine of which is substituted with one or more $C_1$-$C_4$ alkyl radicals, which may be identical or different, ($C_1$-$C_6$)-alkylcarbonyl and ($C_1$-$C_4$)alkylcarbonylamino.

The "yellow" hydrazone disulphide dyes are in particular of general formula (IV) below:

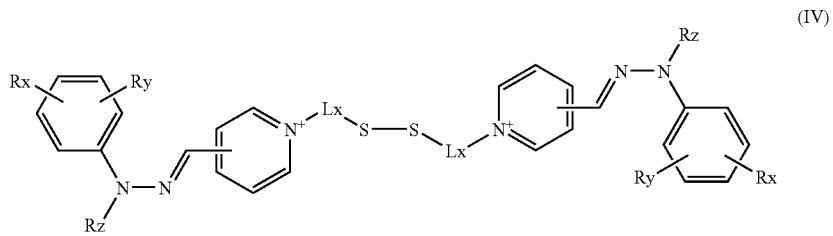

and also the addition salts thereof with an organic or mineral acid, and the solvates, hydrates, tautomers and geometrical isomers thereof;

in which formula (IV):
- Rx and Ry, independently of one another, represent a hydrogen atom, a halogen or a group chosen from optionally substituted $C_1$-$C_{16}$ alkyl optionally interrupted with one or more heteroatoms, and optionally substituted phenyl;
- Rz, independently of one another, represent a hydrogen atom or an NR''''C(O)R'''' group with R'''' and R'''' as defined above, and
- Lx are as defined above.

If they are present, the content of additional disulphide/thiol dye(s) in the composition generally ranges from 0.001% to 20% by weight relative to the weight of the composition, and preferably from 0.01% to 10% by weight relative to the weight of the composition.

The composition according to the invention may optionally comprise at least one additional direct dye different from the compounds of formula (I) and/or (II).

By way of nonlimiting examples, mention may be made of nitrobenzene dyes, azo, azomethine, methine, tetraazapentamethine, anthraquinone, naphthoquinone, benzoquinone, phenothiazine, indigoid, xanthene, phenanthridine or phthalocyanine dyes, those derived from triarylmethane, and natural dyes, alone or as mixtures.

It may, for example, be chosen from the following red or orange nitrobenzene dyes:
- 1-hydroxy-3-nitro-4-N-(γ-hydroxypropyl)aminobenzene,
- N-(β-hydroxyethyl)amino-3-nitro-4-aminobenzene,
- 1-amino-3-methyl-4-N-β-hydroxyethyl)amino-6-nitrobenzene,
- 1-hydroxy-3-nitro-4-N-(β-hydroxyethyl)aminobenzene,
- 1,4-diamino-2-nitrobenzene,
- 1-amino-2-nitro-4-methylaminobenzene,
- N-(β-hydroxyethyl)-2-nitro-para-phenylenediamine,
- 1-amino-2-nitro-4-(β-hydroxyethyl)amino-5-chlorobenzene,
- 2-nitro-4-aminodiphenylamine,
- 1-amino-3-nitro-6-hydroxybenzene,
- 1-(β-aminoethyl)amino-2-nitro-4-(β-hydroxyethyloxy)benzene,
- 1-(β,γ-dihydroxypropyl)oxy-3-nitro-4-(β-hydroxyethyl)aminobenzene,
- 1-hydroxy-3-nitro-4-aminobenzene,
- 1-hydroxy-2-amino-4,6-dinitrobenzene,
- 1-methoxy-3-nitro-4-(β-hydroxyethyl)aminobenzene,
- 2-nitro-4'-hydroxydiphenylamine,
- 1-amino-2-nitro-4-hydroxy-5-methylbenzene.

The additional direct dye may also be chosen from yellow and yellowy-green nitrobenzene direct dyes; mention may, for example, be made of the compounds chosen from:
- 1-β-hydroxyethyloxy-3-methylamino-4-nitrobenzene,
- 1-methylamino-2-nitro-5-(β,γ-dihydroxypropyl)-oxybenzene,
- 1-(β-hydroxyethyl)amino-2-methoxy-4-nitrobenzene,
- 1-(β-aminoethyl)amino-2-nitro-5-methoxybenzene,
- 1,3-di((3-hydroxyethyl)amino-4-nitro-6-chlorobenzene,
- 1-amino-2-nitro-6-methylbenzene,
- 1-(β-hydroxyethyl)amino-2-hydroxy-4-nitrobenzene,
- N-(β-hydroxyethyl)-2-nitro-4-trifluoromethylaniline,
- 4-(β-hydroxyethyl)amino-3-nitrobenzenesulphonic acid,
- 4-ethylamino-3-nitrobenzoic acid,
- 4-(β-hydroxyethyl)amino-3-nitrochlorobenzene,
- 4-(β-hydroxyethyl)amino-3-nitromethylbenzene,
- 4-(β,γ-dihydroxypropyl)amino-3-nitrotrifluoromethylbenzene,
- 1-(β-ureidoethyl)amino-4-nitrobenzene,
- 1,3-diamino-4-nitrobenzene,
- 1-hydroxy-2-amino-5-nitrobenzene,
- 1-amino-2-[tris(hydroxymethyl)methyl]amino-5-nitrobenzene,
- 1-(β-hydroxyethyl)amino-2-nitrobenzene,
- 4-(β-hydroxyethyl)amino-3-nitrobenzamide.

Mention may also be made of the blue or violet nitrobenzene direct dyes, for instance:
- 1-(β-hydroxyethyl)amino-4-N,N-bis(β-hydroxyethyl)amino-2-nitrobenzene,
- 1-(γ-hydroxypropyl)amino-4-N,N-bis(β-hydroxyethyl)amino-2-nitrobenzene,
- 1-(β-hydroxyethyl)amino-4-(N-methyl-N-(β-hydroxyethyl)amino-2-nitrobenzene,
- 1-(β-hydroxyethyl)amino-4-(N-ethyl-N-(β-hydroxyethyl)amino-2-nitrobenzene,
- 1-(β,γ-dihydroxypropyl)amino-4-(N-ethyl-N-(β-hydroxyethyl)amino-2-nitrobenzene,
- the 2-nitro-para-phenylenediamines of formula below:

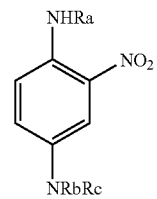

in which:
- Rb represents a $C_1$-$C_4$ alkyl radical, or a β-hydroxyethyl, β-hydroxypropyl or γ-hydroxypropyl radical;
- Ra and Rc, which may be identical or different, represent a β-hydroxyethyl, β-hydroxypropyl, γ-hydroxypropyl, or β,γ-dihydroxypropyl radical, at least one of the radicals Rb, Rc and Ra representing a γ-hydroxypropyl radical, and it being impossible for Rb and Rc to simultaneously denote a β-hydroxyethyl radical when Rb is a γ-hydroxypropyl radical, such as those described in French patent FR 2 692 572.

Among the azo direct dyes that can be used according to the invention, mention may be made of the cationic azo dyes described in patent applications WO 95/15144, WO 95/01772, EP 714954, FR 2 822 696, FR 2 825 702, FR 2 825 625, FR 2 822 698, FR 2 822 693, FR 2 822 694, FR 2 829 926, FR 2 807 650, WO 02/078660, WO 02/100834, WO 02/100369 and FR 2 844 269.

Among these compounds, mention may most particularly be made of the following dyes:
- 1,3-dimethyl-2-[[4-(dimethylamino)phenyl]azo]-1H-imidazolium chloride,
- 1,3-dimethyl-2-[(4-aminophenyl)azo]-1H-imidazolium chloride,
- 1-methyl-4-[(methylphenylhydrazono)methyl]-pyridinium methyl sulphate.

Among the azo direct dyes, mention may also be made of the following dyes, described in the Colour Index International, 3rd edition:
- Disperse Red 17
- Acid Yellow 9
- Acid Black 1
- Basic Red 22
- Basic Red 76
- Basic Yellow 57
- Basic Brown 16
- Acid Yellow 36
- Acid Orange 7
- Acid Red 33
- Acid Red 35
- Basic Brown 17
- Acid Yellow 23
- Acid Orange 24
- Disperse Black 9.

Mention may also be made of 1-(4'-aminodiphenylazo)-2-methyl-4-bis(β-hydroxyethyl)aminobenzene and 4-hydroxy-3-(2-methoxyphenylazo)-1-naphthalenesulphonic acid.

Among the quinone direct dyes, mention may be made of the following dyes:
- Disperse Red 15
- Solvent Violet 13
- Acid Violet 43
- Disperse Violet 1
- Disperse Violet 4
- Disperse Blue 1
- Disperse Violet 8
- Disperse Blue 3
- Disperse Red 11
- Acid Blue 62
- Disperse Blue 7
- Basic Blue 22
- Disperse Violet 15
- Basic Blue 99 and also the following compounds:
- 1-N-methylmorpholiniumpropylamino-4-hydroxyanthraquinone
- 1-aminopropylamino-4-methylaminoanthraquinone
- 1-aminopropylaminoanthraquinone
- 5-β-hydroxyethyl-1,4-diaminoanthraquinone
- 2-aminoethylaminoanthraquinone
- 1,4-bis(β,γ-dihydroxypropylamino)anthraquinone.

Among the azine dyes, mention may be made of the following compounds:
- Basic Blue 17
- Basic Red 2.

Among the triarylmethane dyes that can be used according to the invention, mention may be made of the following compounds:
- Basic Green 1
- Acid Blue 9
- Basic Violet 3
- Basic Violet 14
- Basic Blue 7
- Acid Violet 49
- Basic Blue 26
- Acid Blue 7.

Among the indoamine dyes that can be used according to the invention, mention may be made of the following compounds:
- 2-β-hydroxyethylamino-5-[bis(β-4'-hydroxyethyl)-amino]anilino-1,4-benzoquinone
- 2-β-hydroxyethylamino-5-(2'-methoxy-4'-amino)-anilino-1,4-benzoquinone
- 3-N-(2'-chloro-4'-hydroxy)phenylacetylamino-6-methoxy-1,4-benzoquinoneimine
- 3-N-(3'-chloro-4'-methylamino)phenylureido-6-methyl-1,4-benzoquinoneimine
- 3-[4'-N-(ethylcarbamylmethyl)amino]phenylureido-6-methyl-1,4-benzoquinoneimine.

The additional direct dye may also be a natural direct dye.

Among the natural direct dyes that can be used according to the invention, mention may be made of lawsone, juglone, alizarin, purpurin, carminic acid, kermesic acid, purpurogallin, protocatechaldehyde, indigo, isatin, curcumin, spinulosine and apigeninidin. Extracts or decoctions containing these natural dyes, and in particular henna-based extracts or poultices, may also be used.

If they are present, the content of additional direct dye(s) in the composition generally ranges from 0.001% to 20% by weight relative to the weight of the composition, and preferably from 0.01% to 10% by weight relative to the weight of the composition.

The dye composition may also contain one or more oxidation bases and/or one or more couplers conventionally used for dyeing keratin fibres.

Among the oxidation bases, mention may be made of para-phenylenediamines, bisphenylalkylenediamines, para-aminophenols, bis-para-aminophenols, ortho-aminophenols and heterocyclic bases, and addition salts thereof.

Among these couplers, mention may in particular be made of meta-phenylenediamines, meta-aminophenols, meta-diphenols, naphthalene couplers and heterocyclic couplers, and addition salts thereof.

The coupler(s) is (are each) generally present in an amount of between 0.001% and 10% by weight of the total weight of the dye composition, preferably between 0.005% and 6%.

The oxidation base(s) present in the dye composition is (are) in general (each) present in an amount of between 0.001% and 10% by weight of the total weight of the dye composition, preferably between 0.005% and 6% by weight.

In general, the addition salts of the oxidation bases and of the couplers that can be used in the context of the invention are in particular chosen from the addition salts with an acid, such as hydrochlorides, hydrobromides, sulphates, citrates, succinates, tartrates, lactates, tosylates, benzenesulphonates, phosphates and acetates, and the addition salts with a base, such as alkali metal hydroxides, for instance sodium hydroxide or potassium hydroxide, aqueous ammonia, amines or alkanolamines.

The medium suitable for dyeing, also known as dye support, is a cosmetic medium generally constituted of water or of a mixture of water and at least one organic solvent. By way of organic solvent, mention may, for example, be made of $C_1$-$C_4$ lower alkanols, such as ethanol and isopropanol; polyols and polyol ethers, such as 2-butoxyethanol, propylene glycol, propylene glycol monomethyl ether, diethylene glycol monoethyl ether and diethylene glycol monomethyl ether, and also aromatic alcohols such as benzyl alcohol or phenoxyethanol, and mixtures thereof.

When they are present, the solvents are preferably present in proportions of preferably between 1% and 40% by weight approximately, relative to the total weight of the dye composition, and even more preferably between 5% and 30% by weight approximately.

The dye composition may also contain various adjuvants conventionally used in compositions for dyeing the hair, such as anionic, cationic, nonionic, amphoteric or zwitterionic surfactants or mixtures thereof, anionic, cationic, nonionic, amphoteric or zwitterionic polymers or blends thereof, mineral or organic thickeners, and in particular anionic, cationic, nonionic and amphoteric associative polymeric thickeners, antioxidants, penetrating agents, sequestering agents, fragrances, buffers, dispersing agents, conditioning agents such as, for example, modified or unmodified, volatile or non-volatile silicones, such as amino silicones, film-forming agents, ceramides, preservatives, opacifiers or conductive polymers.

The above adjuvants are in general present in an amount, for each of them, of between 0.01% and 20% by weight relative to the weight of the composition.

Of course, those skilled in the art will take care to select this or these possible additional compound(s) in such a way that the advantageous properties intrinsically associated with the dye composition in accordance with the invention are not, or are not substantially, impaired by the addition(s) envisaged.

The pH of the dye composition is generally between 3 and 14 approximately, and preferably between 5 and 11 approximately. It may be adjusted to the desired value by means of acidifying or basifying agents normally used in the dyeing of keratin fibres, or alternatively by means of conventional buffer systems.

Among the acidifying agents, mention may, by way of example, be made of mineral or organic acids such as hydrochloric acid, orthophosphoric acid or sulphuric acid, carboxylic acids such as acetic acid, tartaric acid, citric acid or lactic acid, and sulphonic acids.

Among the basifying agents, mention may, by way of example, be made of aqueous ammonia, alkali metal carbonates, alkanolamines such as mono-, di- and triethanolamines and also their derivatives, sodium hydroxide or potassium hydroxide and the compounds of formula (γ) below:

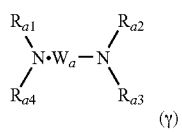

in which Wa is a propylene residue optionally substituted with a hydroxyl group or a $C_1$-$C_4$ alkyl radical; $R_{a1}$, $R_{a2}$, $R_{a3}$ and $R_{a4}$, which may be identical or different, represent a hydrogen atom, or a $C_1$-$C_4$ alkyl or $C_1$-$C_4$ hydroxyalkyl radical.

The dye composition may be in various forms, such as in the form of a liquid, a cream or a gel, or any other form suitable for dyeing keratin fibres, and in particular the hair.

According to a specific embodiment, in the process of the invention, a reducing agent can be applied as a pretreatment before the application of the composition containing at least one dye of formula (I) or (II).

This pretreatment may be of short duration, in particular from 0.1 second to 30 minutes, preferably from 1 minute to 15 minutes, with a reducing agent as mentioned above.

According to another process, the composition comprising at least one dye of formula (I) or (II) also contains at least one reducing agent as defined above. This composition is then applied to the hair.

According to a variant, the reducing agent is added to the dye composition containing at least one dye of formula (I) or (II), at the time of use.

According to another process, the composition comprising at least one dye of formula (I) or (II) also contains at least one reducing agent as defined above. This composition is then applied to the hair.

According to another variant, the reducing agent is applied post-treatment, after the application of the composition containing at least one dye of formula (I) or (II). The duration of the post-treatment with the reducing agent may be short, for example from 0.1 second to 30 minutes, preferably from 1 minute to 15 minutes, with a reducing agent as described above. According to a specific embodiment, the reducing agent is an agent of thiol or borohydride type as described above.

One specific embodiment of the invention relates to a process in which the dye of formula (I) or (II) can be applied directly to the hair without reducing agents, with no reducing pretreatment or reducing post-treatment.

A treatment with an oxidizing agent can optionally be combined. Any type of oxidizing agent that is conventional in the field may be used. Thus, it may be chosen from hydrogen peroxide, urea peroxide, alkali metal bromates, persalts such as perborates and persulphates, and also enzymes, among which mention may be made of peroxidases, 2-electron oxidoreductases such as uricases and 4-electron oxygenases such as laccases. The use of hydrogen peroxide is particularly preferred. The oxidant leave-on time may be between 0.01 and 40 minutes.

When the thiol dye of formula (I) or (II) for which x and y are 1 comprises a thiol-function-protecting group Y, the process of the invention comprises a deprotection step aimed at restoring the SH function in situ.

By way of example, it is possible to deprotect the S—Y function of the dyes of the invention which have a protecting group Y, by adjusting the pH as follows:

| Y: protecting group | Deprotection |
|---|---|
| alkylcarbonyl, | pH > 9 |
| arylcarbonyl, | pH > 9 |
| alkoxycarbonyl, | pH > 9 |
| aryloxycarbonyl, | pH > 9 |
| arylalkoxycarbonyl | pH > 9 |
| (di)(alkyl)aminocarbonyl, | pH > 9 |
| (alkyl)arylaminocarbonyl | pH > 9 |
| optionally substituted aryl such as phenyl, | pH > 9 |
| 5-, 6- or 7-membered monocyclic heteroaryl such as oxazolium | pH > 9 |
| 8- to 11-membered bicyclic heteroaryl such as benzoimidazolium, or benzoxazolium | pH > 9 |

The deprotection step may be carried out during a hair pretreatment step, for instance the reducing pretreatment of the hair.

According to a variant, the deprotection step may be carried out post-treatment or at the same time as the dyeing.

The application of the dye composition according to the invention is generally carried out at ambient temperature. It may, however, be carried out at temperatures ranging from 20 to 180° C.

A subject of the invention is also a multicompartment dyeing device or dyeing "kit" in which a first compartment contains a dye composition comprising at least one dye of formula (I) or (II), and a second compartment contains a reducing agent capable of reducing the disulphide functions of the keratin materials and/or of the disulphide dye of formula (I) or (II).

One of these compartments may also contain one or more other dyes of direct dye or oxidation dye type.

The invention also relates to a multicompartment device in which a first compartment contains a dye composition comprising at least one dye of formula (I) or (II); a second compartment contains a reducing agent capable of reducing the disulphide bond of the keratin materials and/or of the disulphide dye of formula (I) or (II); and a third compartment contains an oxidizing agent.

Alternatively, the dyeing device contains a first compartment containing a dye composition which comprises at least one protected thiol dye of formula (I) or (II) with x and y being 1, a second compartment containing an agent capable of deprotecting the protected thiol so as to free the thiol, and, optionally, a third compartment comprising an oxidizing agent.

Each of the devices mentioned above may be equipped with a means for delivering the desired mixture to the hair, for instance the devices described in patent FR 2 586 913.

The examples which follow serve to illustrate the invention without, however, being limiting in nature.

EXAMPLE 1

Synthesis Example (a) Synthesis of 4,4'-{disulphanediylbis[ethane-2,1-diylimino(6-chloro-1,3,5-triazine-4,2-diyl)imino-4,1-phenylene(E)diazene-2,1-diyl]}bis(1-ethylquinolinium)bis(ethyl sulphate)

Compound 1

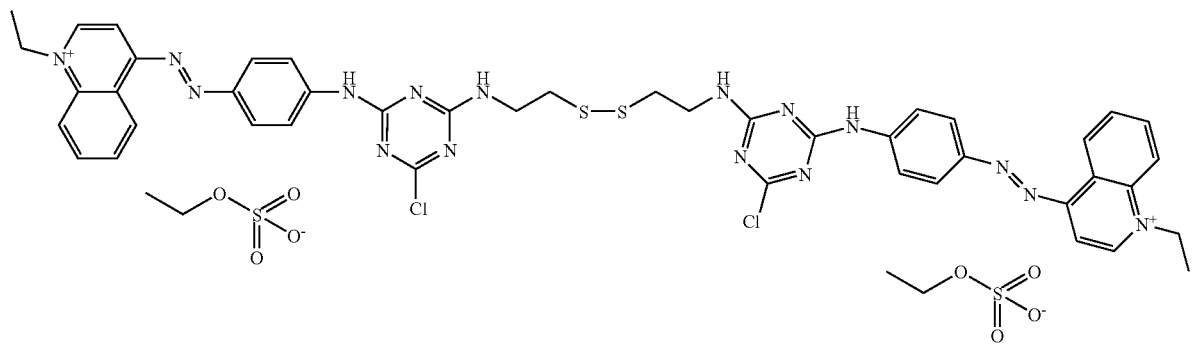

Synthesis Scheme

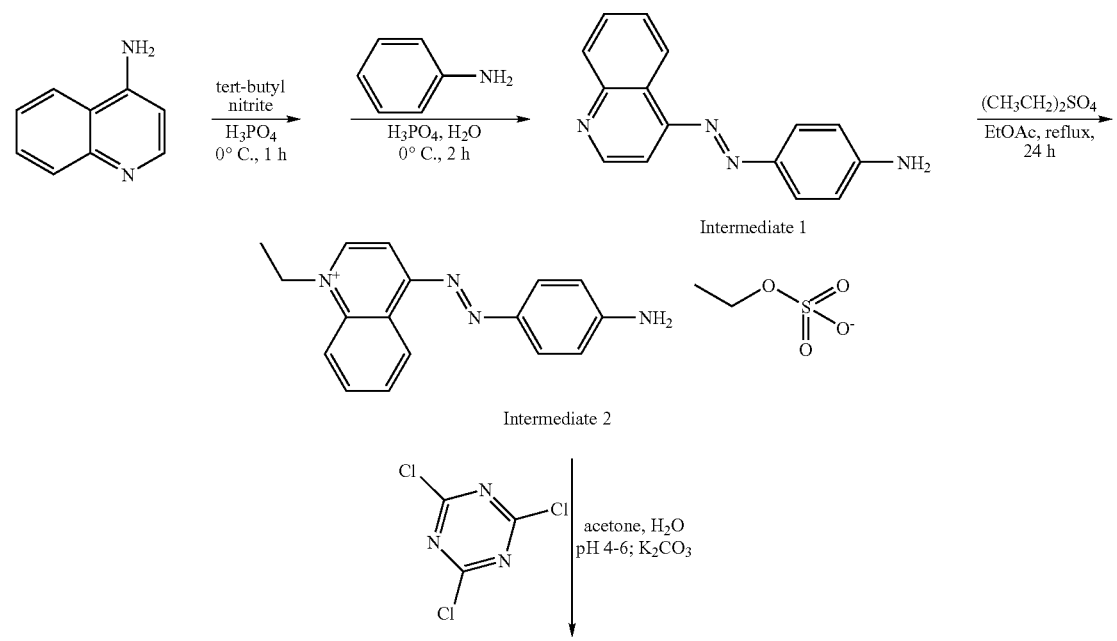

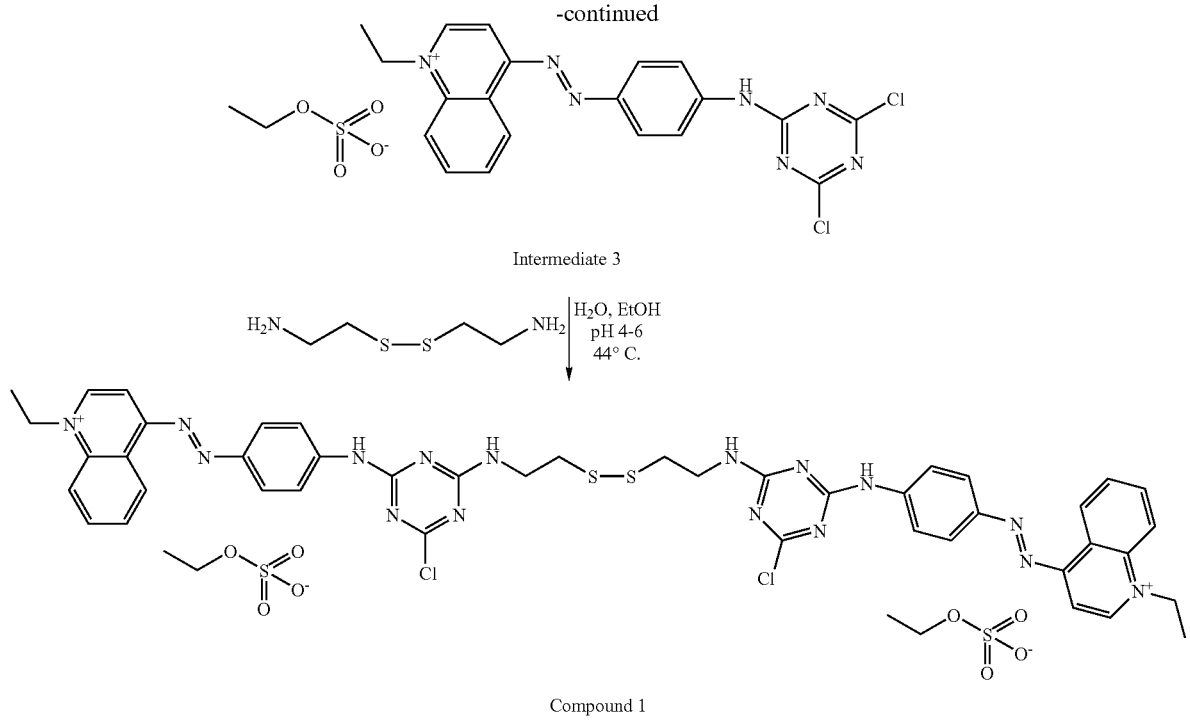

Intermediate 3

Compound 1

Intermediate 1 is obtained in the usual manner as follows: a solution of tert-butylnitrite is added dropwise to a solution of 4-aminoquinoline in $H_3PO_4$ at $-10°$ C. with stirring. After 1 h, a solution of urea and then a solution of aniline in $H_3PO_4$ and $H_2O$ are added. The reaction mixture is brought back to pH 7 with sodium hydroxide, at $0°$ C., and stirred for 2 h. After filtration, the solid is purified by chromatography (alumina).

Intermediate 1 and a stoichiometric amount of diethyl sulphate are refluxed for 24 h in ethyl acetate. After the solvent has been evaporated off, the 4-[(4-aminophenyl)diazenyl-1-ethylquinolinium] 2-(ethyl sulphate) compound is purified by chromatography (alumina).

A solution containing 4-[(E)-(4-aminophenyl)diazenyl]-1-ethylquinolinium ethyl sulphate (1 g), water (50 ml) and ethanol (50 ml) is added to a solution of 2,4,6-trichloro-1,3,5-triazine (0.46 g), acetone (25 ml) and ice-cold water (50 ml), while keeping the pH between 4-6 by adding a saturated solution of $K_2CO_3$ and keeping a temperature of between 0-5° C. After the addition, the reaction medium is allowed to return slowly to ambient temperature while maintaining the pH thereof at between 4 and 6 with a saturated solution of $K_2CO_3$. After stirring of the mixture at ambient temperature for 12 h and at pH 4-6, a solution of cysteamine dihydrochloride (280 mg) solubilized in water (25 ml) and absolute ethanol (25 ml) is slowly added to said mixture, at AT (18° C.), always taking care to keep the pH of the reaction medium between 4 and 6. The mixture is heated for one hour at 44° C. The pH is always maintained between 4 and 6 by adding a saturated solution of $K_2CO_3$ to the reaction medium. After slow cooling to ambient temperature, the mixture is poured into acetone (1 L), filtered and dried under vacuum, so as to recover a violet powder (310 mg). The analysis shows that compound 1 is in conformity (LC-MS m/z=465).

(b) Synthesis of 1,1'-{disulfanediylbis[ethane-2,1-diylimino(4-oxobutane-4,1-diyl)]}bis{4-[{4-[bis(2-hydroxyethyl)amino]phenyl}diazenyl]-quinolinium}dichloride compound 50

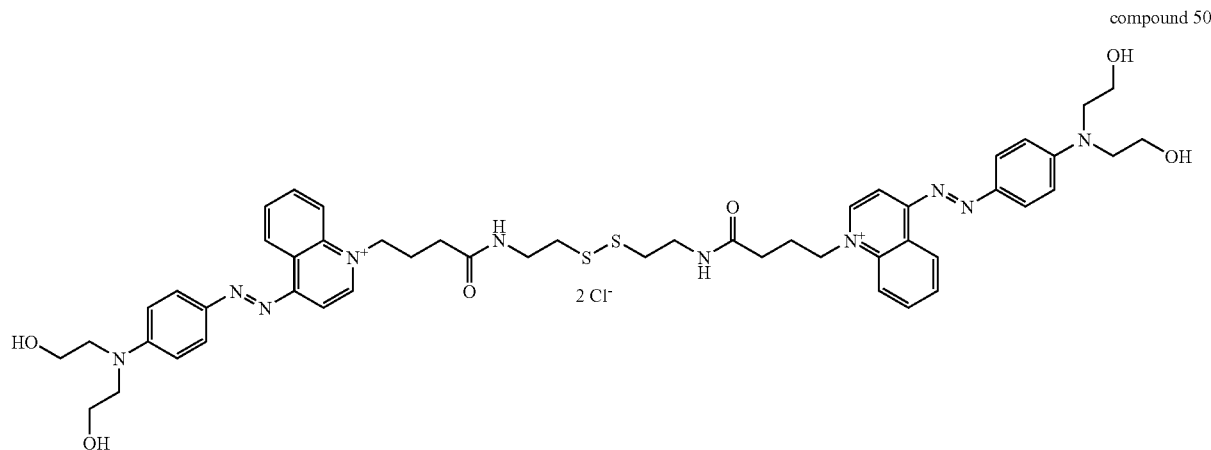

Synthesis Scheme

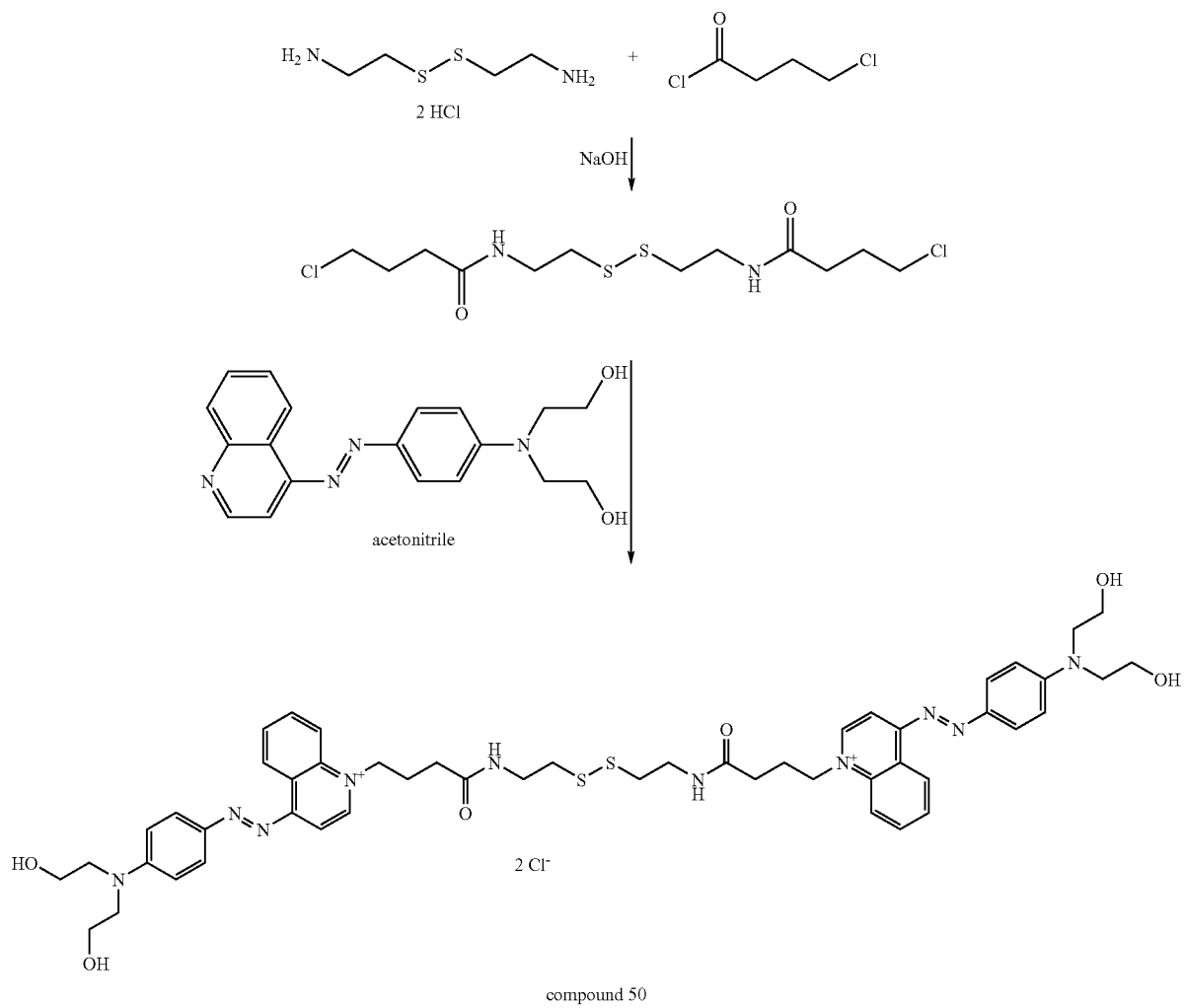

compound 50

Step 1: synthesis of N,N'-(disulfanediyldiethane-2,1-diyl)bis(4-chlorobutanamide)

60 g of cystamine hydrochloride are solubilized in 500 mL and cooled to 5° C. pH is raised to 10 by addition of aq. NaOH (30%). A solution of 4-chlorobutanoyl chloride (105 g) in anhydrous THF (500 mL), is added dropwise, while pH is maintained above 7 by addition of aq. NaOH (30%). After completion of the addition and stabilization of pH at 7, the mixture is kept mixing for 3 d. The aqueous layer is extracted with 3×500 mL dichloromethane, combined with THF layer and dried over Na2SO4. After drying under vacuum, 41 g of a white powder are collected. Analyses are in accordance with the expected structure.

Step 2: Synthesis of 1,1'-{disulfanediylbis[ethane-2,1-diylimino(4-oxobutane-4,1-diyl)]}bis{4-[{4-[bis(2-hydroxyethyl)amino]phenyl}diazenyl]quinolinium}dichloride 0.35 g of 2,2'-({4-[(quinolin-4-yl)diazenyl]-phenyl}-imino)diethanol and 0.18 g of N,N'-(disulfanediyldiethane-2,1-diyl)bis(4-chlorobutanamide) are solubilized in 2 mL acetonitrile. The mixtured is heated at reflux for 24 h, cooled and poured on 50 mL acetone. The resulting oil is washed several times with acetone.

Dyeing Process—Compound [1]

Preparation of a Composition A

| | |
|---|---|
| Compound [1] | 0.3 g |
| Benzyl alcohol | 4 g |
| Polyethylene glycol 6EO | 6 g |
| Hydroxyethylcellulose | 0.7 g |
| Alkylpolyglucoside as an aqueous solution containing 65% AM | 4.5 g |
| Demineralized water | qs 100 g |

Preparation of a Composition B

| | |
|---|---|
| Thioglycolic acid | 1M |
| Sodium hydroxide | qs pH 8.5 |
| Demineralized water | qs 100 g |

First Dyeing Process:
One-Step Application

At the time of use, compositions A (9 ml) and B (1 ml) are mixed, and then the formulations are applied to locks of natural white hair containing 90% white hairs (NW), and of permanent-waved white hair (PW). The leave-on time is 20 minutes at ambient temperature. The locks are then rinsed, shampooed and dried.

Second Dyeing Process:
Two-Step Application

Composition A is applied to locks of natural white hair containing 90% white hairs (NW), and of permanent-waved white hair (PW). The leave-on time is 10 minutes at ambient temperature. The locks thus treated are rinsed with water.

Composition B is then applied to these same locks, in a bath ratio of 5 g of formulation per gram of hair. The leave-on time is 15 minutes at ambient temperature. The locks are then rinsed, shampooed and dried.

In the two cases, strong colouring is obtained on the NW and PW white hair.

Study of Light-Fastness and Shampoo-Fastness:

A study of light-fastness was carried out, by exposure to the Xenotest, on the locks of natural white and permanent-waved white hair previously dyed according to the two dyeing processes mentioned above, for a duration of 3 hours. The exposure conditions are 90 W/m$^2$, 60% relative humidity and with an exposure chamber temperature of 35° C.

Once treated according to the two dyeing processes above, the locks are shampooed according to 5 shampooing cycles comprising a shampooing operation followed by rinsing with running water and, finally, air-drying. These cycles are carried out 5 times one after the other. During the shampooing operations, there is no visible running, the shampoo foam and the rinsing water are not coloured.

It appears, visually, that the colourings obtained according to the two processes withstand jointly exposure to light and to shampooing operations.

The invention claimed is:

1. A dye chosen from dyes of formula (I), dyes of formula (II):

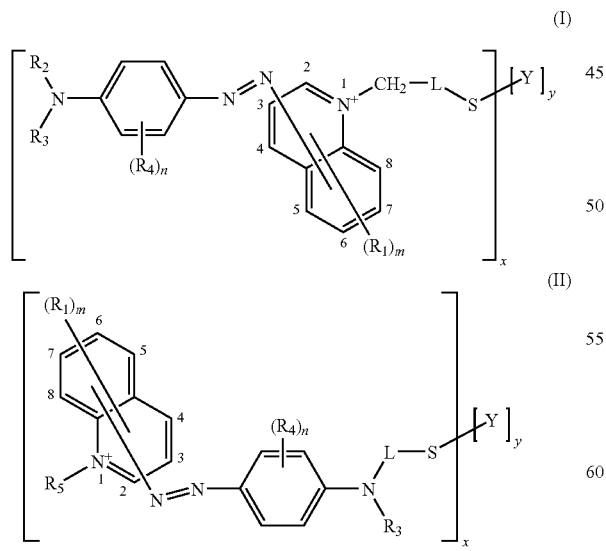

organic acid addition salts, mineral acid addition salts, solvates, tautomers, optical isomers, and geometrical isomers thereof;

wherein, in formula (I) and formula (II):
L is chosen from optionally substituted $C_1$-$C_{20}$ divalent hydrocarbon-based chains optionally interrupted with at least one divalent group, it being understood that two divalent groups or combinations thereof are separated by a $C_1$-$C_6$ divalent hydrocarbon-based chain, said at least one divalent group being chosen from:
—N(R)—; —N$^+$(R)(R$^0$)-An$^-$; —O—, —S—, —C(O)—, with R chosen from $C_1$-$C_4$ alkyl groups, $C_2$-$C_6$ (poly)hydroxyalkyl groups, alkoxy ($C_1$-$C_6$) alkyl groups, aryl groups, aryl ($C_1$-$C_6$)alkyl groups, ($C_1$-$C_4$)alkylcarbonylamino ($C_1$-$C_6$)alkyl groups, amino ($C_1$-$C_4$)alkyl groups, the amine of which is substituted with at least one $C_1$-$C_4$ alkyl group which may be identical or different, ($C_1$-$C_6$) alkylcarbonyl groups, and ($C_1$-$C_4$)alkylcarbonylamino groups; and R$^0$ is chosen from hydrogen and R;
cationic heterocyclic and heteroaryl Het$^+$An$^-$ groups, with An$^-$ chosen from anionic counterions, and
Het$^+$ chosen from saturated and unsaturated cationic heterocycles comprising 5 to 10 members and saturated and unsaturated cationic heteroaryls comprising 5 to 10 members;
noncationic heterocyclic groups comprising 5 to 10 members; and
optionally substituted (hetero)aryl groups;
with L comprising no diazo, hydrazino, aminooxy, nitro, nitroso or peroxide groups;
$R_1$ and $R_4$, independently of one another, are each chosen from:
$C_1$-$C_4$ alkyl groups;
hydroxyl groups;
$C_1$-$C_4$ alkoxy groups;
$C_2$-$C_4$ (poly)hydroxyalkoxy groups;
alkoxycarbonyl groups ($R_aO$—C(O)—) in which $R_a$ is chosen from $C_1$-$C_4$ alkyl groups;
alkylcarbonyloxy groups ($R_aC(O)$—O—) in which $R_a$ is chosen from $C_1$-$C_4$ alkyl groups;
amino groups optionally substituted with at least one $C_1$-$C_4$ alkyl group, which may be identical or different, optionally bearing at least one hydroxyl group, it being possible for the two alkyl groups to optionally form, with the nitrogen atom to which they are attached, a substituted or unsubstituted 5- or 6-membered heterocycle optionally bearing another heteroatom identical to or different from nitrogen;
alkylcarbonylamino groups ($R_aC(O)$—NR'$_a$—) in which $R_a$ is chosen from $C_1$-$C_4$ alkyl groups and R'$_a$ is chosen from hydrogen and $C_1$-$C_4$ alkyl groups;
(di)(alkyl)aminocarbonyl groups (($R_a$)$_2$N—C(O)) in which the $R_a$ groups, which may be identical or different, are each chosen from hydrogen and $C_1$-$C_4$ alkyl groups;
ureido groups (($R_a$)$_2$N—C(O)—NR$_b$—) in which the $R_a$ and $R_b$ groups, independently of one another, are each chosen from hydrogen and $C_1$-$C_4$ alkyl groups;
guanidinium groups (($R_a$)$_2$N—C(=NH$_2^+$)—NR$_b$—) in which the $R_a$ and $R_b$ groups, independently of one another, are each chosen from hydrogen and $C_1$-$C_4$ alkyl groups;
halogens;
or else two adjacent $R_4$ groups can form, with the carbon atoms to which they are attached, a condensed, aromatic 6-membered ring optionally substituted with at least one group, which may be identical or different, chosen from hydroxyl groups, $C_1$-$C_4$ alkyl groups, hydroxycarbonyl groups (HO(O)C—), alkoxycarbonyl groups ($R_aO(O)C$—) in which $R_a$ is chosen from $C_1$-$C_4$ alkyl groups, (alkyl)sulphonylamino groups ($R_aS(O)_2NR_b$) in which $R_a$ is chosen from $C_1$-$C_4$ alkyl groups and $R_b$ is chosen from hydrogen and $C_1$-$C_4$ alkyl groups; $C_1$-$C_4$ alkoxy groups; amino groups optionally substituted with at least one $C_1$-$C_4$ alkyl group, which may be identical or different, and optionally bearing at least one hydroxyl or methylcarbonylamino group, it being possible for the two alkyl groups to optionally form, with the nitrogen atom to which they are attached, a 5- or 6-membered heterocycle optionally bearing another heteroatom identical to or different from nitrogen;

$R_2$ and $R_3$, independently of one another, are each chosen from:

hydrogen;

optionally substituted $C_1$-$C_6$ alkyl groups;

optionally substituted aryl groups;

optionally substituted heteroaryl groups;

optionally substituted aryl ($C_1$-$C_6$)alkyl groups;

optionally substituted heteroaryl ($C_1$-$C_6$)alkyl groups;

cycloalkyl($C_1$-$C_6$)alkyl groups;

heterocycloalkyl($C_1$-$C_6$)alkyl groups;

or else $R_3$, with the nitrogen atom which bears it, and $R_4$, with the carbon atom which bears it, can optionally together form a 5-, 6- or 7-membered heterocycle; this heterocycle and the aromatic ring attached to the azo group are then condensed; the heterocycle may be saturated or unsaturated, and optionally interrupted with a heteroatom;

or else two contiguous $R_2$ groups, when n is 2, form, together with the carbon atom which bears them, a benzo group;

or else $R_2$ and $R_3$ of formula (I) form, together with the nitrogen atom which bears them, a 5-, 6-, or 7-membered heterocycle;

$R_5$ is directly attached to the quaternized nitrogen atom by means of a carbon atom and is chosen from:

optionally substituted $C_1$-$C_6$ alkyl groups;

optionally substituted aryl groups;

optionally substituted heteroaryl groups;

optionally substituted aryl ($C_1$-$C_6$)alkyl groups;

optionally substituted heteroaryl($C_1$-$C_6$)alkyl groups;

cycloalkyl($C_1$-$C_6$)alkyl groups; and heterocycloalkyl($C_1$-$C_6$)alkyl groups;

Y is chosen from:

hydrogen;

alkali metals;

alkaline earth metals;

ammonium groups $N^+R^\alpha R^\beta R^\gamma R^\delta$ and phosphonium groups $P^+R^\alpha R^\beta R^\gamma R^\delta$, with $R^\alpha$, $R^\beta$, $R^\gamma$, and $R^\delta$, independently of one another, each chosen from hydrogen and ($C_1$-$C_4$)alkyl groups; and thiol-function-protecting groups;

An is chosen from anionic counterions;

m is chosen from integers ranging from 0 to 6 inclusive;

n is chosen from integers ranging from 0 to 4 inclusive;

x is 1 or 2;

y is 0 or 1;

it being understood that:

if x is 1, then y is 1 and that if x is 2, then y is zero;

the electroneutrality of the dyes of formula (I) and the dyes of formula (II) is ensured by at least one cosmetically acceptable anionic counterion An, which may or may not be identical.

2. The dye according to claim 1, wherein $R_1$ and $R_4$, independently of one another, are each chosen from:

amino groups optionally substituted with at least one $C_1$-$C_4$ alkyl group, which may be identical or different, optionally bearing at least one hydroxyl group, it being possible for the two alkyl groups to optionally form, with the nitrogen atom to which they are attached, a substituted or unsubstituted 5- or 6-membered heterocycle optionally bearing oxygen;

chlorine;

fluorine; and bromine.

3. A dye according to claim 1, wherein x and y are 1, and Y is chosen from hydrogen and alkali metals.

4. A dye according to claim 1, wherein x and y are 1, and Y is chosen from protecting groups.

5. A dye according claim 4, wherein Y chosen from the following protecting groups:

($C_1$-$C_4$)alkylcarbonyl groups;

($C_1$-$C_4$)alkylthiocarbonyl groups;

($C_1$-$C_4$)alkoxycarbonyl groups;

($C_1$-$C_4$)alkoxythiocarbonyl groups;

($C_1$-$C_4$)alkylthiothiocarbonyl groups;

(di)($C_1$-$C_4$) (alkyl)aminocarbonyl groups;

(di)($C_1$-$C_4$) (alkyl)aminothiocarbonyl groups;

arylcarbonyl groups;

aryloxycarbonyl groups;

aryl ($C_1$-$C_4$) alkoxycarbonyl groups;

(di)($C_1$-$C_4$) (alkyl)aminocarbonyl groups;

($C_1$-$C_4$) (alkyl)arylaminocarbonyl groups;

carboxyl groups;

$SO_3^-M^+$ groups, with $M^+$ chosen from alkali metals or $An^-$ and $An^{t-}$ groups of formula (I) or formula (II);

optionally substituted aryl groups;

optionally substituted heteroaryl groups;

optionally cationic, optionally substituted heterocycloalkyl groups;

groups of the following formula:

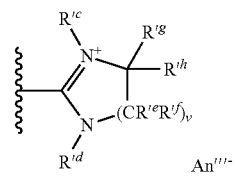

with $R'^c$, $R'^d$, $R'^e$, $R'^f$, $R'^g$, and $R'^h$, independently of one another, each chosen from hydrogen and ($C_1$-$C_4$)alkyl groups, or two groups $R'^g$ with $R'^h$ and/or $R'^e$ with $R'^f$ form an oxo or thioxo group or $R'^g$ with $R'^e$ together form a cycloalkyl group; and v is an integer ranging from 1 to 3 inclusive, and An'''⁻ is chosen from counterions;

—C(NR'ᶜR'ᵈ)=N⁺R'ᵉR'ᶠAn'''⁻ groups, with R'ᶜ, R'ᵈ, R'ᵉ and R'ᶠ, which may be identical or different, are each chosen from hydrogen and (C₁-C₄)alkyl groups, and An'''⁻ is chosen from counterions;

—C(NR'ᶜR'ᵈ)=NR'ᵉ, with R'ᶜ, R'ᵈ and R'ᵉ as defined above;

optionally substituted (di)aryl (C₁-C₄)alkyl groups;

optionally substituted (di)heteroaryl (C₁-C₄)alkyl groups;

CR₁R₂R₃, with R₁, R₂, and R₃, which may be identical or different, chosen from halogens;

(C₁-C₄)alkyl groups;

(C₁-C₄)alkoxy groups;

optionally substituted aryl groups;

optionally substituted heteroaryl groups;

P(Z¹)R'¹R'²R'³ groups, with R'¹ and R'², which may be identical or different, each chosen from hydroxyl groups, (C₁-C₄) alkoxy groups, and alkyl groups, R'³ chosen from hydroxyl groups and (C₁-C₄) alkoxy groups, and Z¹ chosen from oxygen and sulphur;

sterically hindered cyclic groups; and optionally substituted alkoxyalkyl groups.

6. A dye according to claim 1, wherein x is 2 and y is 0.

7. A dye according to claim 1 chosen from formulae (Ia) to (If), (IIa) and (IIb):

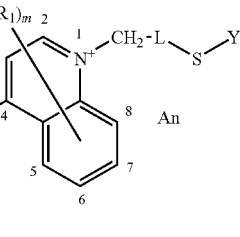

(Ia)

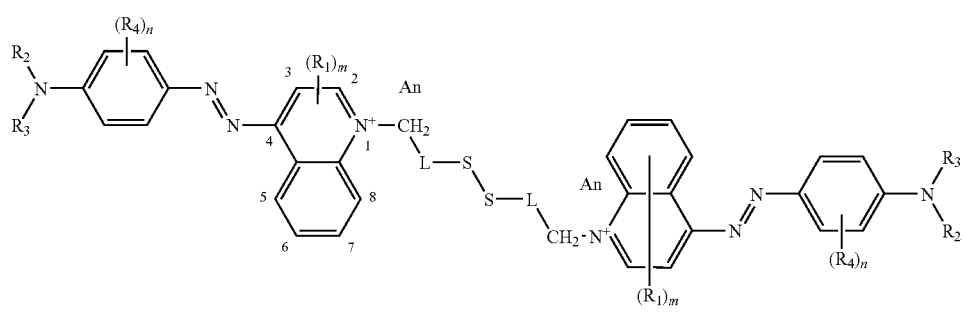

(Ib)

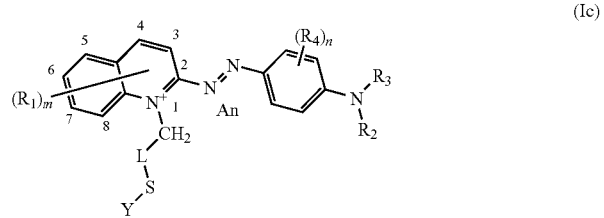

(Ic)

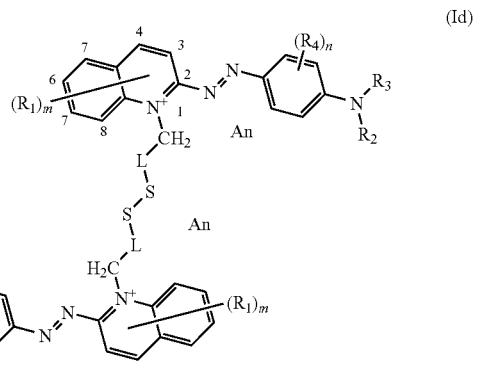

(Id)

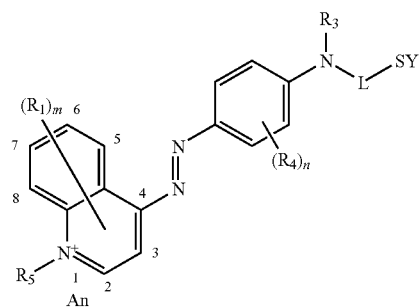

(IIa)

-continued

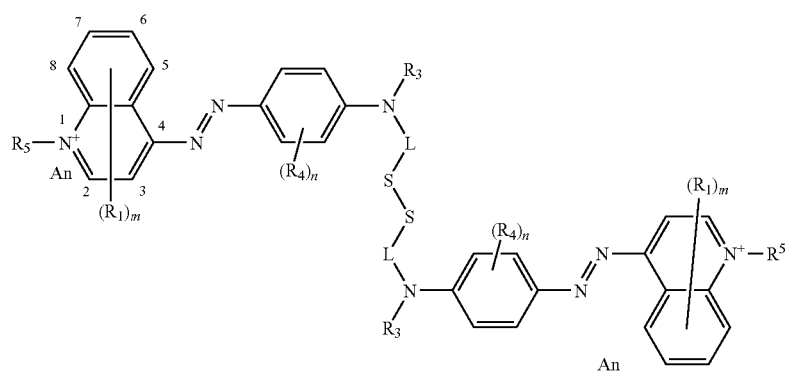

(IIb)

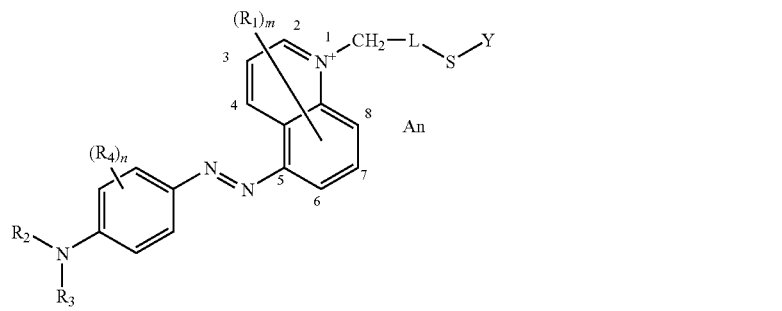

(Ie)

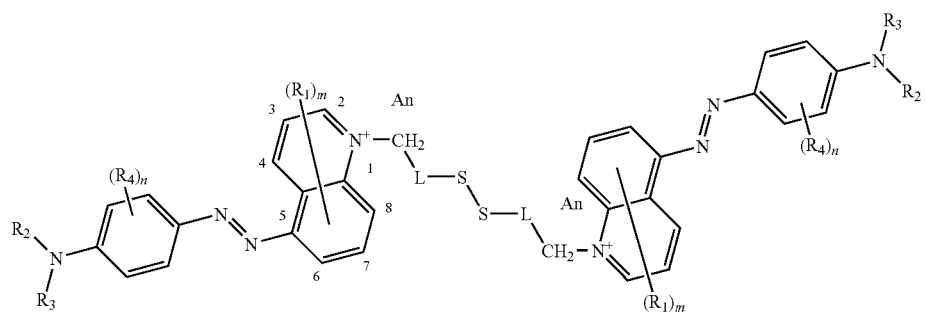

(If)

wherein

- L is chosen from optionally substituted $C_1$-$C_{20}$ divalent hydrocarbon-based chains optionally interrupted with at least one divalent group, it being understood that two divalent groups or combinations thereof are separated by a $C_1$-$C_6$ divalent hydrocarbon-based chain, said at least divalent group is chosen from:

—N(R)—; —N$^+$(R)(R$^0$)-An$^-$; —O—, —S—, —C(O)—, with R chosen from $C_1$-$C_4$ alkyl groups, $C_2$-$C_6$ (poly) hydroxyalkyl groups, alkoxy ($C_1$-$C_6$) alkyl groups, aryl groups, aryl ($C_1$-$C_6$)alkyl groups, ($C_1$-$C_4$)alkylcarbonylamino ($C_1$-$C_6$)alkyl groups, amino ($C_1$-$C_4$)alkyl groups, the amine of which is substituted with at least one $C_1$-$C_4$ alkyl group which may be identical or different, ($C_1$-$C_6$)alkylcarbonyl groups, and ($C_1$-$C_4$)alkylcarbonylamino groups; and R$^0$ is chosen from hydrogen and R;

cationic heterocyclic and cationic heteroaryl Het$^+$An$^-$ groups, with An$^-$ chosen from anionic counterions, and Het$^+$ chosen from saturated and unsaturated cationic heterocycles comprising 5 to 10 members and saturated and unsaturated cationic heteroaryls comprising 5 to 10 members;

noncationic heterocycles comprising 5 to 10 members, and optionally substituted (hetero)aryl groups;

with L comprising no diazo, hydrazino, aminooxy, nitro, nitroso or peroxide groups;

- $R_1$ and $R_4$, independently of one another, are each chosen from:

$C_1$-$C_4$ alkyl groups;

hydroxyl groups;

$C_1$-$C_4$ alkoxy groups;

$C_2$-$C_4$ (poly)hydroxyalkoxy groups;

alkoxycarbonyl groups ($R_aO$—C(O)—) in which $R_a$ is chosen from $C_1$-$C_4$ alkyl groups;

alkylcarbonyloxy groups ($R_aC(O)$—O—) in which $R_a$ is chosen from $C_1$-$C_4$ alkyl groups;

amino groups optionally substituted with at least one $C_1$-$C_4$ alkyl group, which may be identical or different, optionally bearing at least one hydroxyl group, it being possible for the two alkyl groups to optionally form, with the nitrogen atom to which they are attached, a substituted or unsubstituted 5- or 6-membered heterocycle optionally bearing another heteroatom identical to or different from nitrogen;

alkylcarbonylamino groups ($R_aC(O)-NR'_a-$) in which $R_a$ is chosen from $C_1$-$C_4$ alkyl groups and $R'_a$ is chosen from hydrogen and $C_1$-$C_4$ alkyl groups;

(di)(alkyl)aminocarbonyl groups $((R_a)_2N-C(O))$ in which the $R_a$ groups, which may be identical or different, are each chosen from hydrogen and $C_1$-$C_4$ alkyl groups;

ureido groups $((R_a)_2N-C(O)-NR_b-)$ in which the $R_a$ and $R_b$ groups, independently of one another, are each chosen from hydrogen and $C_1$-$C_4$ alkyl groups;

guanidinium groups $((R_a)_2N-C(=NH_2^+)-NR_b-)$ in which the $R_a$ and $R_b$ groups, independently of one another, are each chosen from hydrogen and $C_1$-$C_4$ alkyl groups;

halogens;

or else two adjacent $R_4$ groups can form, with the carbon atoms to which they are attached, a condensed, aromatic 6-membered ring optionally substituted with at least one group, which may be identical or different, chosen from hydroxyl groups, $C_1$-$C_4$ alkyl groups, hydroxycarbonyl (HO(O)C—) groups, alkoxycarbonyl ($R_aO(O)C-$) groups in which $R_a$ is chosen from $C_1$-$C_4$ alkyl groups, (alkyl)sulphonylamino groups ($R_aS(O)_2NR_b$) in which $R_a$ is chosen from $C_1$-$C_4$ alkyl groups and $R_b$ is chosen from hydrogen and $C_1$-$C_4$ alkyl groups; $C_1$-$C_4$ alkoxy groups; amino groups optionally substituted with at least one $C_1$-$C_4$ alkyl group, which may be identical or different, and optionally bearing at least one hydroxyl or methylcarbonylamino group, it being possible for the two alkyl groups to optionally form, with the nitrogen atom to which they are attached, a 5- or 6-membered heterocycle optionally bearing another heteroatom identical to or different from nitrogen;

$R_2$ and $R_3$, independently of one another, are each chosen from:
hydrogen;
optionally substituted $C_1$-$C_6$ alkyl groups;
optionally substituted aryl groups;
optionally substituted heteroaryl groups;
optionally substituted aryl ($C_1$-$C_6$)alkyl groups;
optionally substituted heteroaryl ($C_1$-$C_6$)alkyl groups;
cycloalkyl($C_1$-$C_6$)alkyl groups;
heterocycloalkyl($C_1$-$C_6$)alkyl groups;
or else $R_3$, with the nitrogen atom which bears it, and $R_4$, with the carbon atom which bears it, can optionally together form a 5-, 6- or 7-membered heterocycle; this heterocycle and the aromatic ring attached to the azo group are then condensed; the heterocycle may be saturated or unsaturated, and optionally interrupted with a heteroatom;
or else two contiguous $R_2$ groups, when n is 2, form, together with the carbon atom which bears them, a benzo group;
or else $R_2$ and $R_3$ of formula (I) form, together with the nitrogen atom which bears them, a 5-, 6-, or 7-membered heterocycle;

$R_5$ is directly attached to the quaternized nitrogen atom by means of a carbon atom and is chosen from:
optionally substituted $C_1$-$C_6$ alkyl groups;
optionally substituted aryl groups;
optionally substituted heteroaryl groups;
optionally substituted aryl ($C_1$-$C_6$)alkyl groups;
optionally substituted heteroaryl($C_1$-$C_6$)alkyl groups;
cycloalkyl($C_1$-$C_6$)alkyl groups; and
heterocycloalkyl($C_1$-$C_6$)alkyl groups;

An is chosen from anionic counterions;
m is chosen from integers ranging from 0 and 6 inclusive;
n is chosen from integers ranging from 0 and 4 inclusive.

8. A dye according claim 1, wherein said dye is chosen from structures (1) to (50):

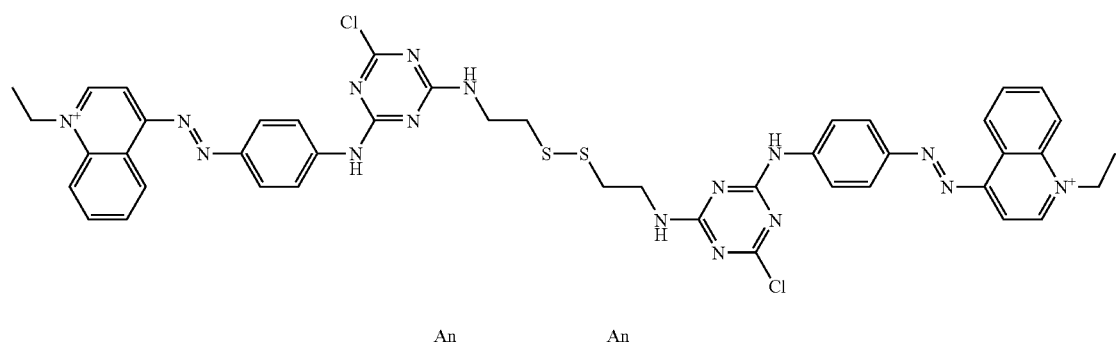

1

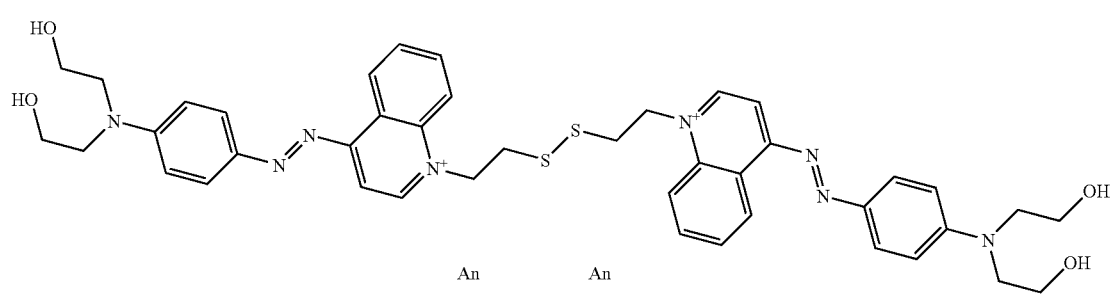

2

3
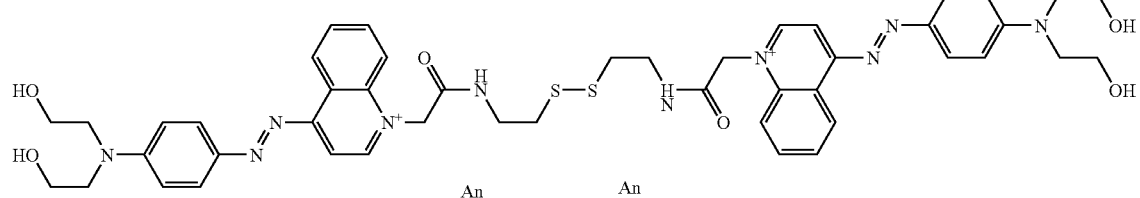
4
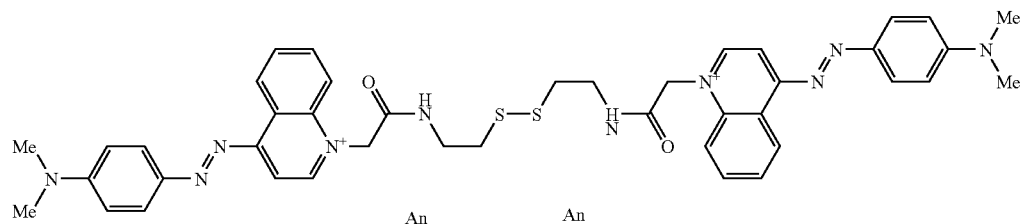
5
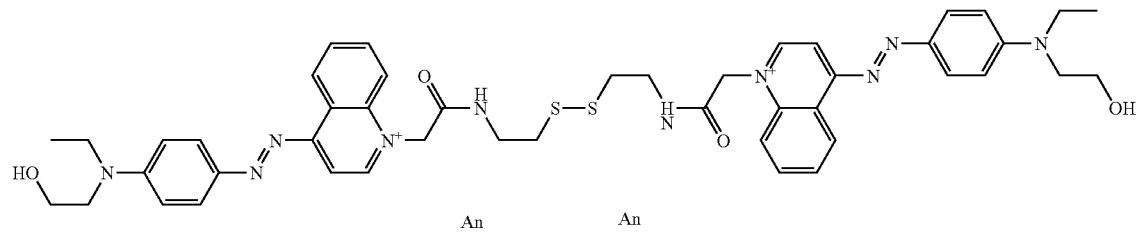
6
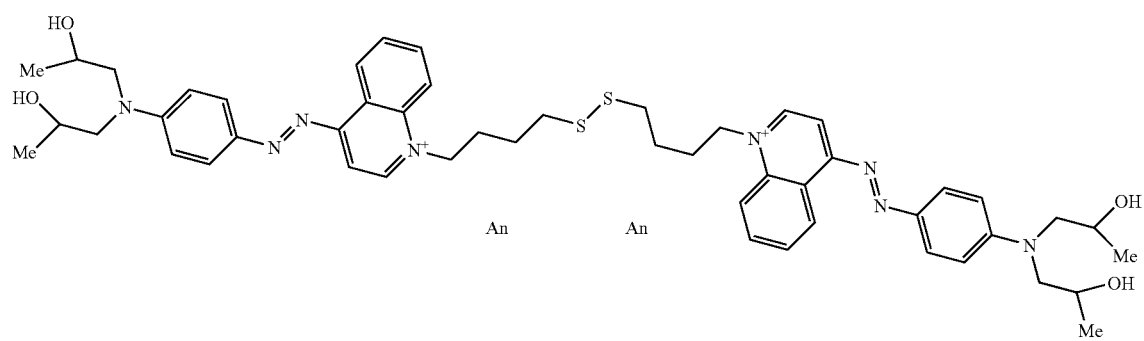
7
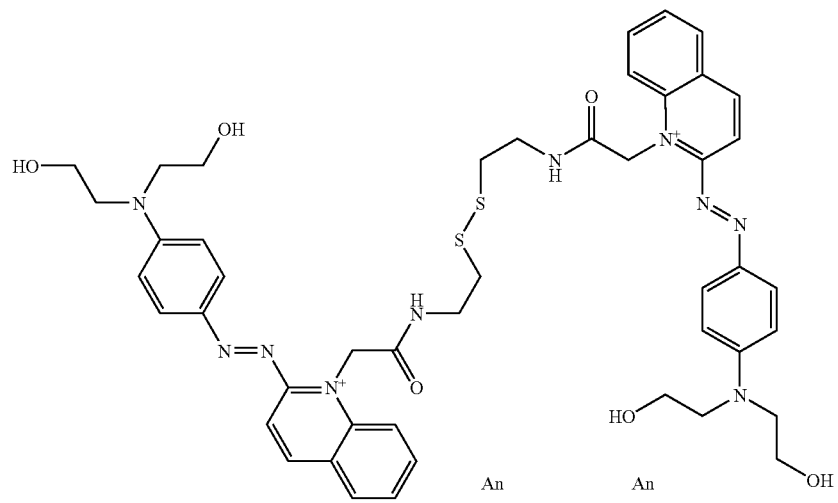

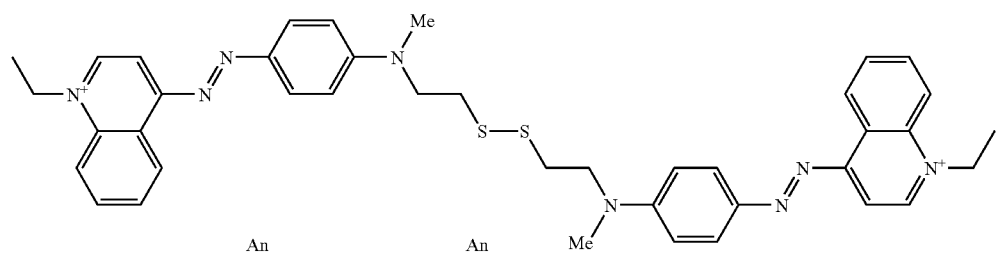
8
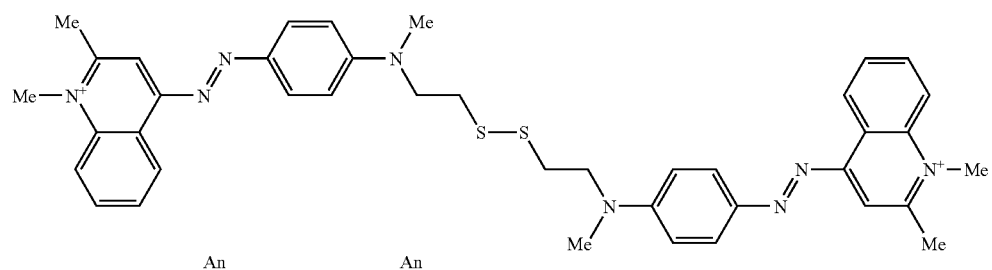
9
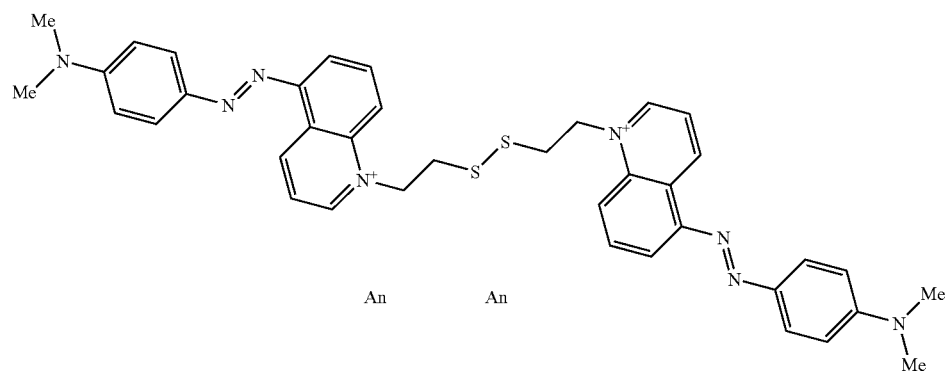
10
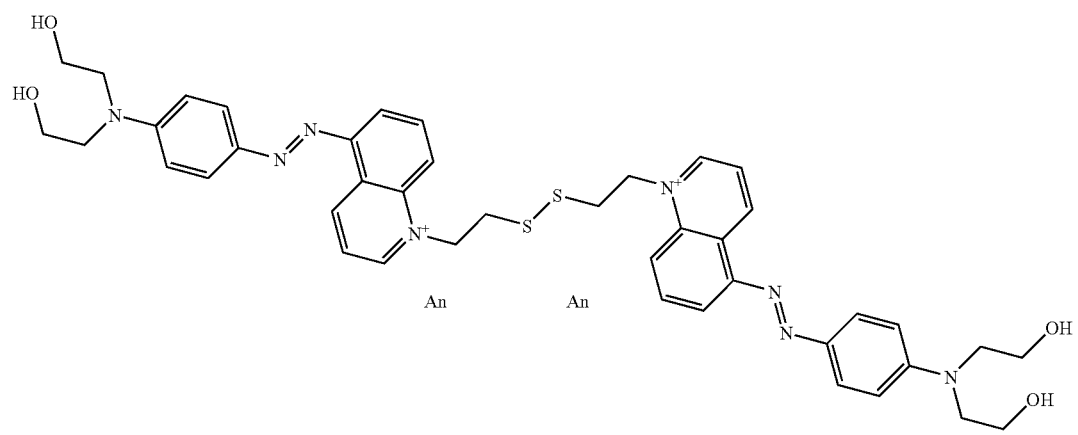
11
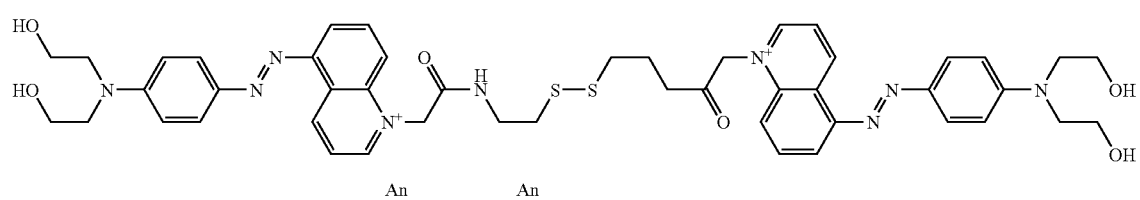
12

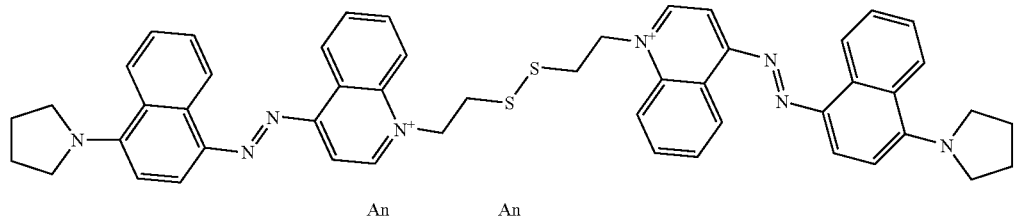
13
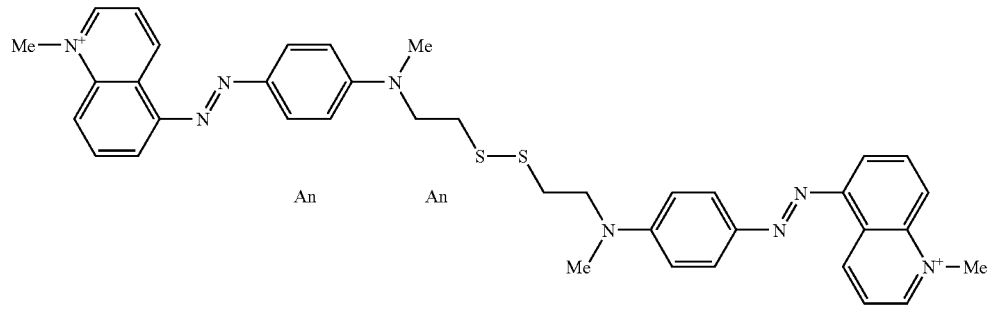
14
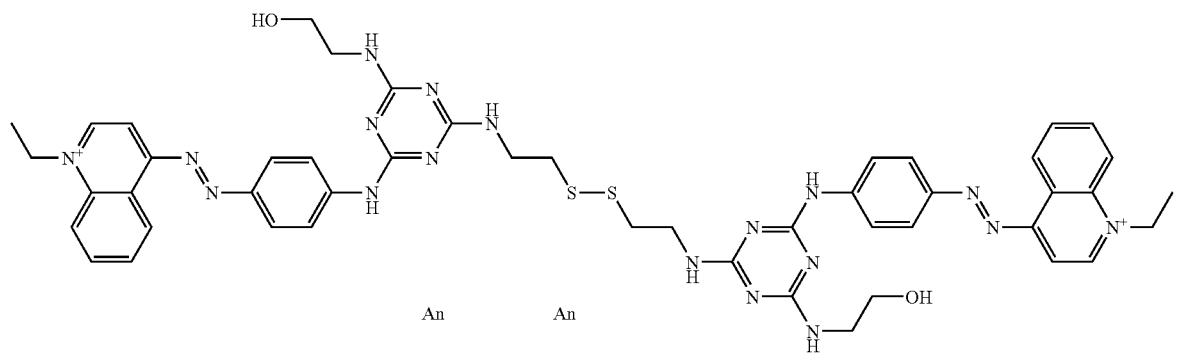
15
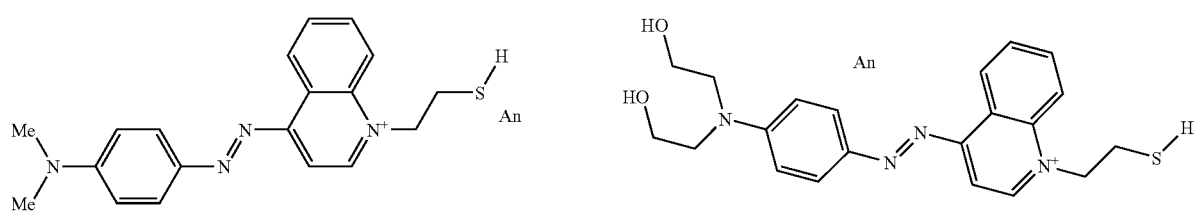
16
17
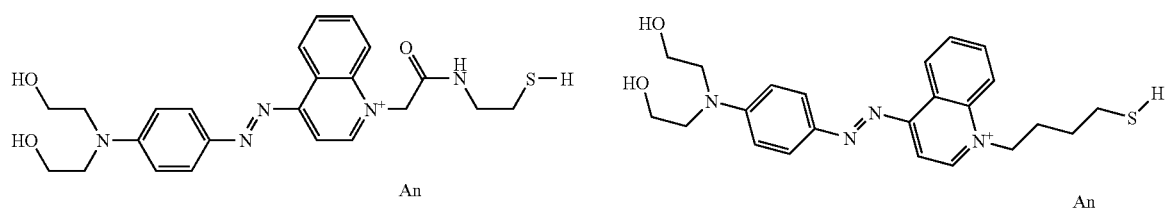
18
19

-continued
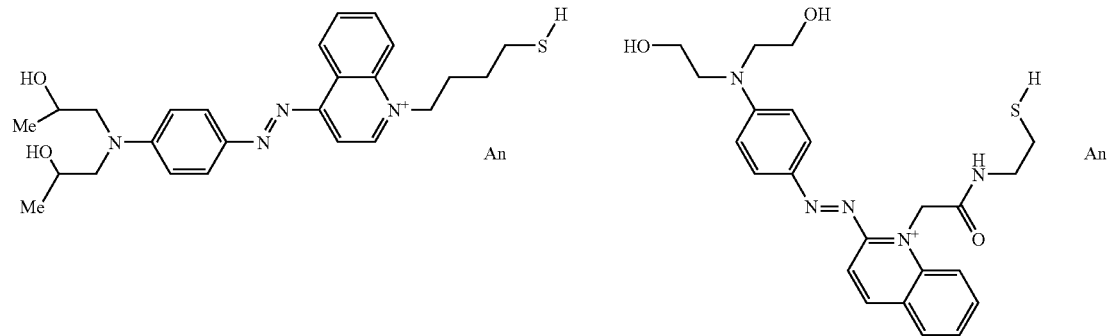
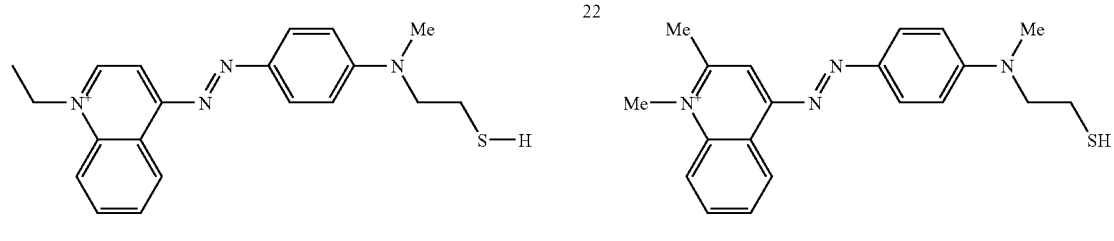
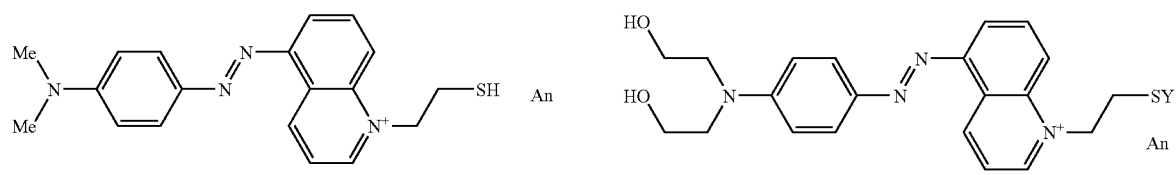
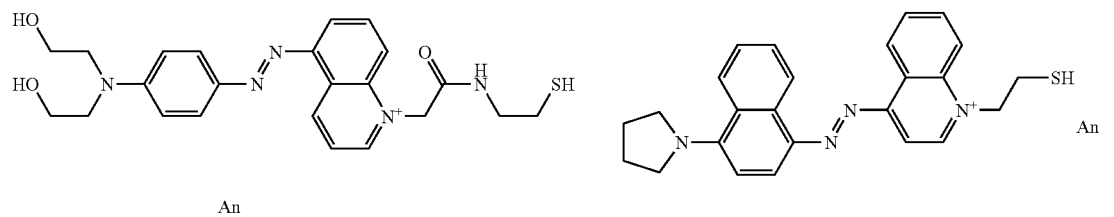
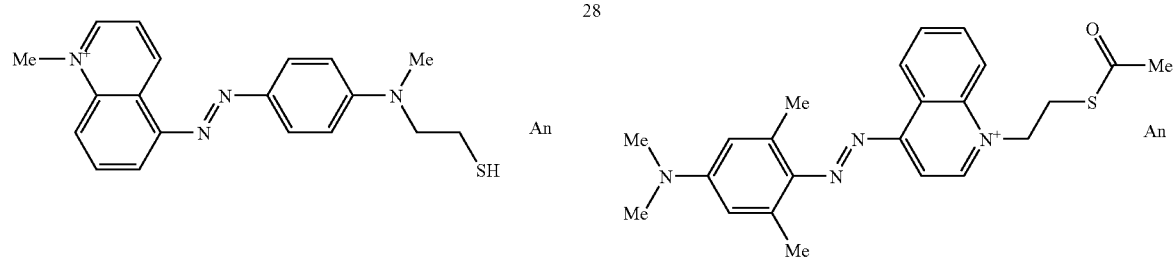
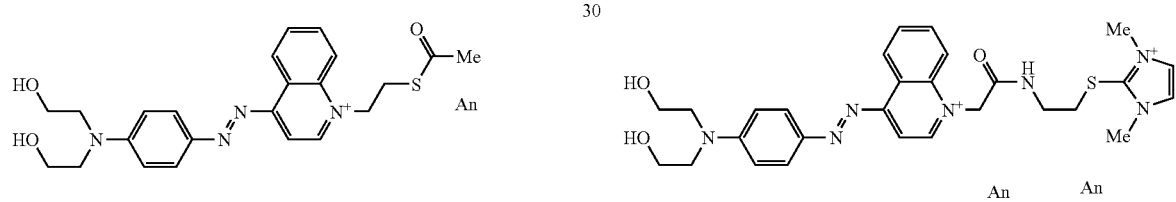

-continued
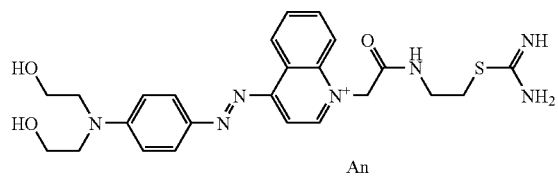
32
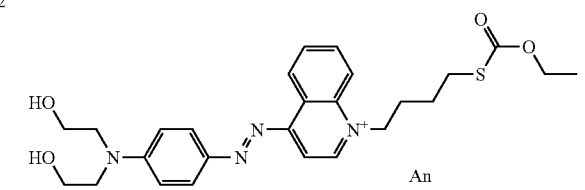
33
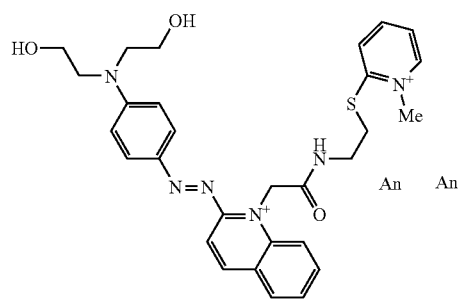
34
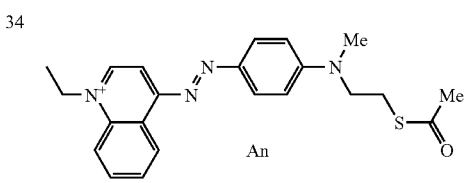
35
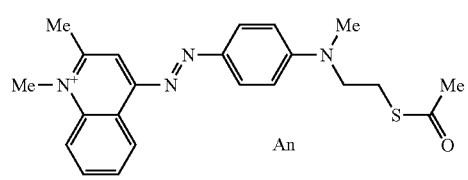
36
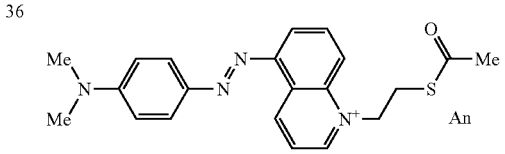
37
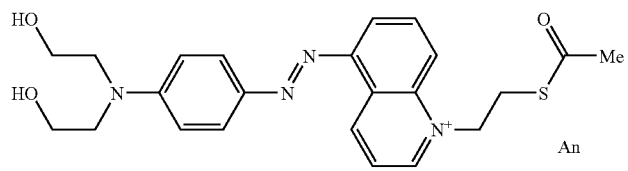
38
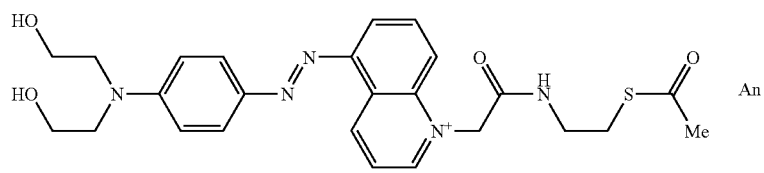
39
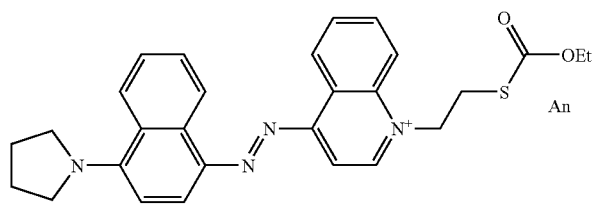
40
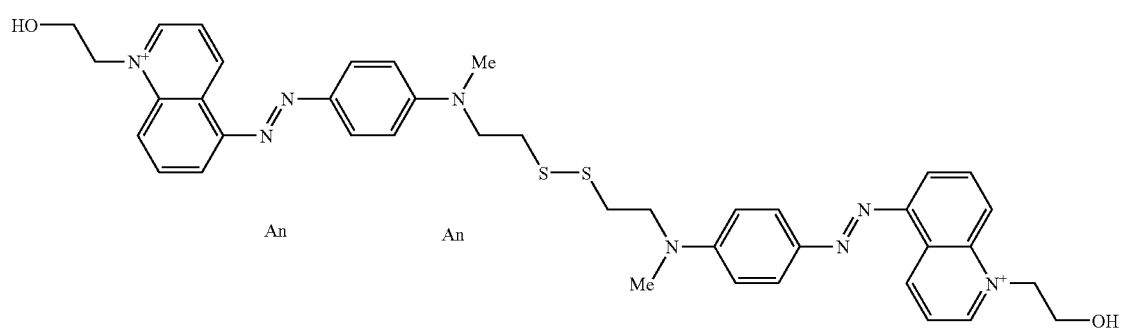
41

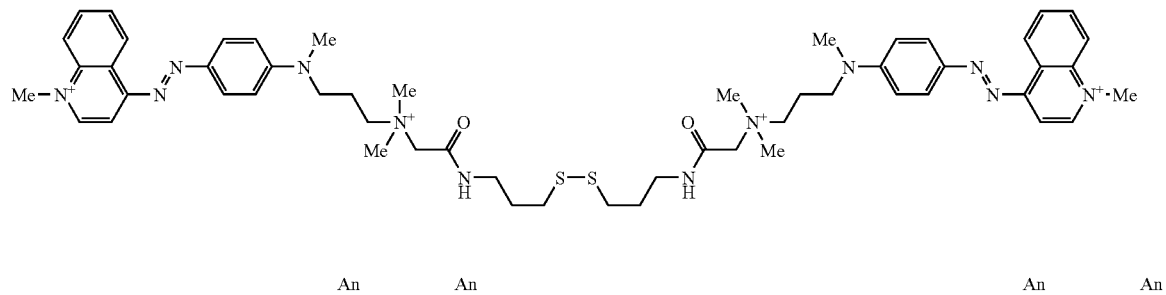
42
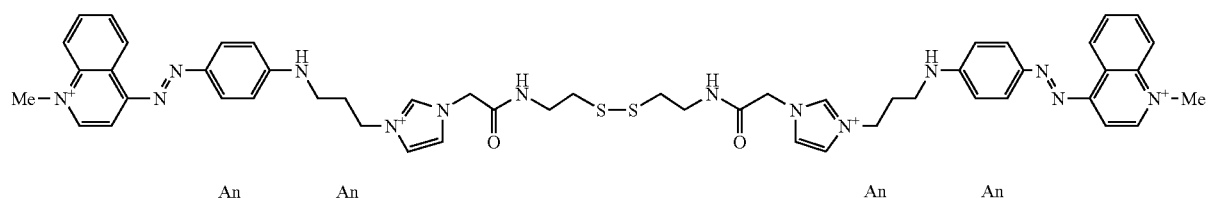
43
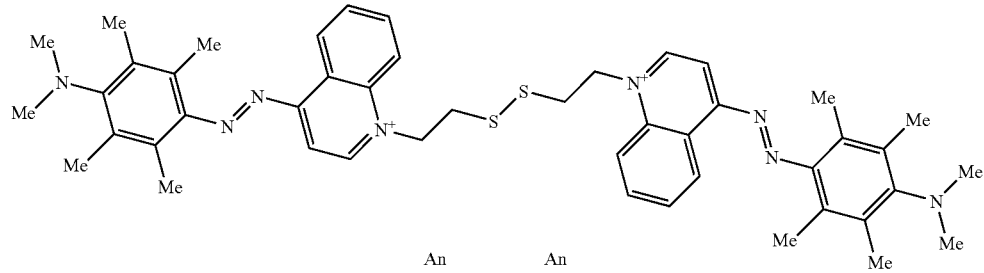
44
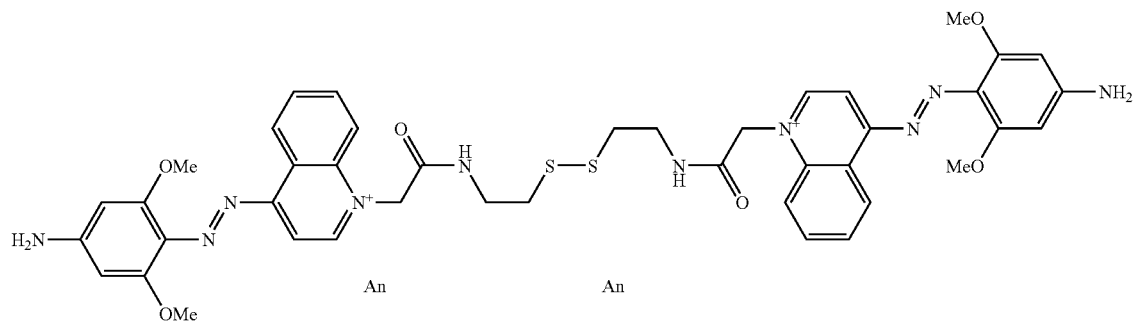
45
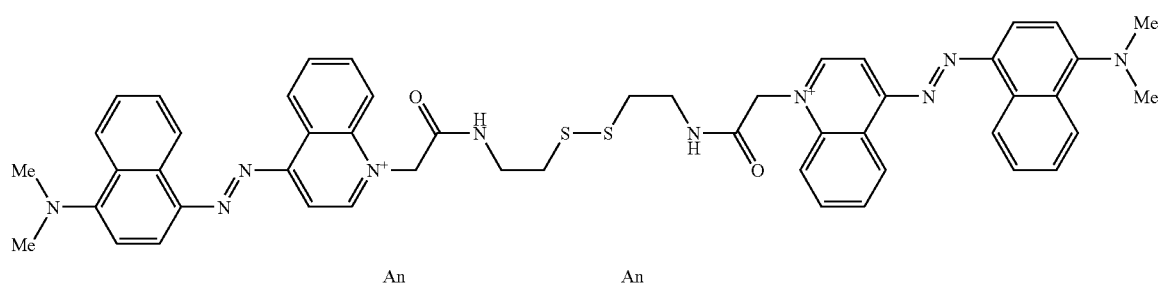
46

-continued
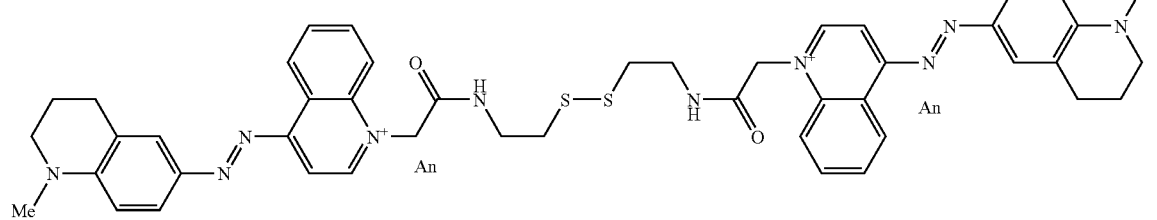
47
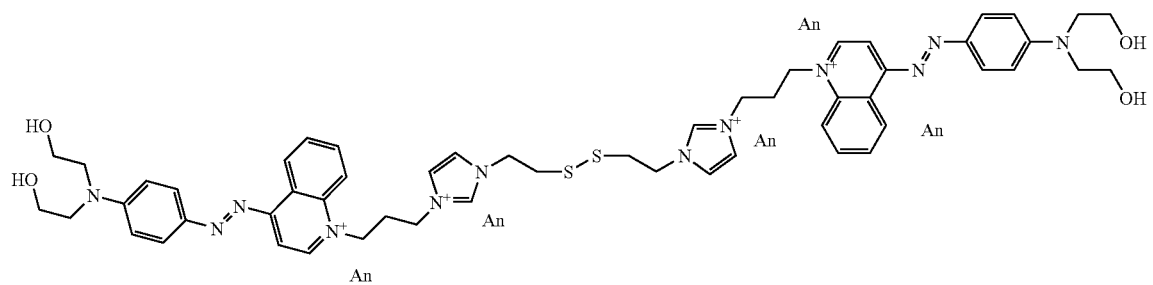
48
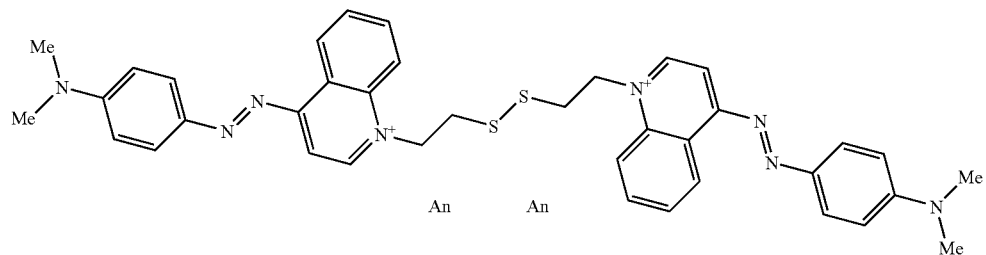
49
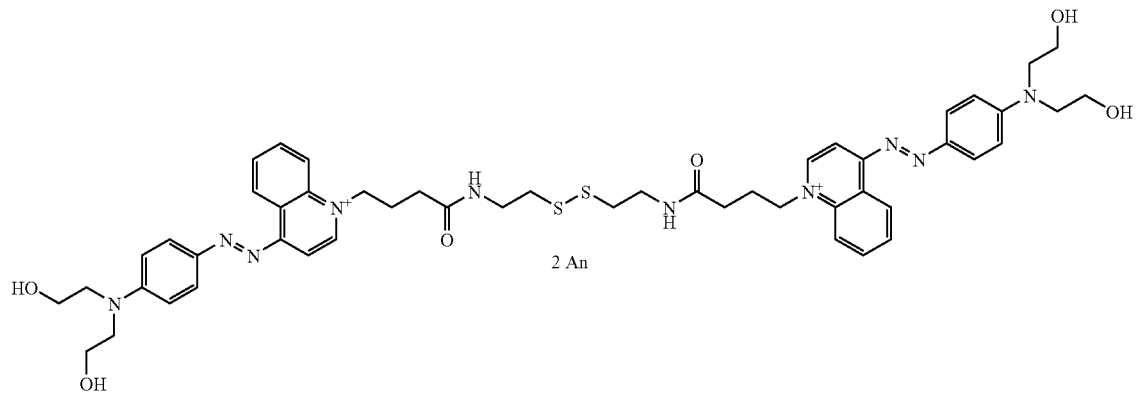
50 with An, which may be identical or different, each chosen from counterions.

9. A dye composition comprising, in a suitable cosmetic medium, at least one dye chosen from dyes of formula (I), dyes of formula (II):

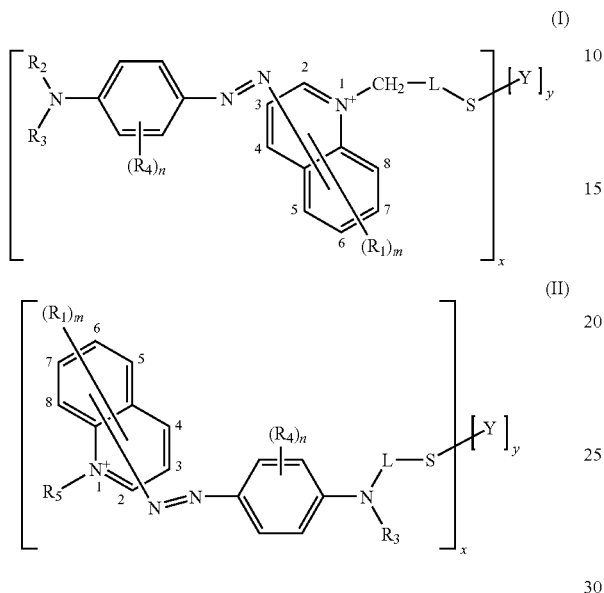

organic acid addition salts, mineral acid addition salts, solvates, tautomers, optical isomers, and geometrical isomers thereof;

wherein, in formula (I) and formula (II):

L is chosen from optionally substituted $C_1$-$C_{20}$ divalent hydrocarbon-based chains optionally interrupted with at least one divalent group, it being understood that two divalent groups or combinations thereof are separated by a $C_1$-$C_6$ divalent hydrocarbon-based chain, said at least one divalent group being chosen from:

—N(R)—; —$N^+$(R)($R^O$)-$An^-$; —O—, —S—, —C(O)—, with R chosen from $C_1$-$C_4$ alkyl groups, $C_2$-$C_6$ (poly)hydroxyalkyl groups, alkoxy ($C_1$-$C_6$) alkyl groups, aryl groups, aryl ($C_1$-$C_6$)alkyl groups, ($C_1$-$C_4$)alkylcarbonylamino ($C_1$-$C_6$)alkyl groups, amino ($C_1$-$C_4$)alkyl groups, the amine of which is substituted with at least one $C_1$-$C_4$ alkyl group which may be identical or different, ($C_1$-$C_6$) alkylcarbonyl groups, and ($C_1$-$C_4$)alkylcarbonylamino groups; and $R^O$ is chosen from hydrogen and R;

cationic heterocyclic and heteroaryl $Het^+An^-$ groups, with $An^-$ chosen from anionic counterions and $Het^+$ chosen from saturated and unsaturated cationic heterocycles comprising 5 to 10 members and saturated and unsaturated cationic heteroaryls comprising 5 to 10 members;

noncationic heterocyclic groups comprising 5 to 10 members; and optionally substituted (hetero) aryl groups;

with L comprising no diazo, hydrazino, aminooxy, nitro, nitroso or peroxide groups;

$R_1$ and $R_4$, independently of one another, are each chosen from:
$C_1$-$C_4$ alkyl groups;
hydroxyl groups;
$C_1$-$C_4$ alkoxy groups;
$C_2$-$C_4$ (poly)hydroxyalkoxy groups;
alkoxycarbonyl groups ($R_aO$—C(O)—) in which $R_a$ is chosen from $C_1$-$C_4$ alkyl groups;
alkylcarbonyloxy groups ($R_aC$(O)—O—) in which $R_a$ is chosen from $C_1$-$C_4$ alkyl groups;
amino groups optionally substituted with at least one $C_1$-$C_4$ alkyl group, which may be identical or different, optionally bearing at least one hydroxyl group, it being possible for the two alkyl groups to optionally form, with the nitrogen atom to which they are attached, a substituted or unsubstituted 5- or 6-membered heterocycle optionally bearing another heteroatom identical to or different from nitrogen;
alkylcarbonylamino groups ($R_aC$(O)—$NR'_a$—) in which $R_a$ is chosen from $C_1$-$C_4$ alkyl groups and $R'_a$ is chosen from hydrogen and $C_1$-$C_4$ alkyl groups;
(di)(alkyl)aminocarbonyl groups (($R_a$)$_2$N—C(O)) in which the $R_a$ groups, which may be identical or different, are each chosen from hydrogen and $C_1$-$C_4$ alkyl groups;
ureido groups (($R_a$)$_2$N—C(O)—$NR_b$—) in which the $R_a$ and $R_b$ groups, independently of one another, are each chosen from hydrogen and $C_1$-$C_4$ alkyl groups;
guanidinium groups (($R_a$)$_2$N—C(=$NH_2^+$)—$NR_b$—) in which the $R_a$ and $R_b$ groups, independently of one another, are each chosen from hydrogen and $C_1$-$C_4$ alkyl groups;
halogens;
or else two adjacent $R_4$ groups can form, with the carbon atoms to which they are attached, a condensed, aromatic 6-membered ring optionally substituted with at least one group, which may be identical or different, chosen from hydroxyl groups, $C_1$-$C_4$ alkyl groups, hydroxycarbonyl groups (HO(O)C—), alkoxycarbonyl groups ($R_aO$ (O)C—) in which $R_a$ is chosen from $C_1$-$C_4$ alkyl groups, (alkyl)sulphonylamino groups ($R_aS$(O)$_2$ $NR_b$) in which $R_a$ is chosen from $C_1$-$C_4$ alkyl groups and $R_b$ is chosen from hydrogen and $C_1$-$C_4$ alkyl groups; $C_1$-$C_4$ alkoxy groups; amino groups optionally substituted with at least one $C_1$-$C_4$ alkyl group, which may be identical or different, and optionally bearing at least one hydroxyl or methylcarbonylamino group, it being possible for the two alkyl groups to optionally form, with the nitrogen atom to which they are attached, a 5- or 6-membered heterocycle optionally bearing another heteroatom identical to or different from nitrogen;

$R_2$ and $R_3$, independently of one another, are each chosen from:
hydrogen;
optionally substituted $C_1$-$C_6$ alkyl groups;
optionally substituted aryl groups;
optionally substituted heteroaryl groups;
optionally substituted aryl ($C_1$-$C_6$)alkyl groups;
optionally substituted heteroaryl ($C_1$-$C_6$)alkyl groups;
cycloalkyl($C_1$-$C_6$)alkyl groups;
heterocycloalkyl($C_1$-$C_6$)alkyl groups;
or else $R_3$, with the nitrogen atom which bears it, and R₄, with the carbon atom which bears it, can optionally together form a 5-, 6- or 7-membered heterocycle; this heterocycle and the aromatic ring attached to the azo group are then condensed; the heterocycle may be saturated or unsaturated, and optionally interrupted with a heteroatom;

or else two contiguous R₂ groups, when n is 2, form, together with the carbon atom which bears them, a benzo group;

or else R₂ and R₃ of formula (I) form, together with the nitrogen atom which bears them, a 5-, 6-, or 7-membered heterocycle;

R₅ is directly attached to the quaternized nitrogen atom by means of a carbon atom and is chosen from:
optionally substituted $C_1$-$C_6$ alkyl groups;
optionally substituted aryl groups;
optionally substituted heteroaryl groups;
optionally substituted aryl ($C_1$-$C_6$)alkyl groups;
optionally substituted heteroaryl($C_1$-$C_6$)alkyl groups;
cycloalkyl($C_1$-$C_6$)alkyl groups; and
heterocycloalkyl($C_1$-$C_6$)alkyl groups;

Y is chosen from:
hydrogen;
alkali metals;
alkaline earth metals;
ammonium groups $N^+R^\alpha R^\beta R^\gamma R^\delta$ and phosphonium groups $P^+R^\alpha R^\beta R^\gamma R^\delta$, with $R^\alpha$, $R^\beta$, $R^\gamma$, and $R^\delta$, which may be identical or different, each chosen from hydrogen and ($C_1$-$C_4$)alkyl groups; and
thiol-function-protecting groups;

An is chosen from anionic counterions;
m is chosen from integers ranging from 0 to 6 inclusive;
n is chosen from integers ranging from 0 to 4 inclusive;
x is 1 or 2;
y is 0 or 1;
it being understood that:
if x is 1, then y is 1 and that if x is 2, then y is zero;
the electroneutrality of the dyes of formula (I) and the dyes of formula (II) is ensured by at least one cosmetically acceptable anionic counterion An, which may or may not be identical.

10. The dye composition according to claim 9, further comprising at least one reducing agent.

11. The dye composition according to claim 9, wherein the at least one dye is present in an amount ranging from 0.001% to 50% by weight relative to the total weight of the composition.

12. A process for dyeing keratin materials, wherein a suitable dye composition comprising at least one dye according to claim 9 is applied to the keratin materials.

13. The process according to claim 12, where the suitable dye composition further is applied before or after the application of the at least one dye.

14. The process according to claim 9, further comprising at least one oxidizing agent.

15. A multicompartment device in which
a first compartment contains a dye composition comprising at least one dye chosen from dyes of formula (I), dyes of formula (II):

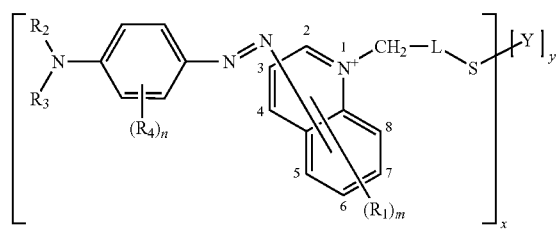

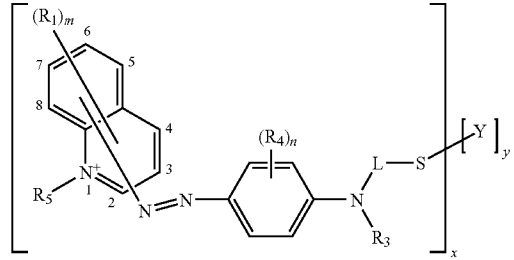

organic acid addition salts, mineral acid addition salts, solvates, tautomers, optical isomers, and geometrical isomers thereof;
wherein, in formula (I) and formula (II):
L is chosen from optionally substituted $C_1$-$C_{20}$ divalent hydrocarbon-based chains optionally interrupted with at least one divalent group, it being understood that two divalent groups or combinations thereof are separated by a $C_1$-$C_6$ divalent hydrocarbon-based chain, said at least one divalent group being chosen from:
—N(R)—; —N⁺(R)(R°)-An⁻; —O—, —S—, —C(O)—, with R chosen from $C_1$-$C_4$ alkyl groups, $C_2$-$C_6$ (poly)hydroxyalkyl groups, alkoxy ($C_1$-$C_6$) alkyl groups, aryl groups, aryl ($C_1$-$C_6$)alkyl groups, ($C_1$-$C_4$)alkylcarbonylamino ($C_1$-$C_6$)alkyl groups, amino ($C_1$-$C_4$)alkyl groups, the amine of which is substituted with at least one $C_1$-$C_4$ alkyl group which may be identical or different, ($C_1$-$C_6$) alkylcarbonyl groups, and ($C_1$-$C_4$)alkylcarbonylamino groups; and R° is chosen from hydrogen and R;
cationic heterocyclic and heteroaryl Het⁺An⁻ groups, with An⁻ chosen from anionic counterions, and
Het⁺ chosen from saturated and unsaturated cationic heterocycles comprising 5 to 10 members and saturated and unsaturated cationic heteroaryls comprising 5 to 10 members;
noncationic heterocyclic groups comprising 5 to 10 members; and
optionally substituted (hetero)aryl groups;
with L comprising no diazo, hydrazino, aminooxy, nitro, nitroso or peroxide groups;

R₁ and R₄, independently of one another, are each chosen from:
$C_1$-$C_4$ alkyl groups;
hydroxyl groups;
$C_1$-$C_4$ alkoxy groups;
$C_2$-$C_4$ (poly)hydroxyalkoxy groups;
alkoxycarbonyl groups ($R_aO$—C(O)—) in which $R_a$ is chosen from $C_1$-$C_4$ alkyl groups;
alkylcarbonyloxy groups ($R_aC(O)$—O—) in which $R_a$ is chosen from $C_1$-$C_4$ alkyl groups;

amino groups optionally substituted with at least one $C_1$-$C_4$ alkyl group, which may be identical or different, optionally bearing at least one hydroxyl group, it being possible for the two alkyl groups to optionally form, with the nitrogen atom to which they are attached, a substituted or unsubstituted 5- or 6-membered heterocycle optionally bearing another heteroatom identical to or different from nitrogen;

alkylcarbonylamino groups ($R_aC(O)$—$NR'_a$—) in which $R_a$ is chosen from $C_1$-$C_4$ alkyl groups and $R'_a$ is chosen from hydrogen and $C_1$-$C_4$ alkyl groups;

(di)(alkyl)aminocarbonyl groups (($R_a$)$_2$N—C(O)) in which the $R_a$ groups, which may be identical or different, are each chosen from hydrogen and $C_1$-$C_4$ alkyl groups;

ureido groups (($R_a$)$_2$N—C(O)—$NR_b$—) in which the $R_a$ and $R_b$ groups, independently of one another, are each chosen from hydrogen and $C_1$-$C_4$ alkyl groups;

guanidinium groups (($R_a$)$_2$N—C(=$NH_2^+$)—$NR_b$—) in which the $R_a$ and $R_b$ groups, independently of one another, are each chosen from hydrogen and $C_1$-$C_4$ alkyl groups;

halogens;

or else two adjacent $R_4$ groups can form, with the carbon atoms to which they are attached, a condensed, aromatic 6-membered ring optionally substituted with at least one group, which may be identical or different, chosen from hydroxyl groups, $C_1$-$C_4$ alkyl groups, hydroxycarbonyl groups (HO(O)C—), alkoxycarbonyl groups ($R_aO(O)C$—) in which $R_a$ is chosen from $C_1$-$C_4$ alkyl groups, (alkyl) sulphonylamino groups ($R_aS(O)_2NR_b$) in which $R_a$ is chosen from $C_1$-$C_4$ alkyl groups and $R_b$ is chosen from hydrogen and $C_1$-$C_4$ alkyl groups; $C_1$-$C_4$ alkoxy groups; amino groups optionally substituted with at least one $C_1$-$C_4$ alkyl group, which may be identical or different, and optionally bearing at least one hydroxyl or methylcarbonylamino group, it being possible for the two alkyl groups to optionally form, with the nitrogen atom to which they are attached, a 5- or 6-membered heterocycle optionally bearing another heteroatom identical to or different from nitrogen;

$R_2$ and $R_3$, independently of one another, are each chosen from:
hydrogen;
optionally substituted $C_1$-$C_6$ alkyl groups;
optionally substituted aryl groups;
optionally substituted heteroaryl groups;
optionally substituted aryl ($C_1$-$C_6$)alkyl groups;
optionally substituted heteroaryl ($C_1$-$C_6$)alkyl groups;
cycloalkyl($C_1$-$C_6$)alkyl groups;
heterocycloalkyl($C_1$-$C_6$)alkyl groups;
or else $R_3$, with the nitrogen atom which bears it, and $R_4$, with the carbon atom which bears it, can optionally together form a 5-, 6- or 7-membered heterocycle; this heterocycle and the aromatic ring attached to the azo group are then condensed; the heterocycle may be saturated or unsaturated, and optionally interrupted with a heteroatom;
or else two contiguous $R_2$ groups, when n is 2, form, together with the carbon atom which bears them, a benzo group;
or else $R_2$ and $R_3$ of formula (I) form, together with the nitrogen atom which bears them, a 5-, 6-, or 7-membered heterocycle;

$R_5$ is directly attached to the quaternized nitrogen atom by means of a carbon atom and is chosen from:
optionally substituted $C_1$-$C_6$ alkyl groups;
optionally substituted aryl groups;
optionally substituted heteroaryl groups;
optionally substituted aryl ($C_1$-$C_6$)alkyl groups;
optionally substituted heteroaryl($C_1$-$C_6$)alkyl groups;
cycloalkyl($C_1$-$C_6$)alkyl groups; and
heterocycloalkyl($C_1$-$C_6$)alkyl groups;

Y is chosen from:
hydrogen;
alkali metals;
alkaline earth metals;
ammonium groups $N^+R^\alpha R^\beta R^\gamma R^\delta$ and phosphonium groups $P^+R^\alpha R^\beta R^\gamma R^\delta$, with $R^\alpha$, $R^\beta$, $R^\gamma$, and $R^\delta$, which may be identical or different, each chosen from hydrogen and ($C_1$-$C_4$)alkyl groups; and
thiol-function-protecting groups;

An is chosen from anionic counterions;
m is chosen from integers ranging from 0 to 6 inclusive;
n is chosen from integers ranging from 0 to 4 inclusive;
x is 1 or 2;
y is 0 or 1;
it being understood that:
if x is 1, then y is 1 and that if x is 2, then y is zero;
the electroneutrality of the dyes of formula (I) and the dyes of formula (II) is ensured by at least one cosmetically acceptable anionic counterion An, which may or may not be identical, and
a second compartment comprising at least one reducing agent.

* * * * *

UNITED STATES PATENT AND TRADEMARK OFFICE
CERTIFICATE OF CORRECTION

PATENT NO. : 7,967,872 B2
APPLICATION NO. : 12/677450
DATED : June 28, 2011
INVENTOR(S) : Nicolas Daubresse et al.

Page 1 of 1

It is certified that error appears in the above-identified patent and that said Letters Patent is hereby corrected as shown below:

IN THE CLAIMS:

Column 78, Claim 7, structure "Id"

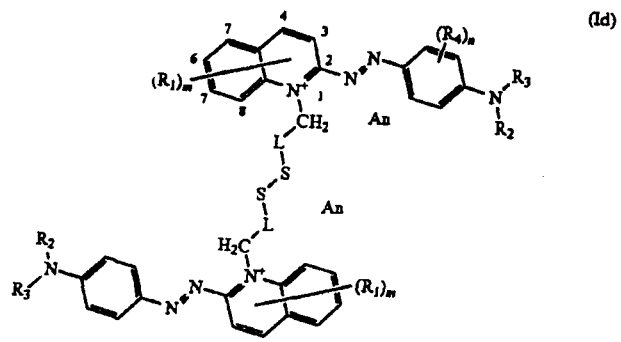

should read:

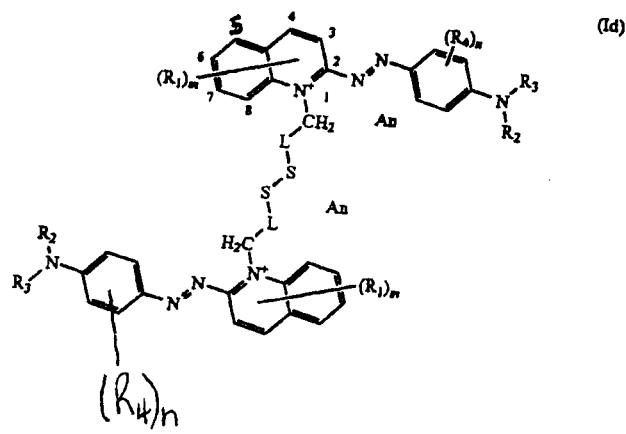

Signed and Sealed this
Twenty-seventh Day of September, 2011

David J. Kappos
*Director of the United States Patent and Trademark Office*